(12) United States Patent
Lee et al.

(10) Patent No.: US 11,761,019 B2
(45) Date of Patent: Sep. 19, 2023

(54) PHARMACEUTICAL COMPOSITION FOR PREVENTING OR TREATING CARDIAC ARRHYTHMIA

(71) Applicant: BETHPHAGEN INC., Gwangju (KR)

(72) Inventors: Min-Ah Lee, Gwangju (KR); Tae Hwan Kwak, Yongin-si (KR); Woo Jin Park, Gwangju (KR)

(73) Assignee: BETHPHAGEN INC., Gwangju (KR)

( * ) Notice: Subject to any disclaimer, the term of this patent is extended or adjusted under 35 U.S.C. 154(b) by 534 days.

(21) Appl. No.: 16/651,889

(22) PCT Filed: Sep. 28, 2018

(86) PCT No.: PCT/KR2018/011529
§ 371 (c)(1),
(2) Date: Mar. 27, 2020

(87) PCT Pub. No.: WO2019/066556
PCT Pub. Date: Apr. 4, 2019

(65) Prior Publication Data
US 2020/0263200 A1 Aug. 20, 2020

(30) Foreign Application Priority Data
Sep. 29, 2017 (KR) ........................ 10-2017-0127550

(51) Int. Cl.
*A61K 38/17* (2006.01)
*A61P 9/06* (2006.01)
*C12N 15/86* (2006.01)

(52) U.S. Cl.
CPC .............. *C12N 15/86* (2013.01); *A61K 38/17* (2013.01)

(58) Field of Classification Search
CPC .......... C12N 15/86; C12N 2750/14143; A61K 38/17; A61K 48/005; A61K 48/00; A61P 9/06
See application file for complete search history.

(56) References Cited

U.S. PATENT DOCUMENTS

2004/0106954 A1* 6/2004 Whitehurst .......... A61N 1/3627
607/3
2009/0239940 A1 9/2009 Del Monte et al.

FOREIGN PATENT DOCUMENTS

| EP | 1382347 A1 | 1/2004 | |
| EP | 2556839 A2 * | 2/2013 | ......... A61K 31/7088 |
| KR | 10-2011-0105957 A | 9/2011 | |
| KR | 10-2017-0056460 A | 5/2017 | |
| WO | 2006/007444 A2 | 1/2006 | |

OTHER PUBLICATIONS

Overview of Arrhythmias from Merck Manual, pp. 1-9. Accessed Oct. 19, 2022. (Year: 2022).*
Ablation for Cardiac Arrhythmia from Merck Manual, pp. 1-2. Accessed Oct. 19, 2022. (Year: 2022).*
Heart Failure from Merck Manual, pp. 1-23. Accessed Oct. 19, 2022. (Year: 2022).*
Southern Hills Hospital & Medical Center, "Arrhythmia can lead to hear failure, and heart failure can lead to arrhythmia," pp. 1-8. Jan. 13, 2020. (Year: 2020).*
Xun Ai, et al., "Ca2+/Calmodulin-Dependent Protein Kinase Modulates Cardiac Ryanodine Receptor Phosphorylation and Sarcoplasmic Reticulum Ca2+ Leak in Heart Failure", Circulation Research, 2005, pp. 1314-1322, vol. 97.
Paari Dominic Swaminathan, et al., "Calmodulin-Dependent Protein Kinase II: Linking Heart Failure and Arrhythmias", Circulation Research, Jun. 8, 2012, pp. 1661-1677, vol. 110.
Dariush Mozaffarian, MD, DrPH, et al., "Heart Disease and Stroke Statistics—2015 Update A Report From the American Heart Association", Circulation, Jan. 27, 2015, pp. e29-e322, vol. 131.
Kurt C Roberts-Thomson, et al., "The diagnosis and management of ventricular arrhythmias", Nature Reviews Cardiology, Jun. 2011, pp. 311-321, vol. 8.
Jason Andrade, et al., "The Clinical Profile and Pathophysiology of Atrial Fibrillation: Relationships Among Clinical Features, Epidemiology, and Mechanisms", Circulation Research, Apr. 25, 2014, pp. 1453-1468, vol. 114.
John Camm, "Antiarrhythmic drugs for the maintenance of sinus rhythm: Risks and benefits", International Journal of Cardiology, 2012, pp. 362-371, vol. 155.
International Search Report for PCT/KR2018/011529 dated Jan. 2, 2019 (PCT/ISA/210).
Gurevich M.A., "Heart rhythm disorders and their correction in chronic heart failure", Russian Journal of Cardiology, 2005; (3): pp. 5-10 (7 pages).
Jin Hee Kim et al., "High Cleavage Efficiency of a 2A Peptide Derived from Porcine Teschovirus-1 in Human Cell Lines, Zebrafish and Mice", Plos One, Apr. 29, 2011, vol. 6, No. 4, pp. 1-8 (8 pages).
Dongtak Jeong et al., "Matricellular Protein CCN5 Reverses Established Cardiac Fibrosis", Journal of the American College of Cardiology, Mar. 28, 2016, vol. 67, No. 13, pp. 1556-1568 (13 pages).
Robert G. Gourdie et al., "Novel therapeutic strategies targeting fibroblasts and fibrosis in heart disease", Nature Reviews Drug Discovery, Sep. 1, 2016, vol. 15, No. 9, pp. 620-638 (19 pages).

* cited by examiner

*Primary Examiner* — Julie Ha
(74) *Attorney, Agent, or Firm* — Sughrue Mion, PLLC

(57) ABSTRACT

A pharmaceutical composition suitable for preventing or treating cardiac arrhythmia is disclosed. The pharmaceutical composition contains, as an active ingredient, a CCN5 protein or a nucleotide encoding the CCN5 protein. The pharmaceutical composition inhibits the pathological activity of CaMKII, which induces cardiac electrical abnormalities that is the main cause of atrial arrhythmia and ventricular arrhythmia, so as to restore the electrical functions, and inhibits the activity of myofibroblasts causing structural abnormalities. Therefore, the pharmaceutical composition can be effectively used in the prevention or treatment of cardiac arrhythmia.

17 Claims, 46 Drawing Sheets
Specification includes a Sequence Listing.

[Fig. 1]
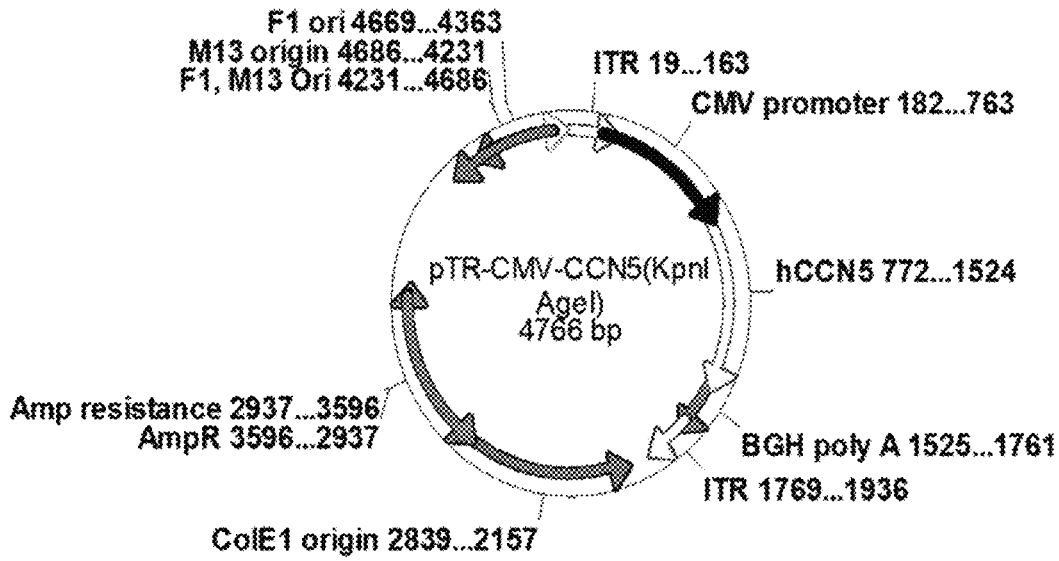
[Fig. 2]
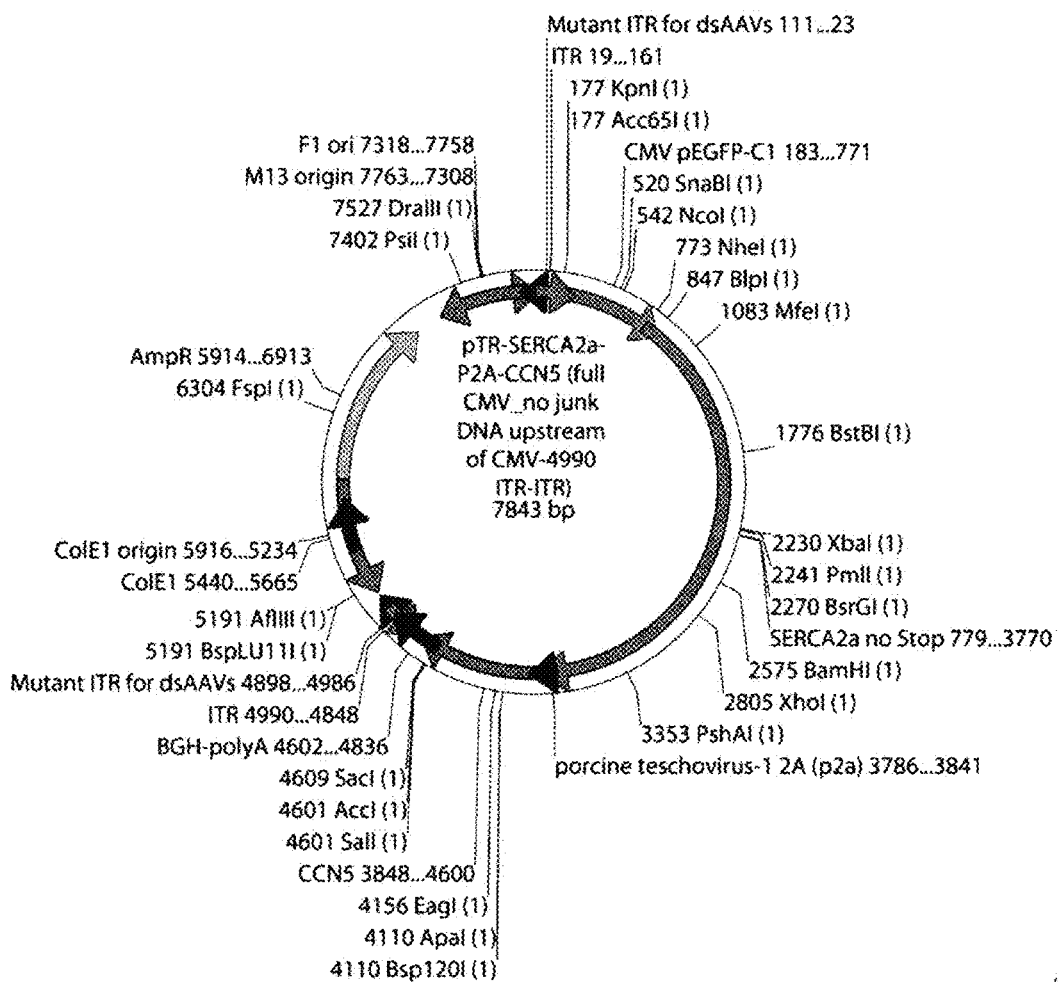

[Fig. 3a]
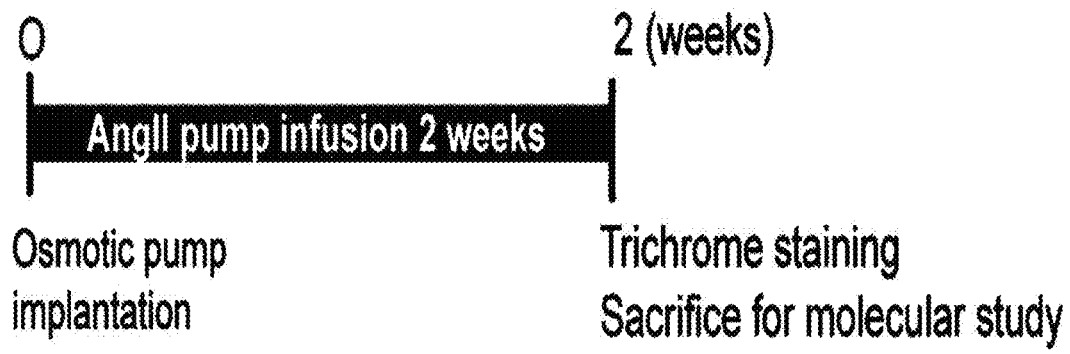
[Fig. 3b]
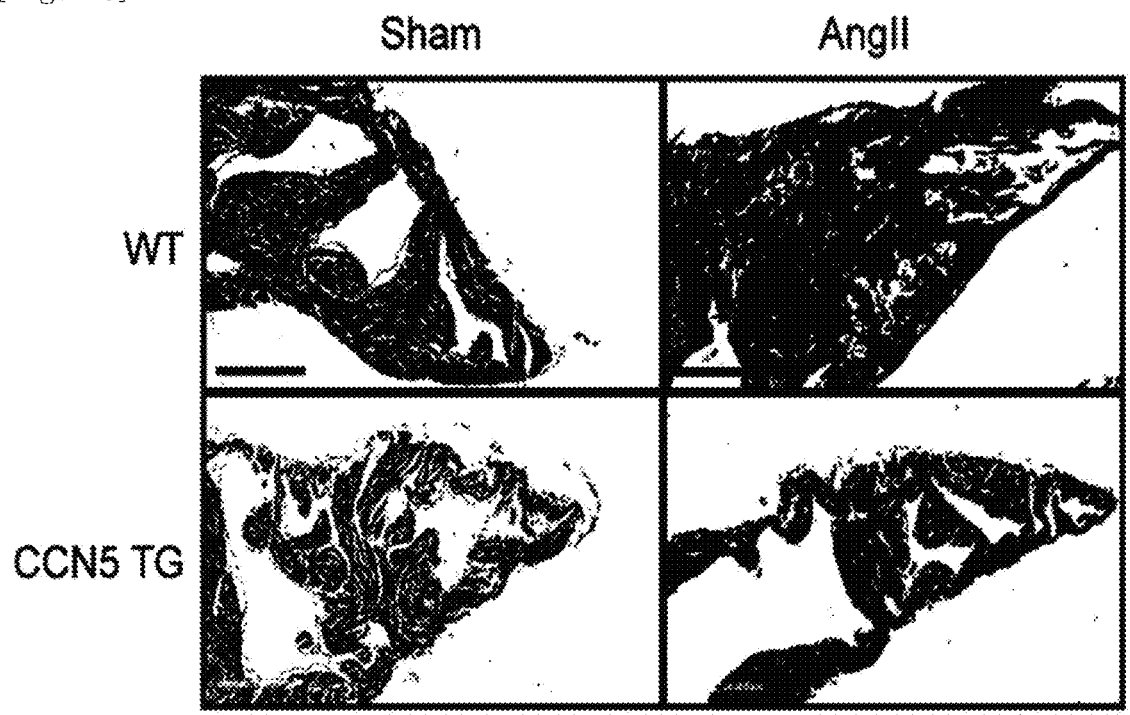

[Fig. 3c]
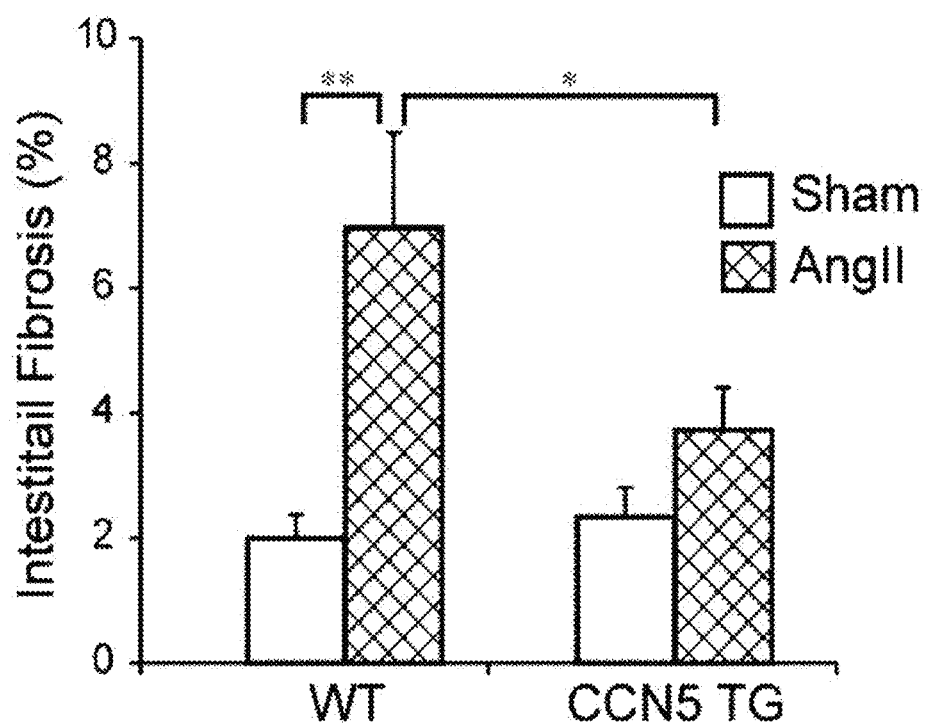

[Fig. 3d]
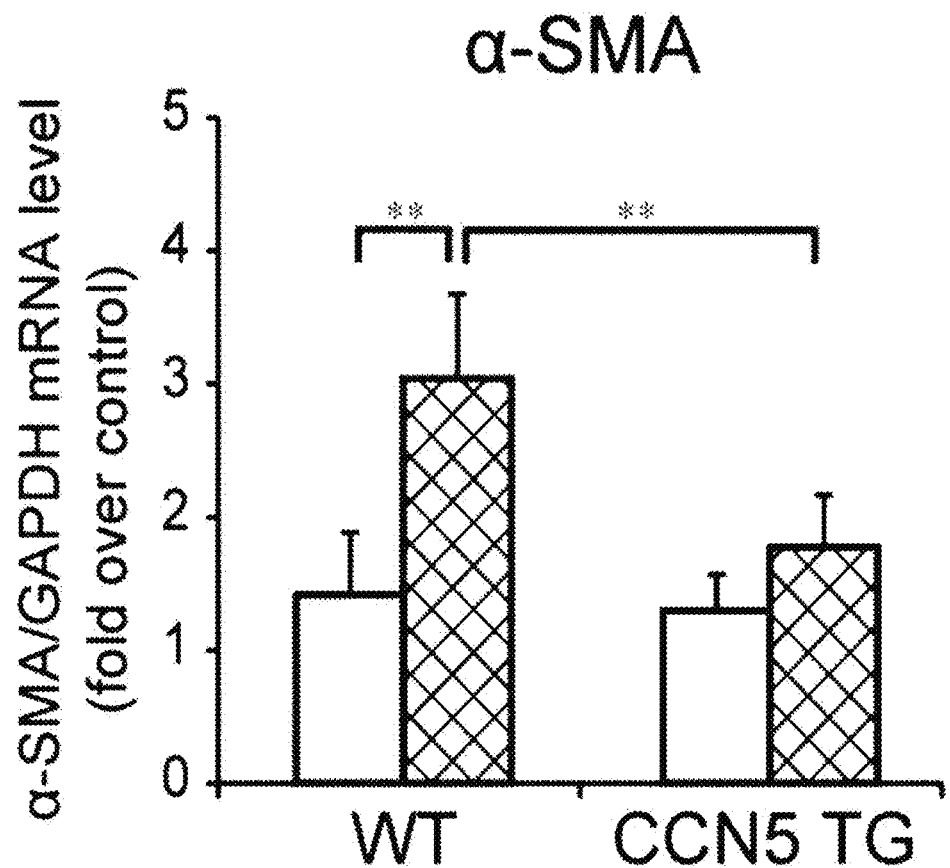

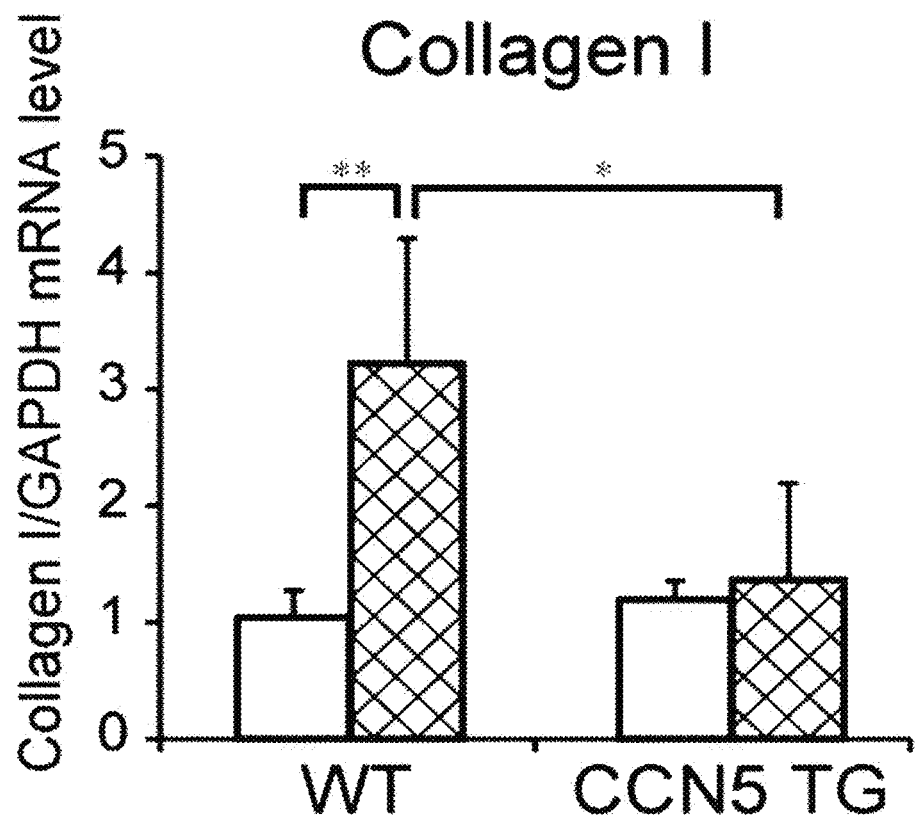
[Fig. 3e]

[Fig. 3f]
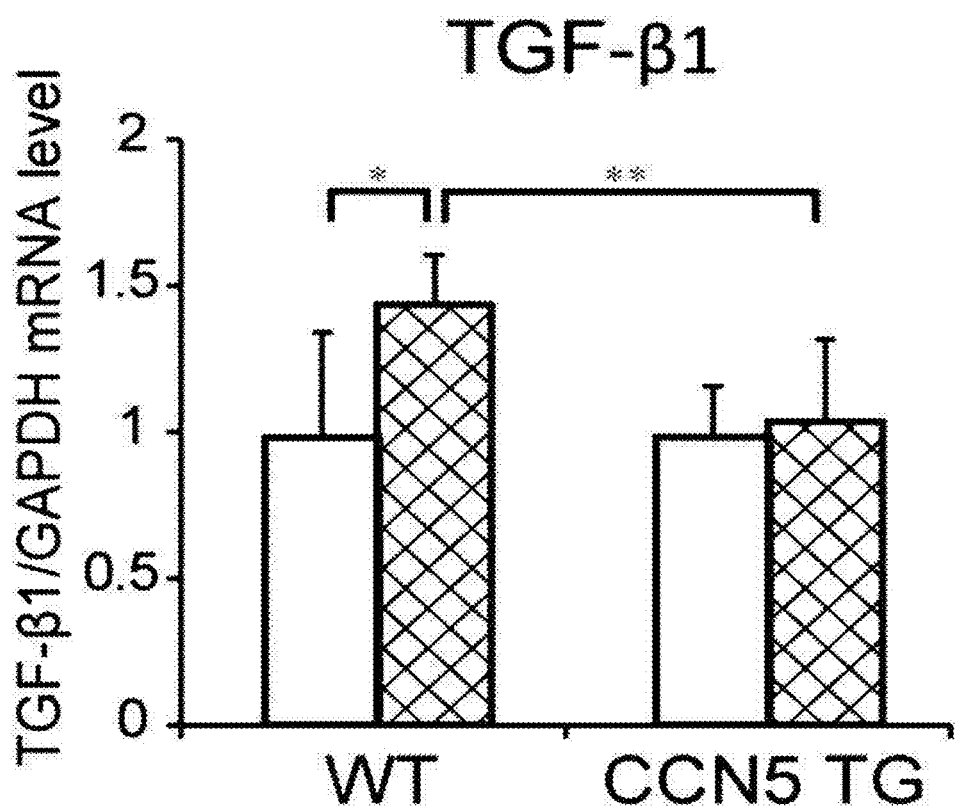

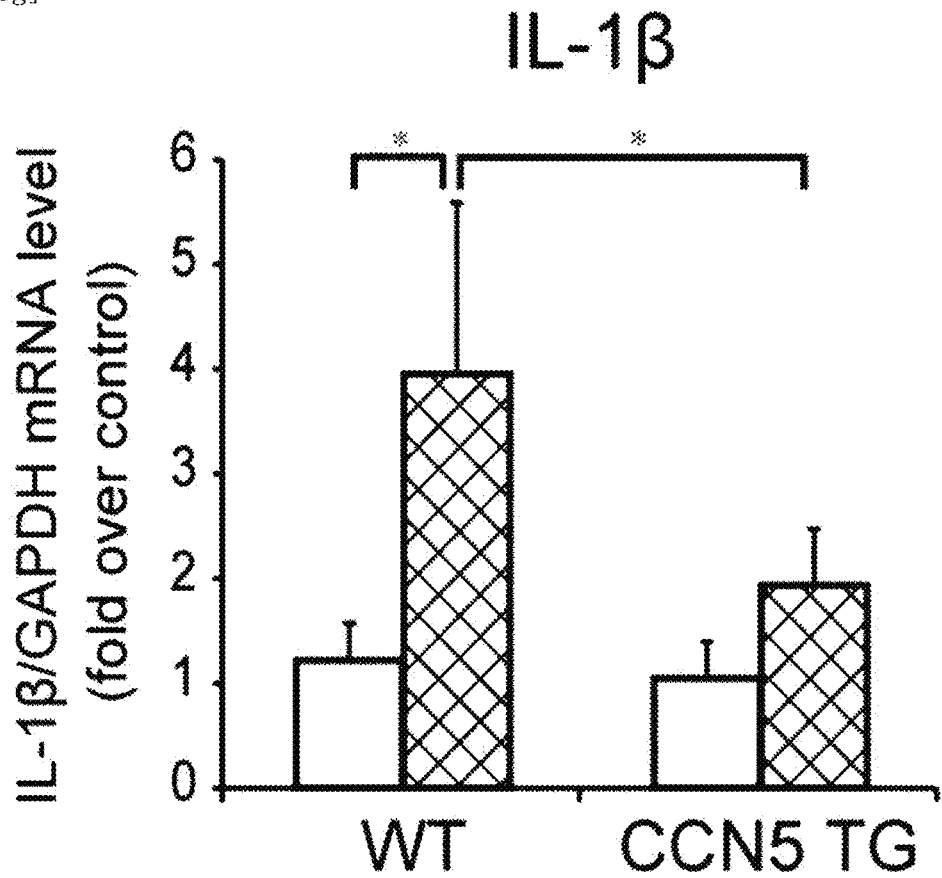
[Fig. 3g]

[Fig. 3h]
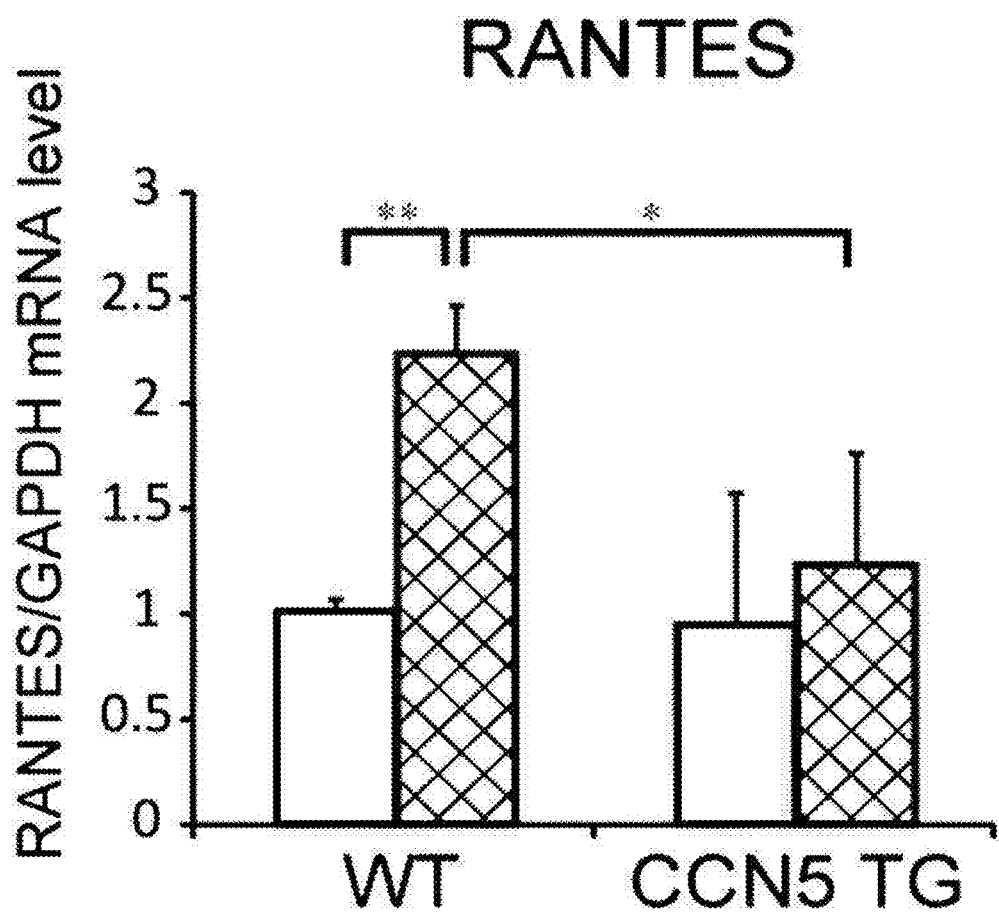

[Fig. 3i]
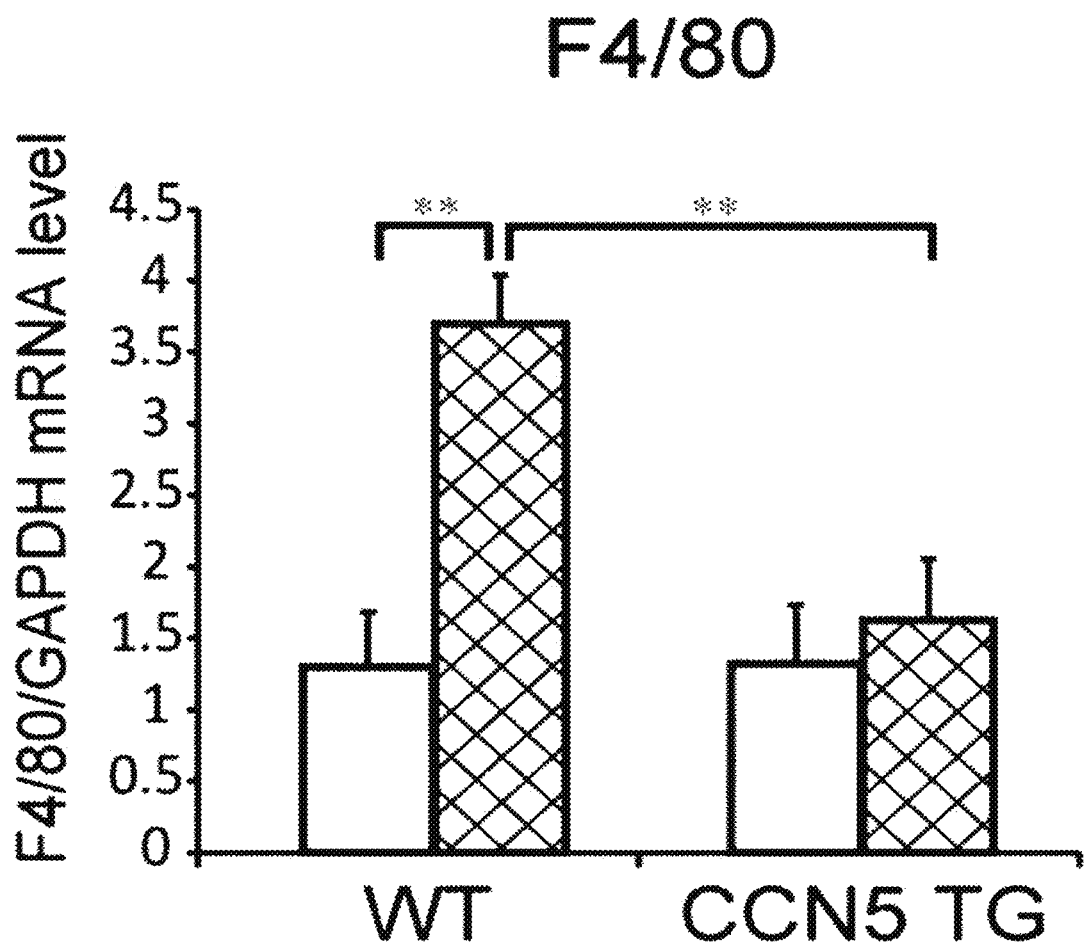

[Fig. 3j]
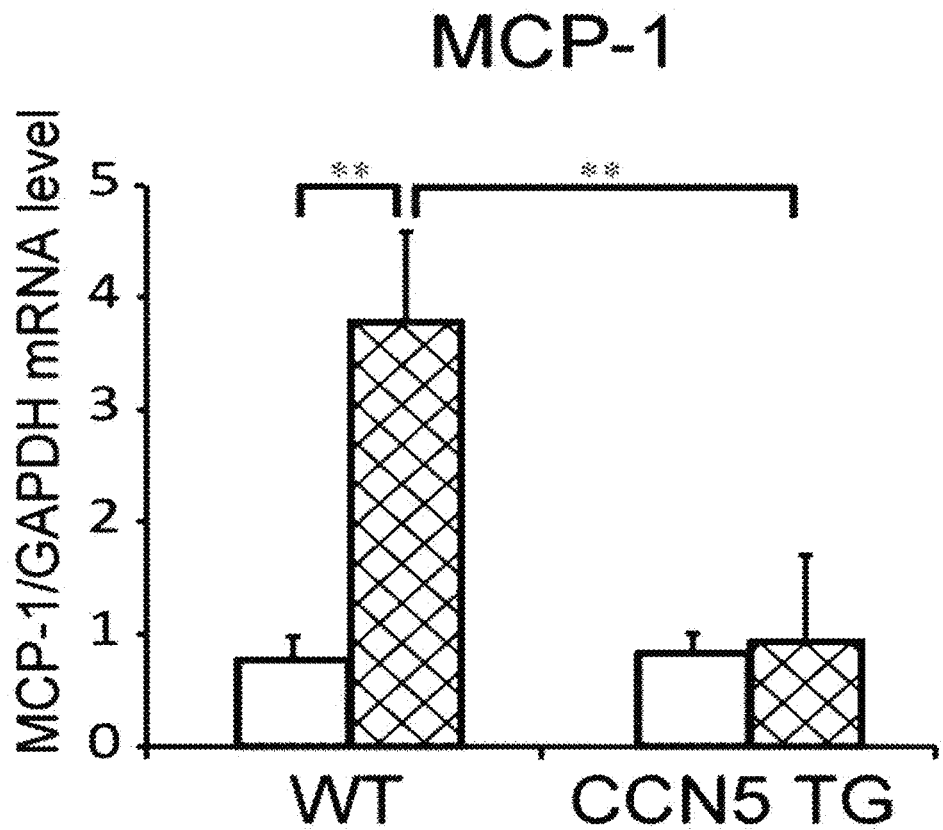
[Fig. 4a]
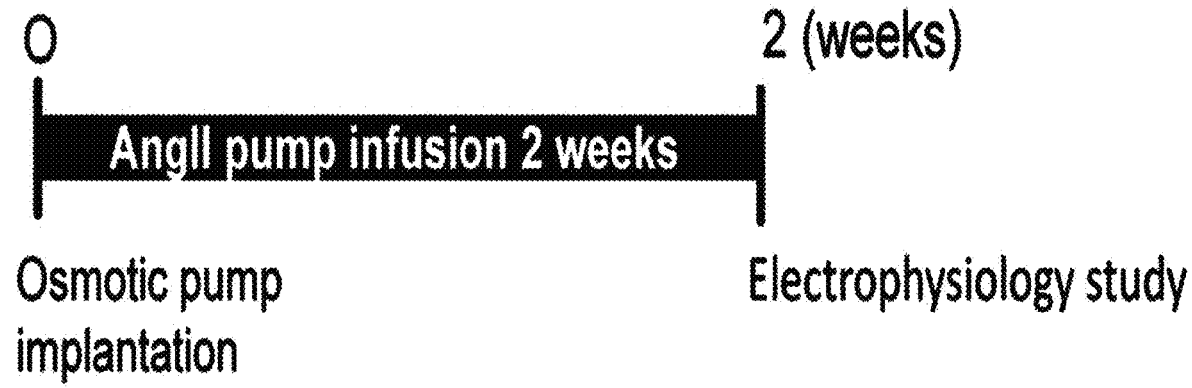

[Fig. 4b]
X-axis: time (unit: sec)
Y-axis: volts (unit: mV)
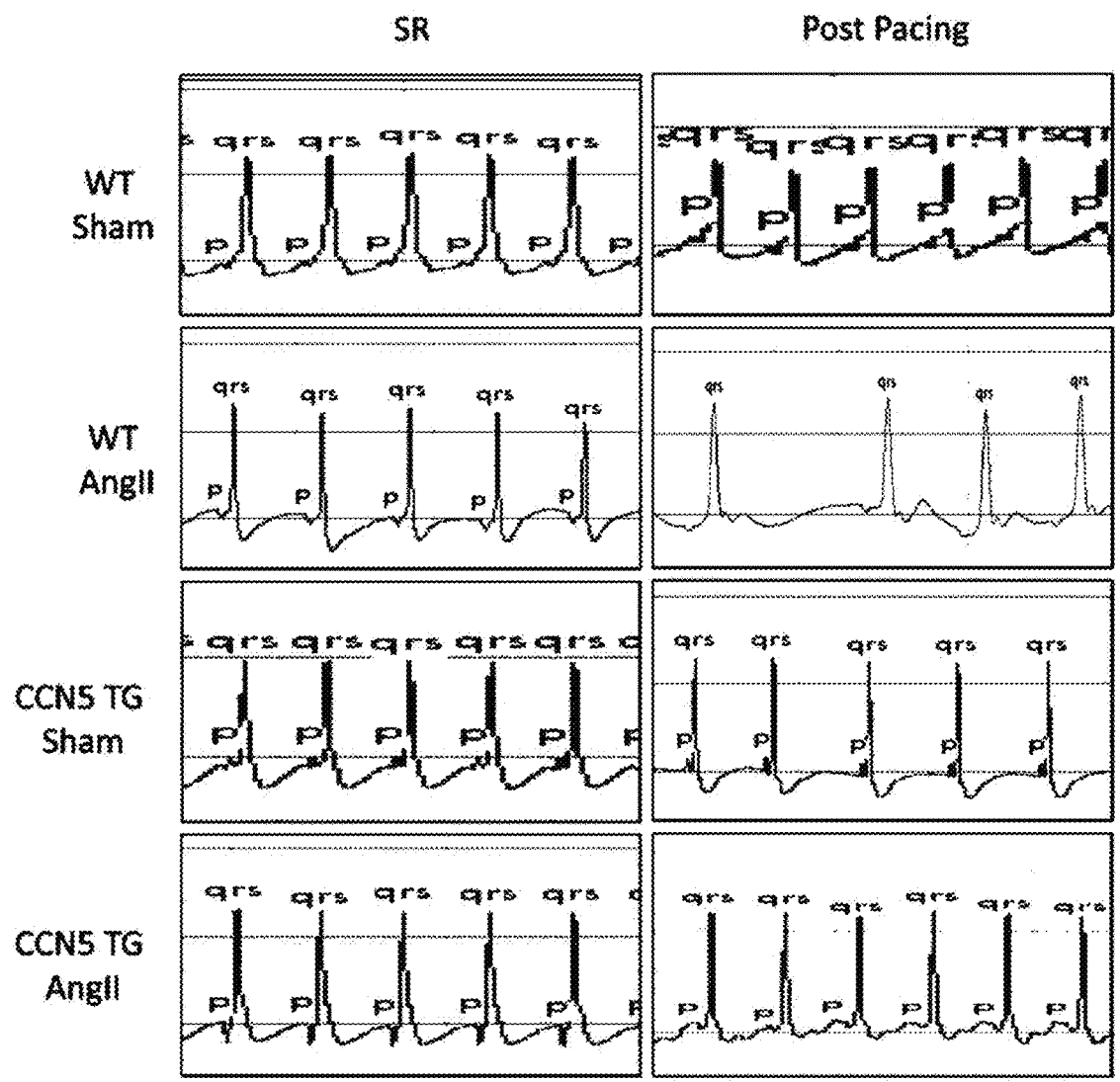

[Fig. 4c]
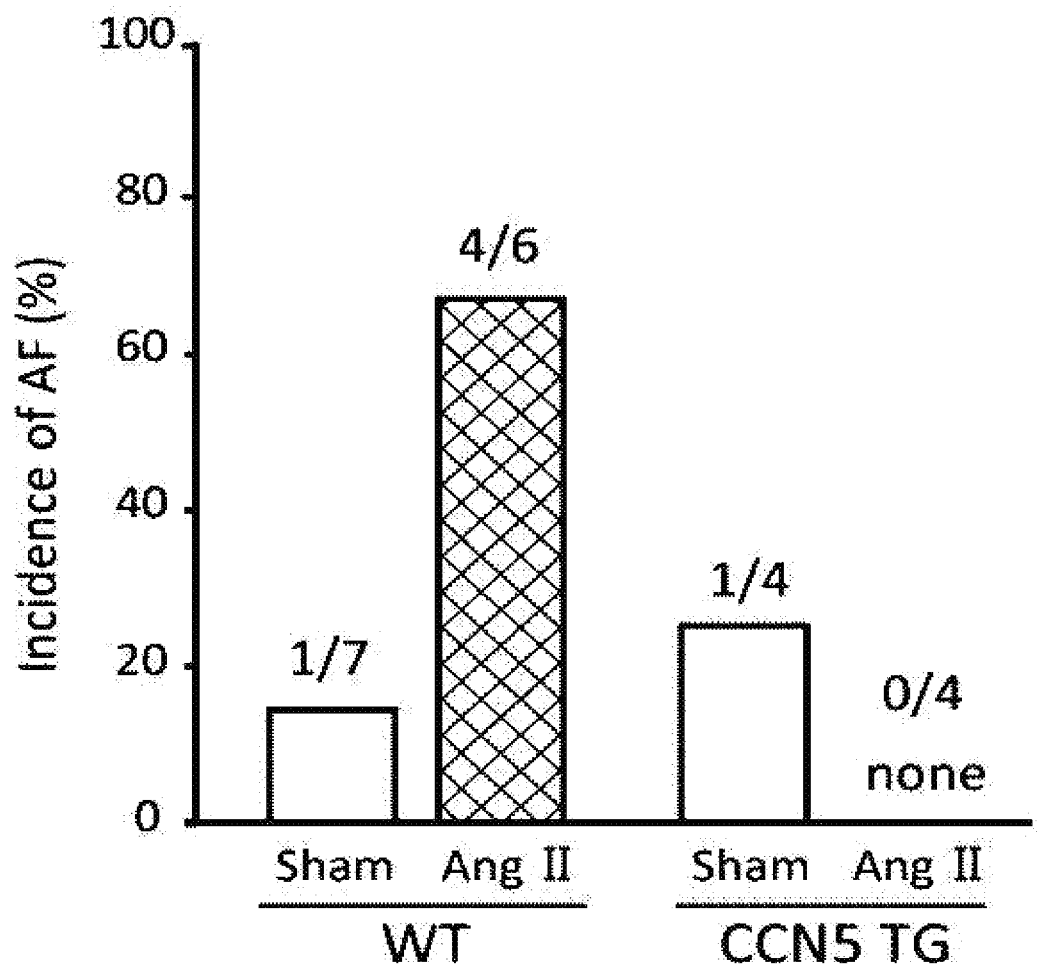
[Fig. 5a]

[Fig. 5b]
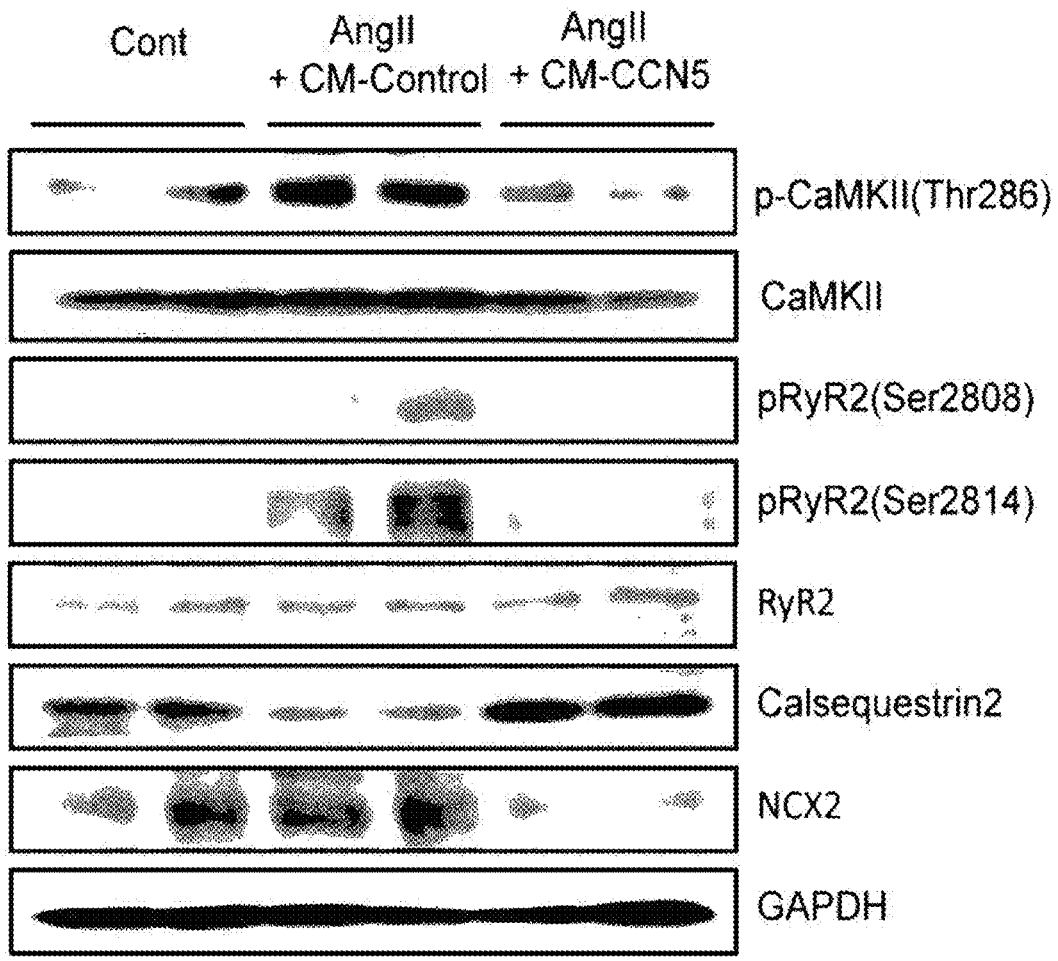
[Fig. 5c]
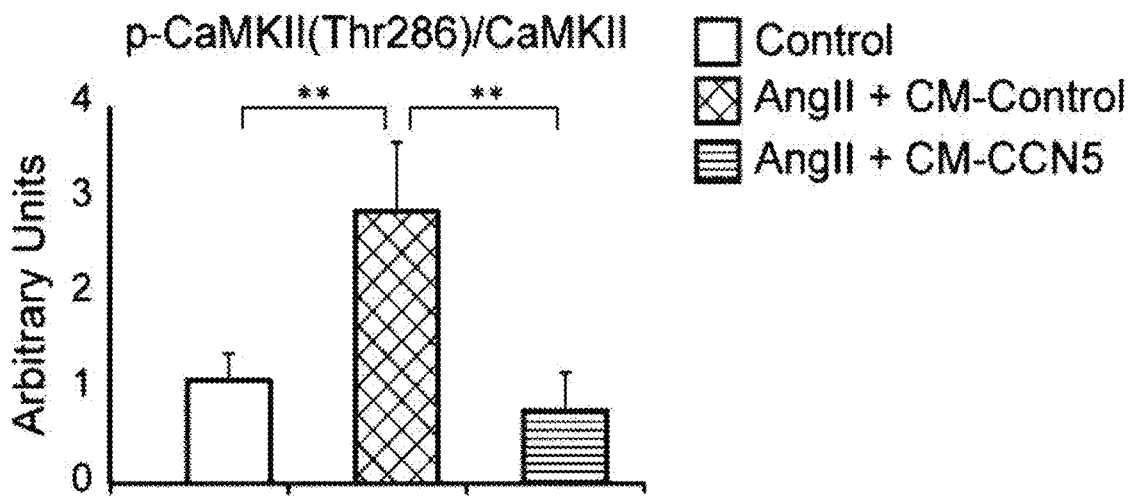

[Fig. 5d]
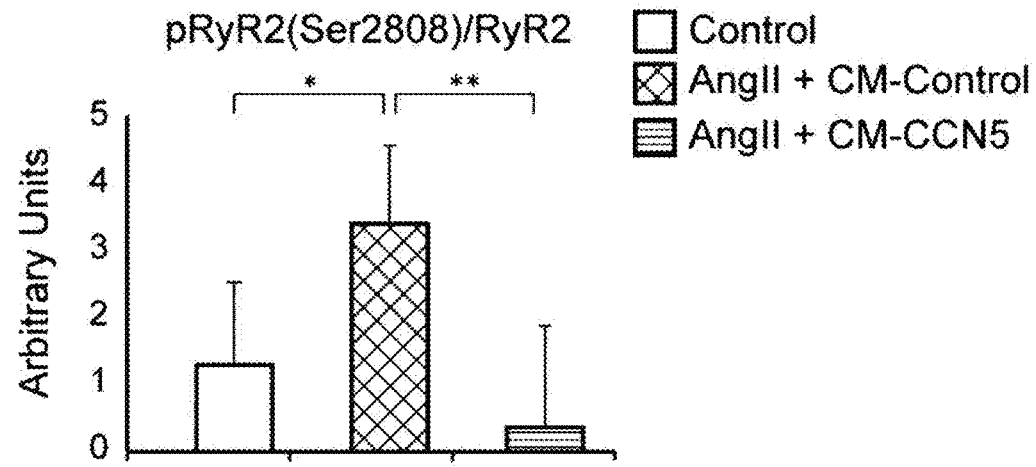
[Fig. 5e]
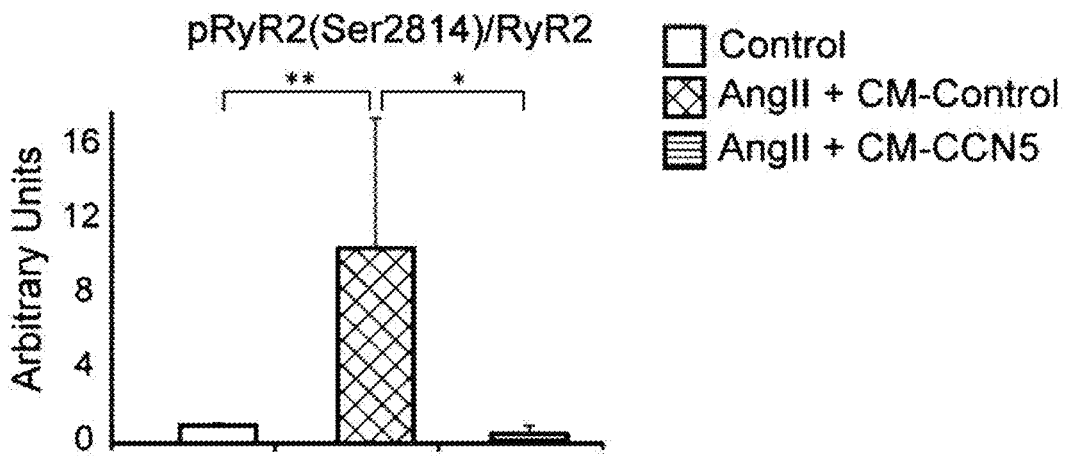
[Fig. 5f]
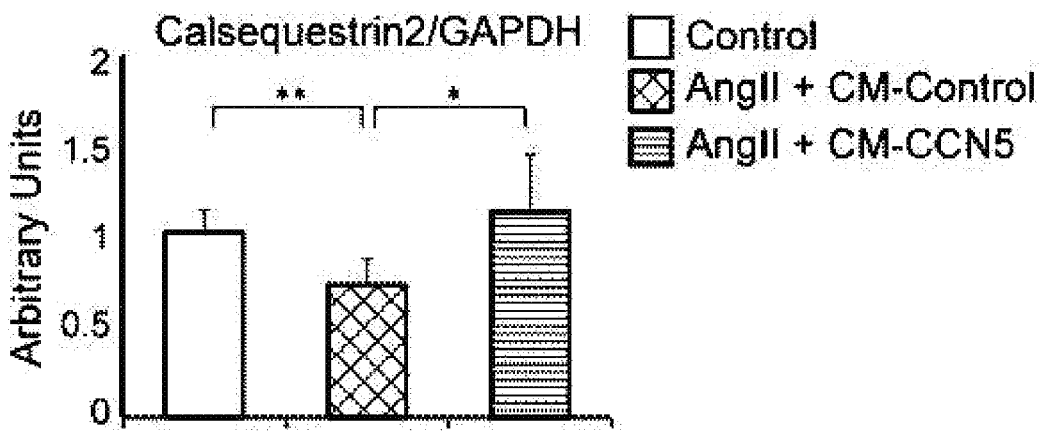

[Fig. 5g]
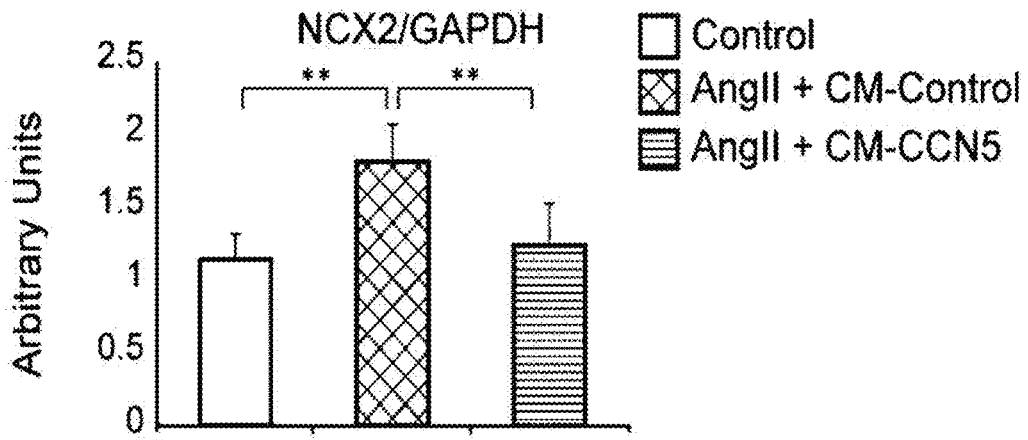
[Fig. 6a]
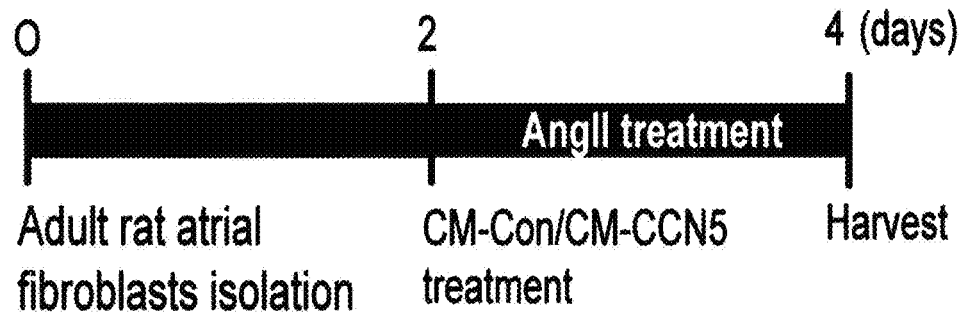
[Fig. 6b]
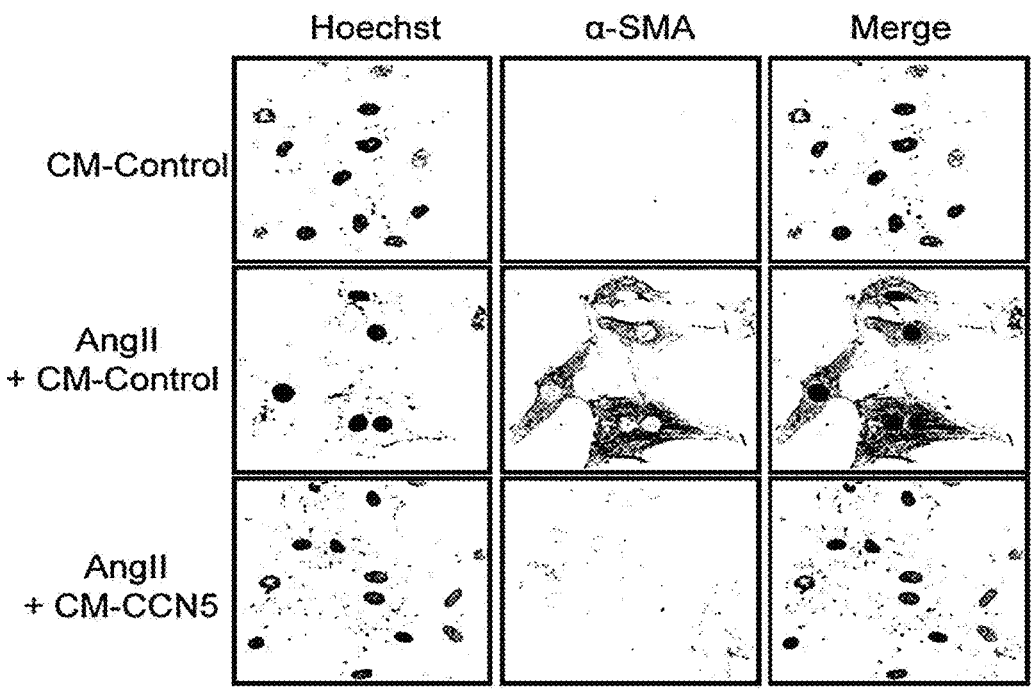

[Fig. 6c]
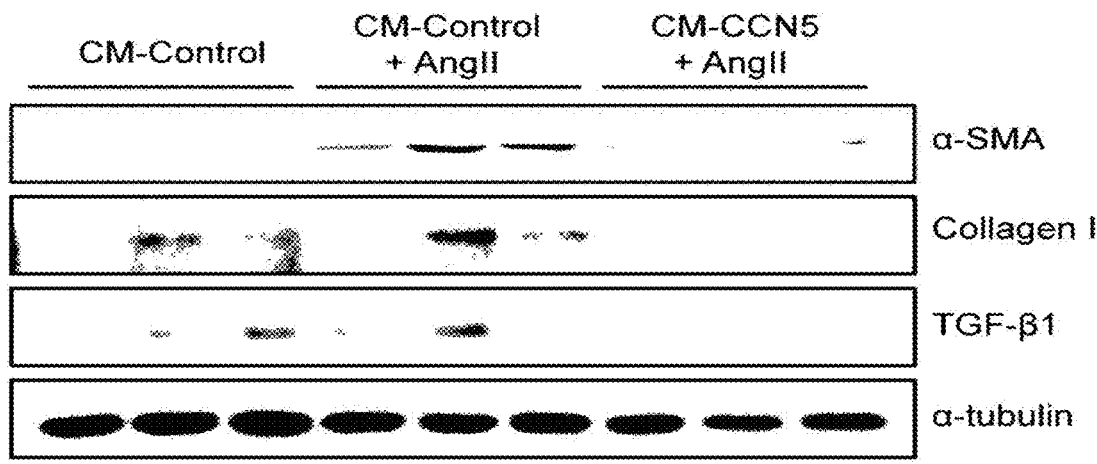
[Fig. 6d]
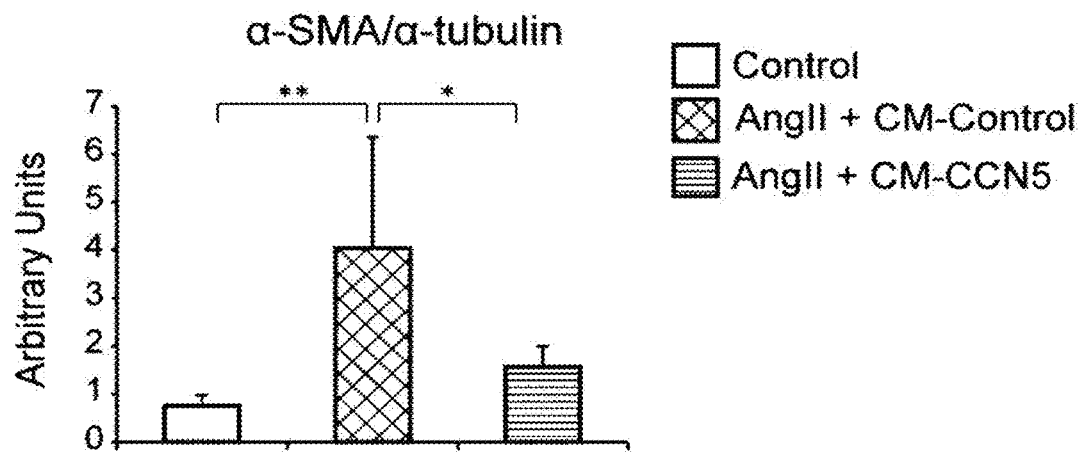
[Fig. 6e]
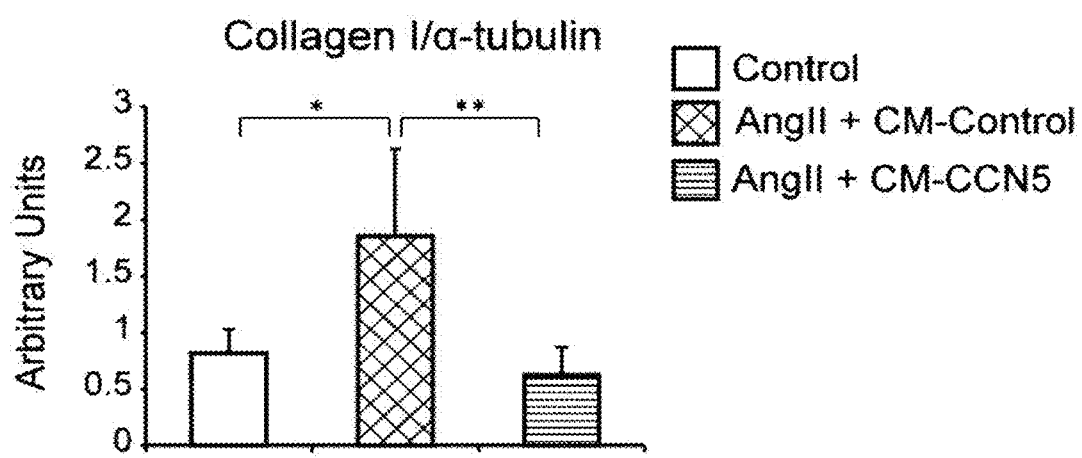

[Fig. 6f]
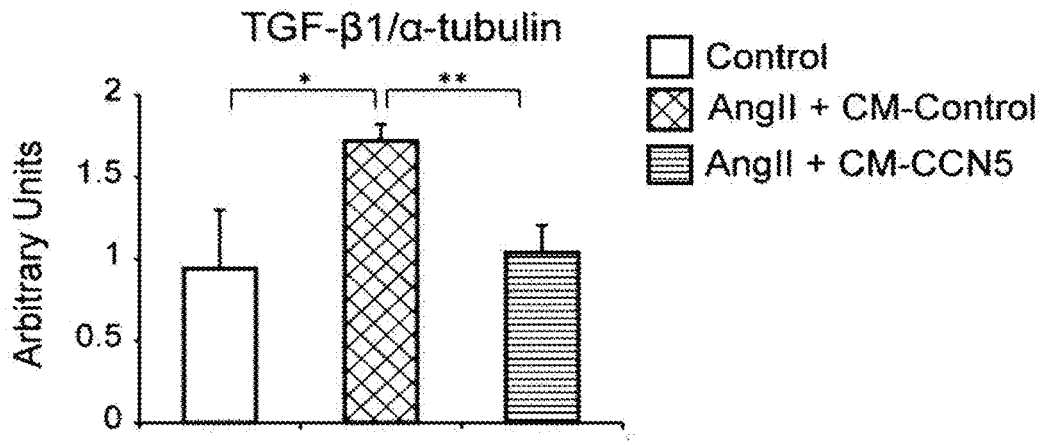
[Fig. 6g]
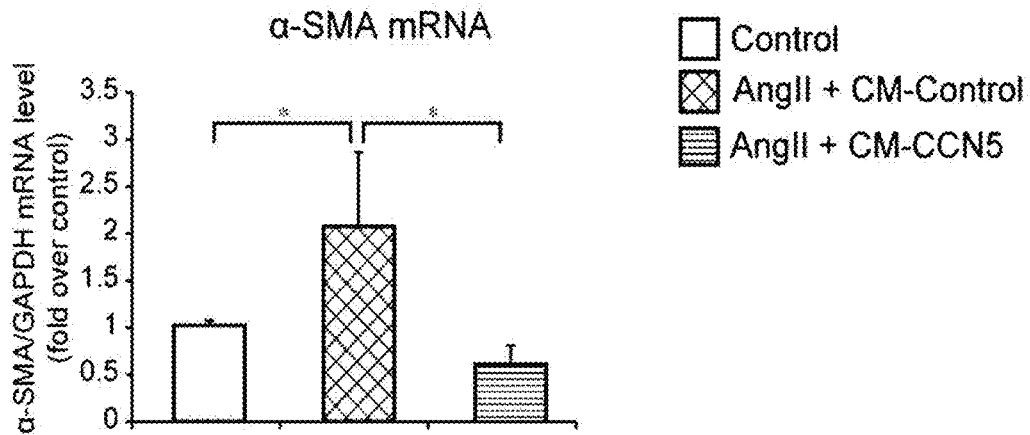
[Fig. 6h]
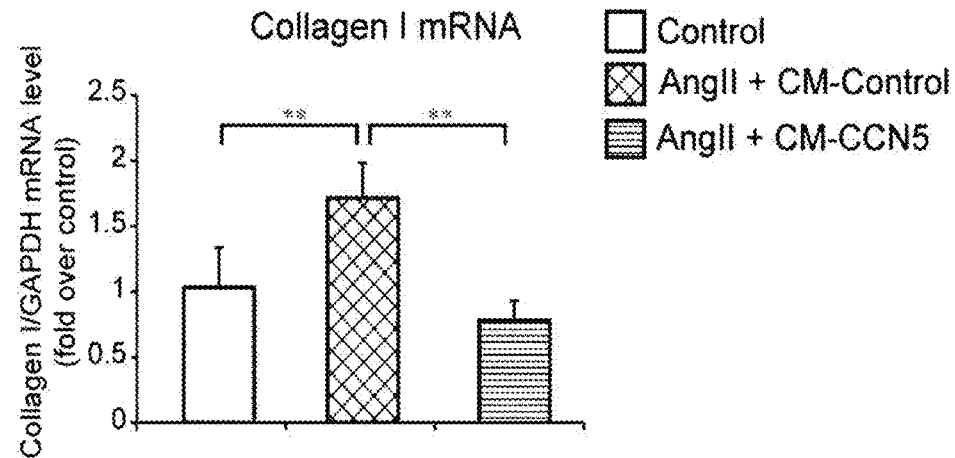

[Fig. 6i]
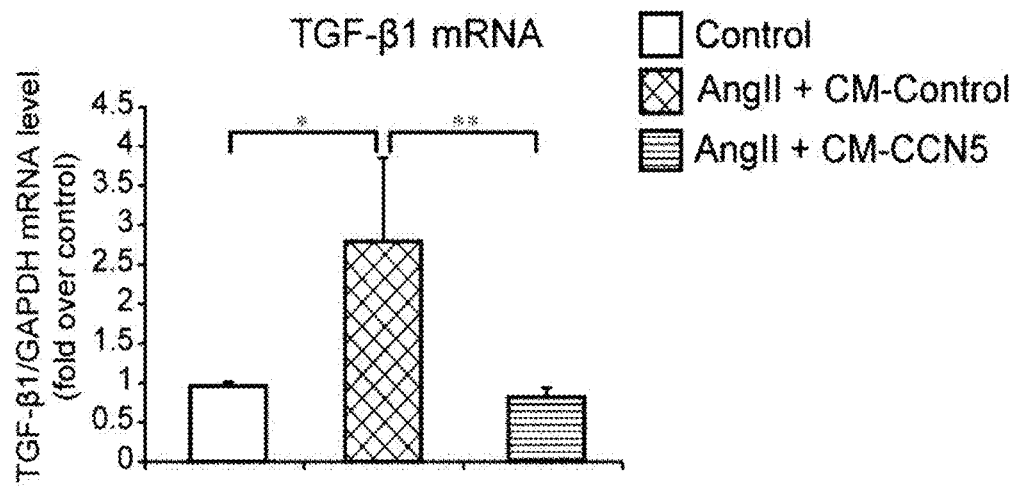
[Fig. 7a]
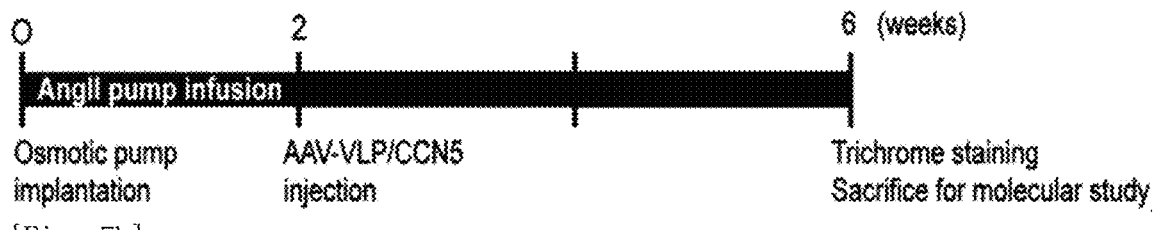
[Fig. 7b]
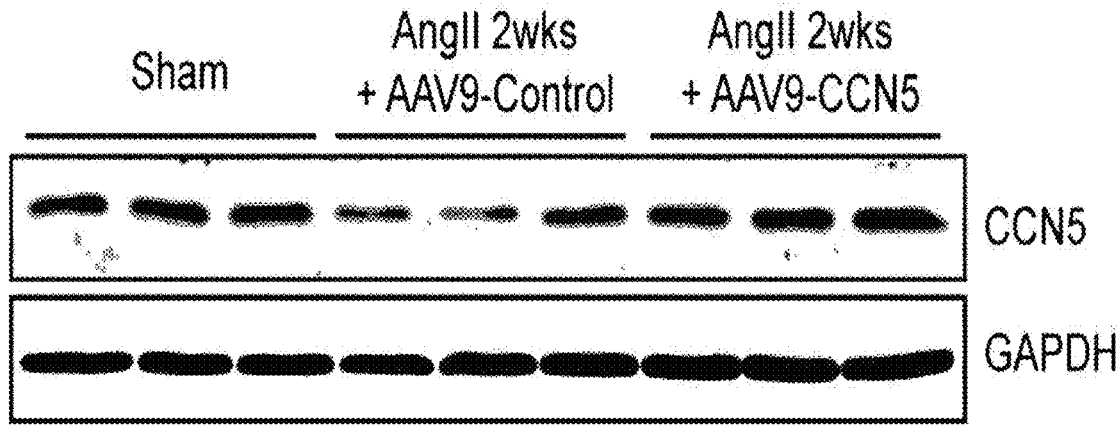

[Fig. 7c]
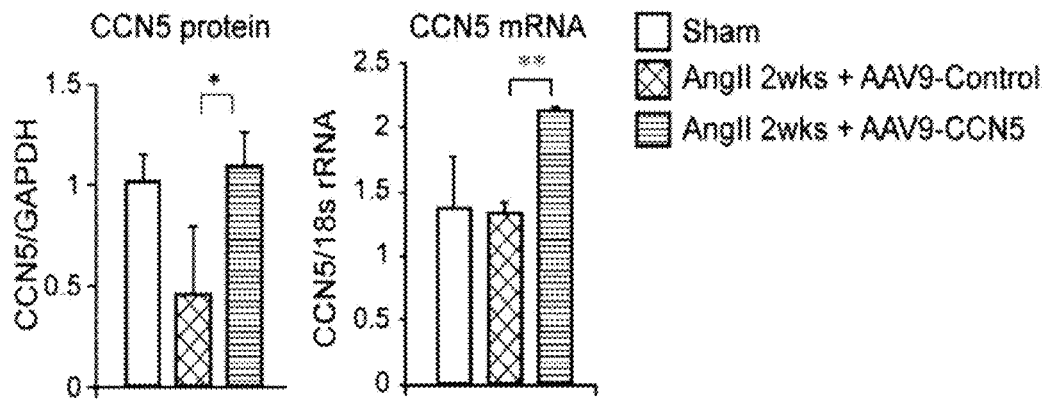
[Fig. 7d]
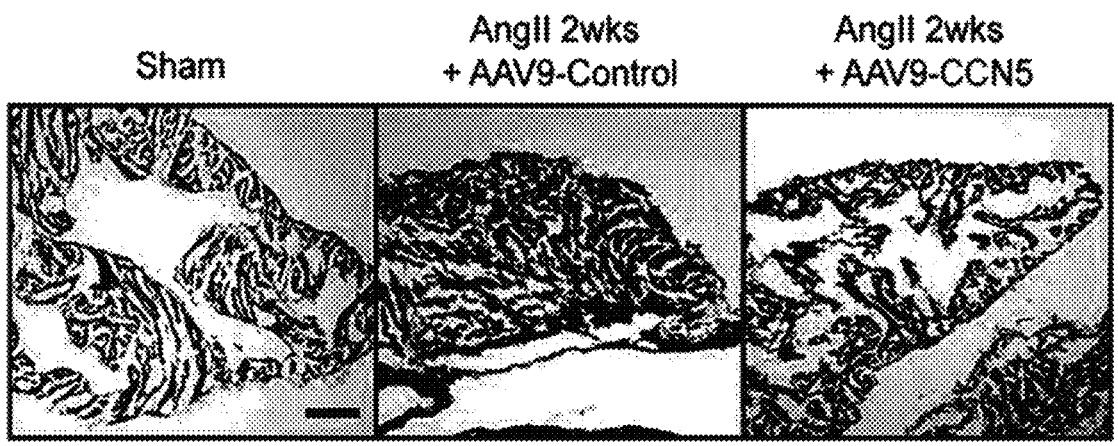
[Fig. 7e]
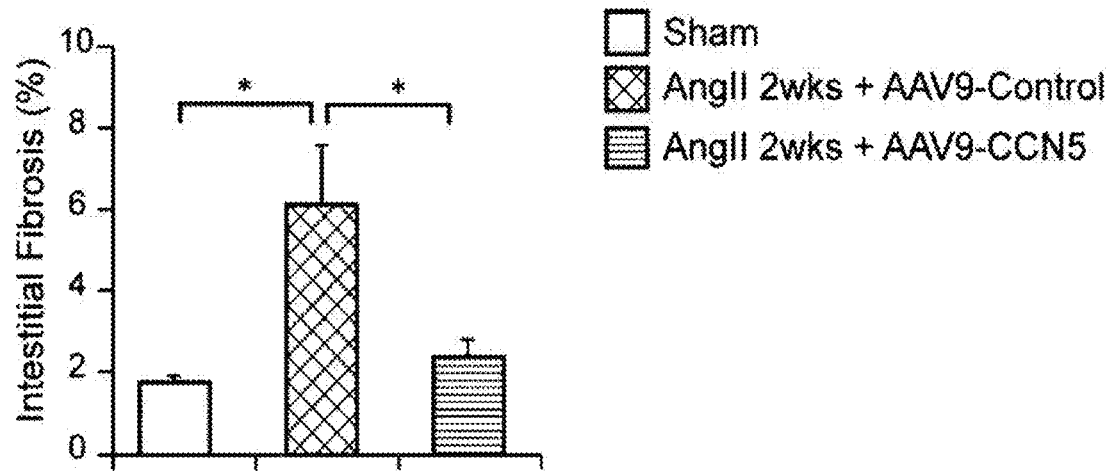

[Fig. 7f]
[Fig. 7g]
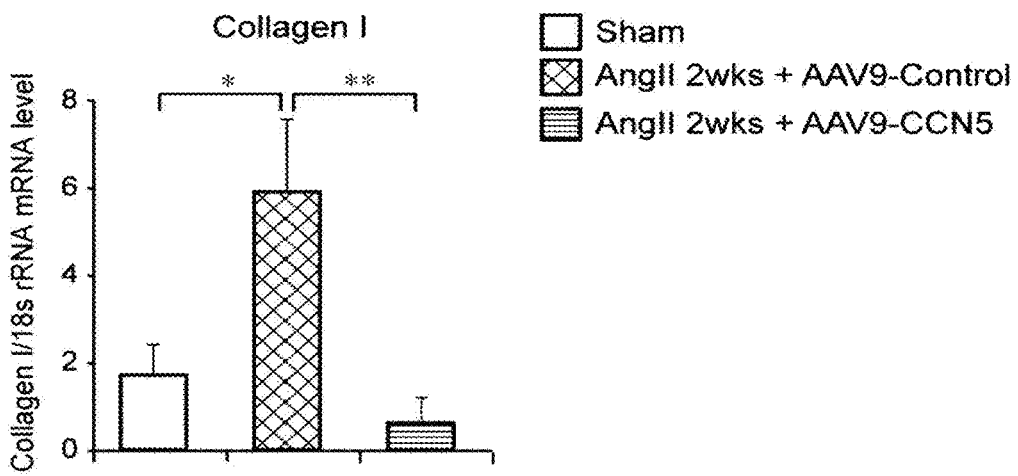
[Fig. 7h]
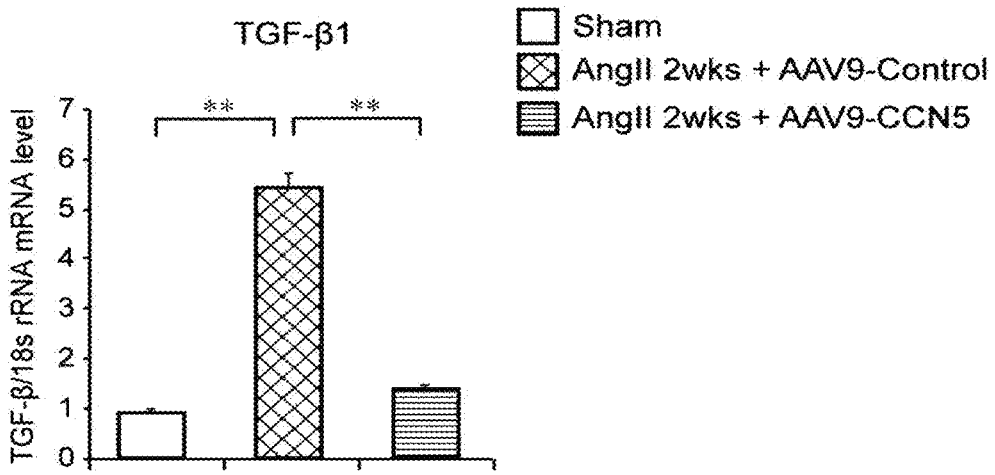

[Fig. 7i]
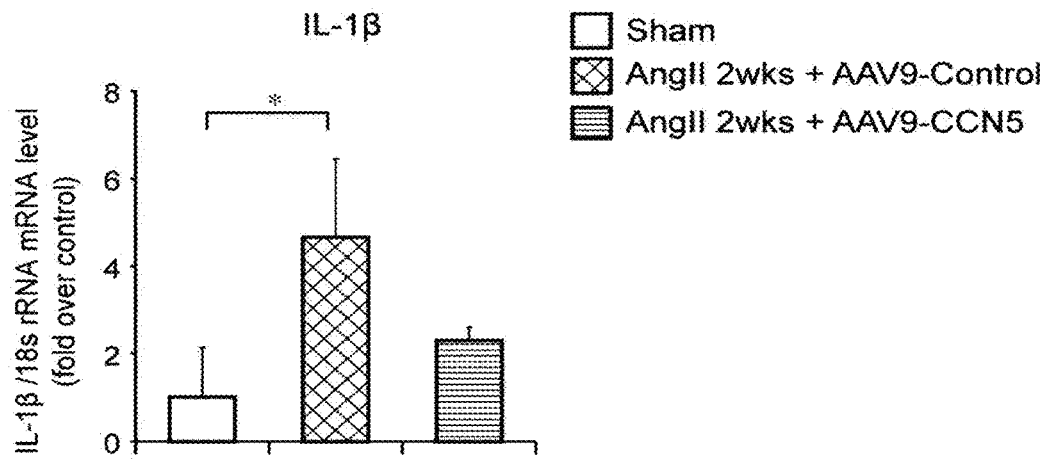
[Fig. 7j]
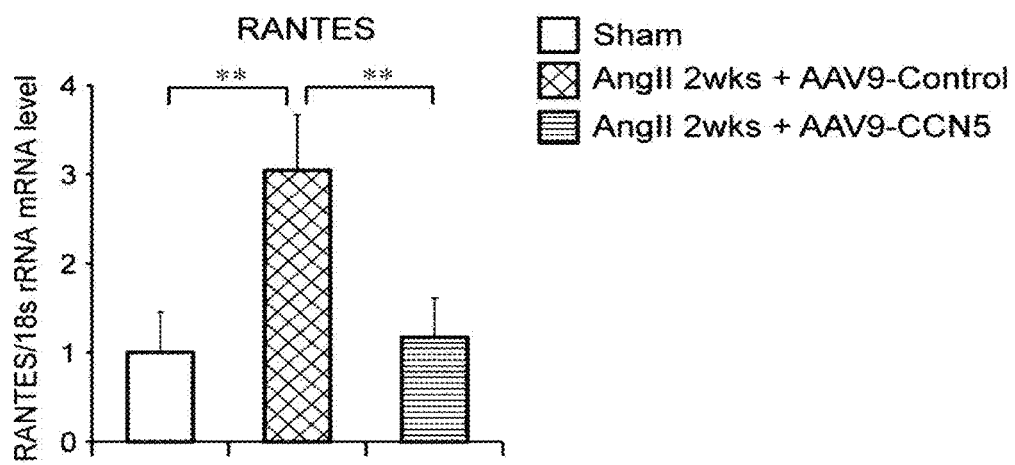
[Fig. 7k]

[Fig. 7l]
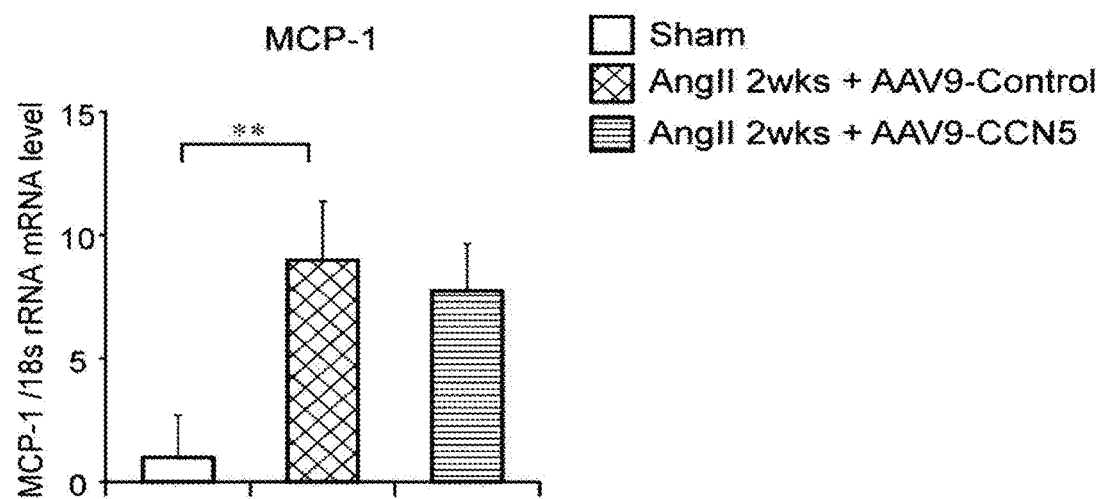
[Fig. 8a]
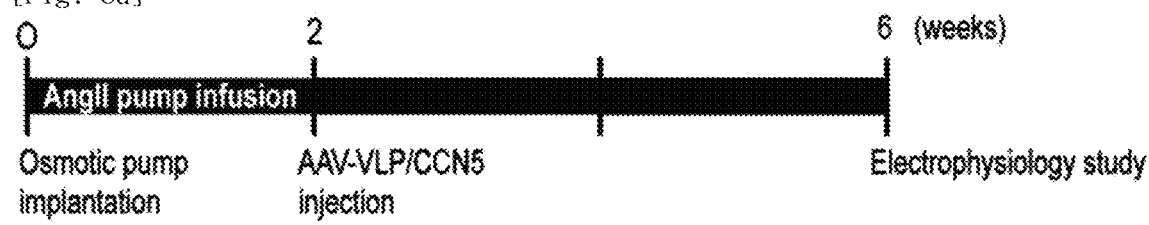

[Fig. 8b]
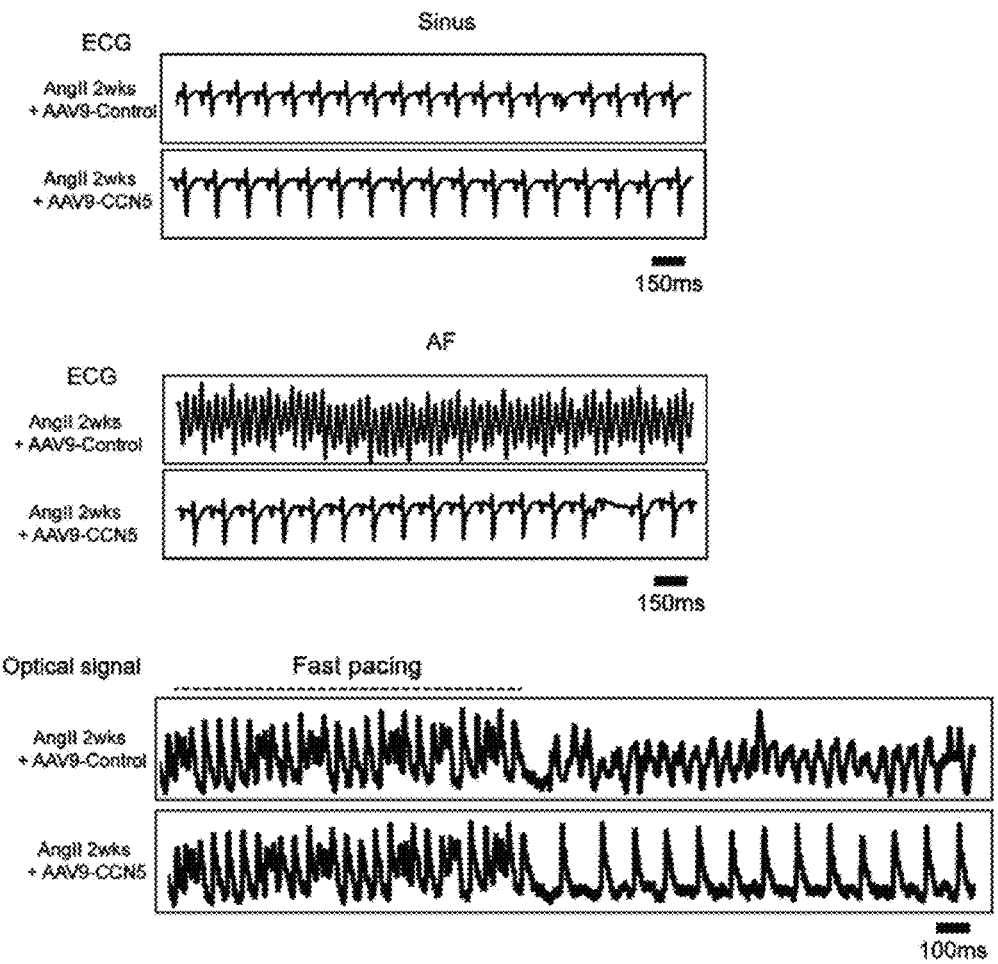
[Fig. 8c]
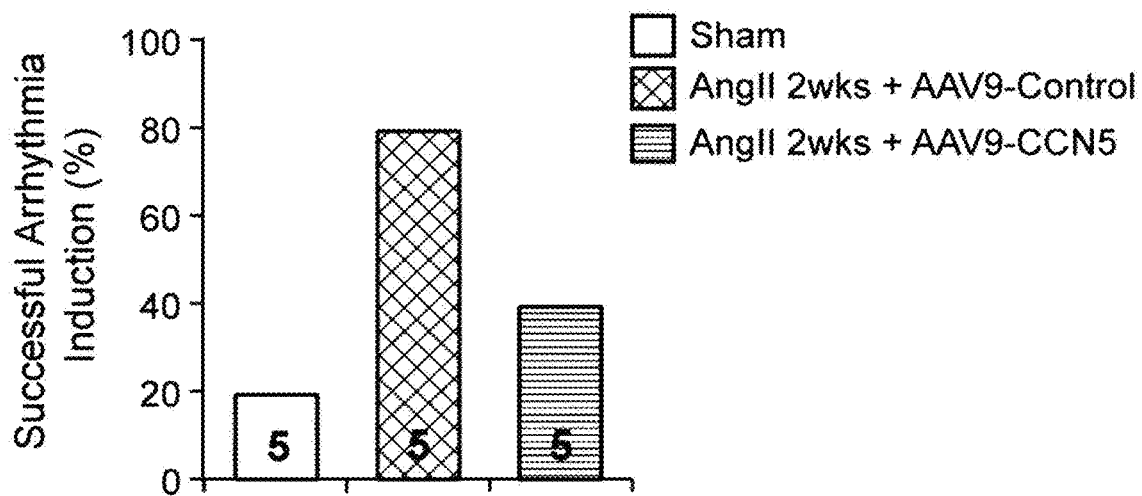

[Fig. 8d]
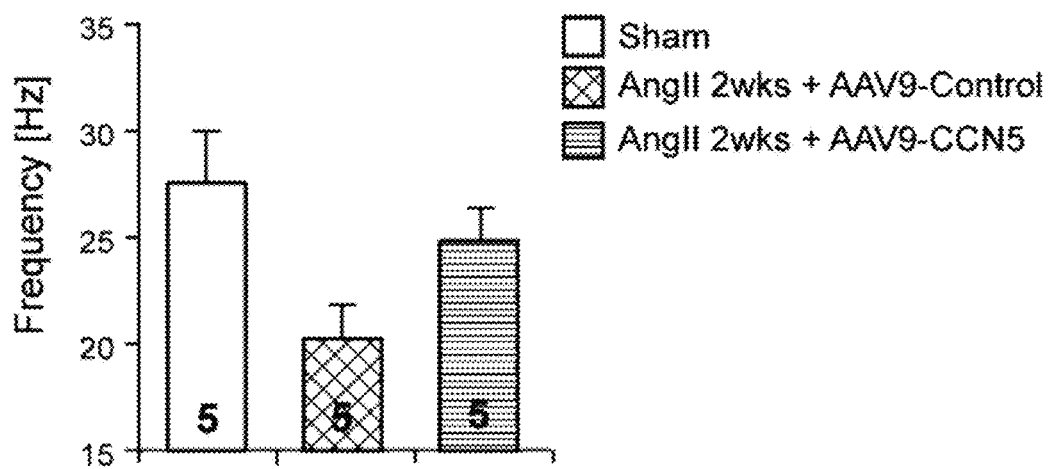

[Fig. 8e]
X-axis: time (unit: ms)
Y-axis: potential (unit: mV)
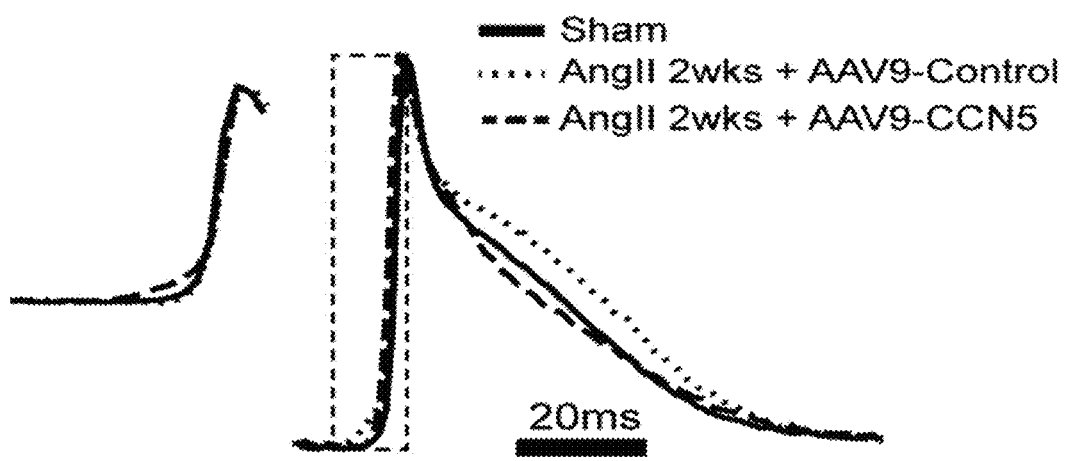

[Fig. 8f]
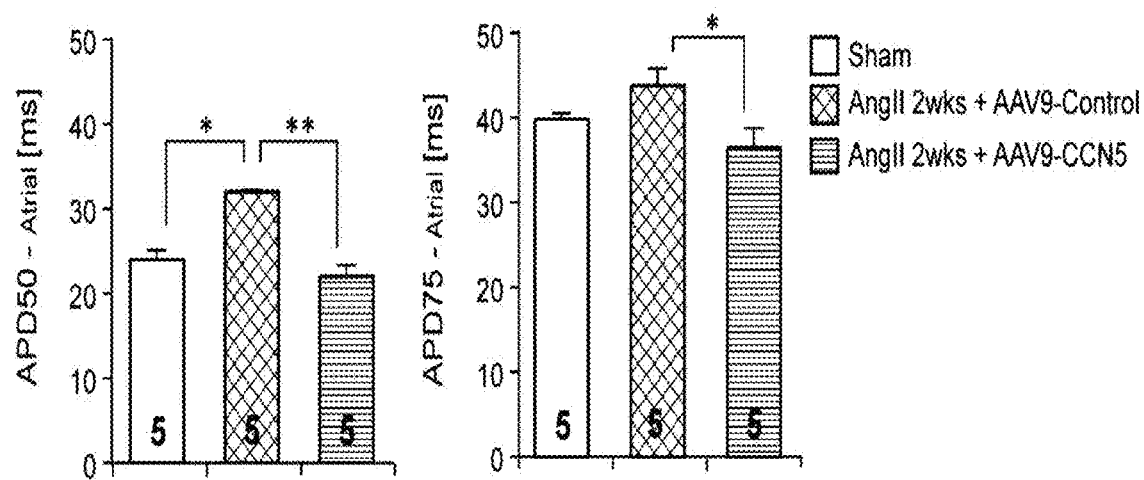

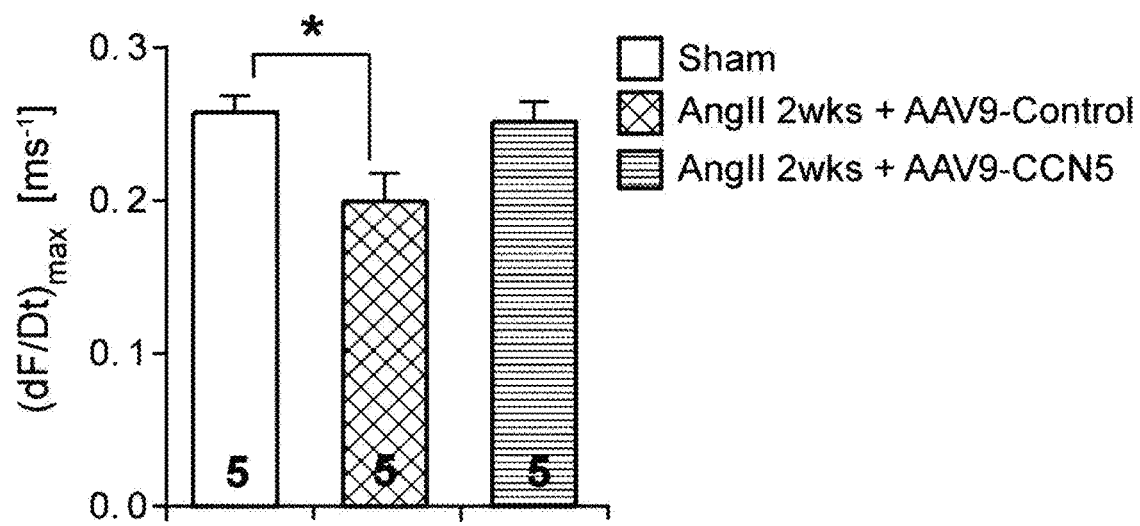
[Fig. 8g]

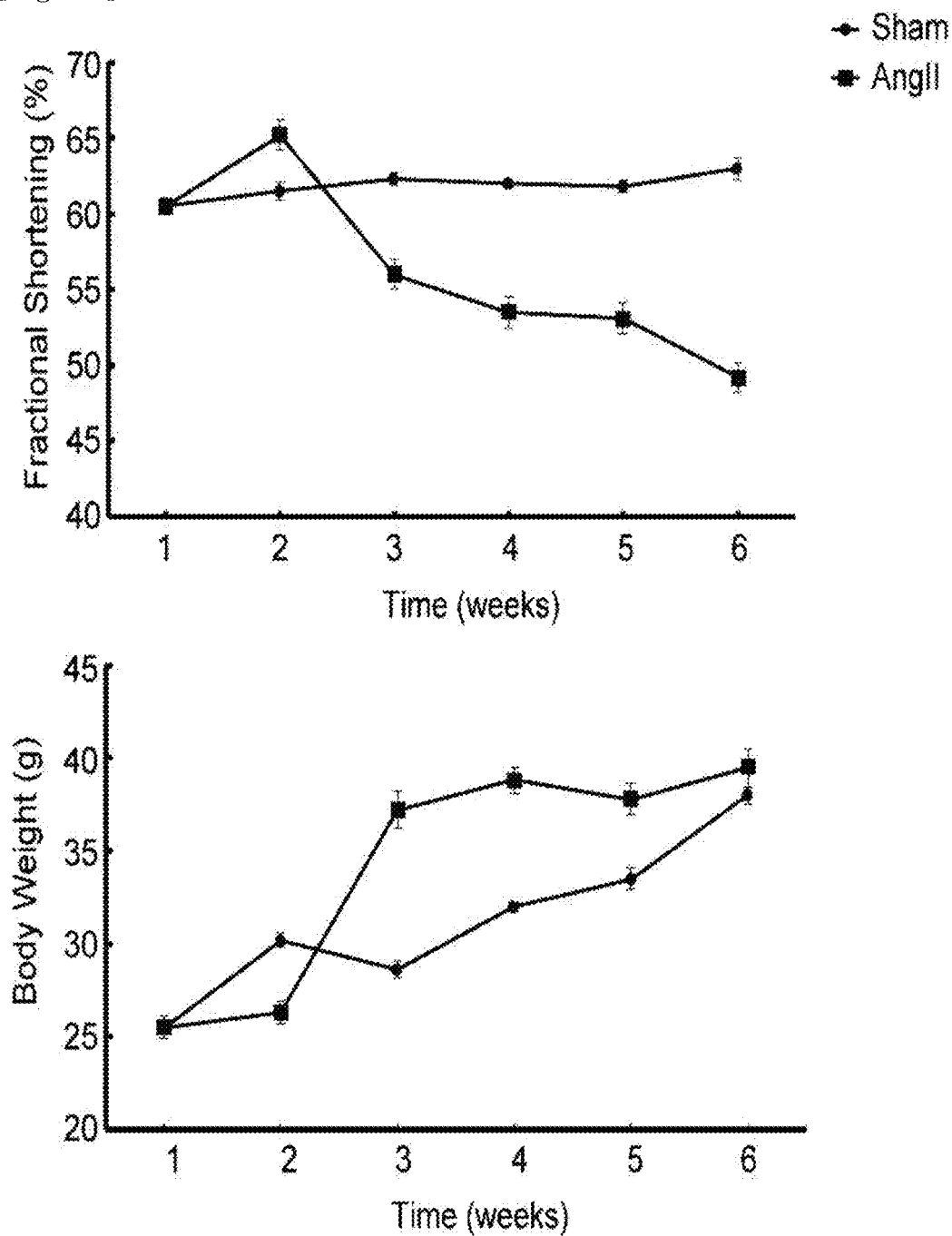
[Fig. 9a]

[Fig. 9b]
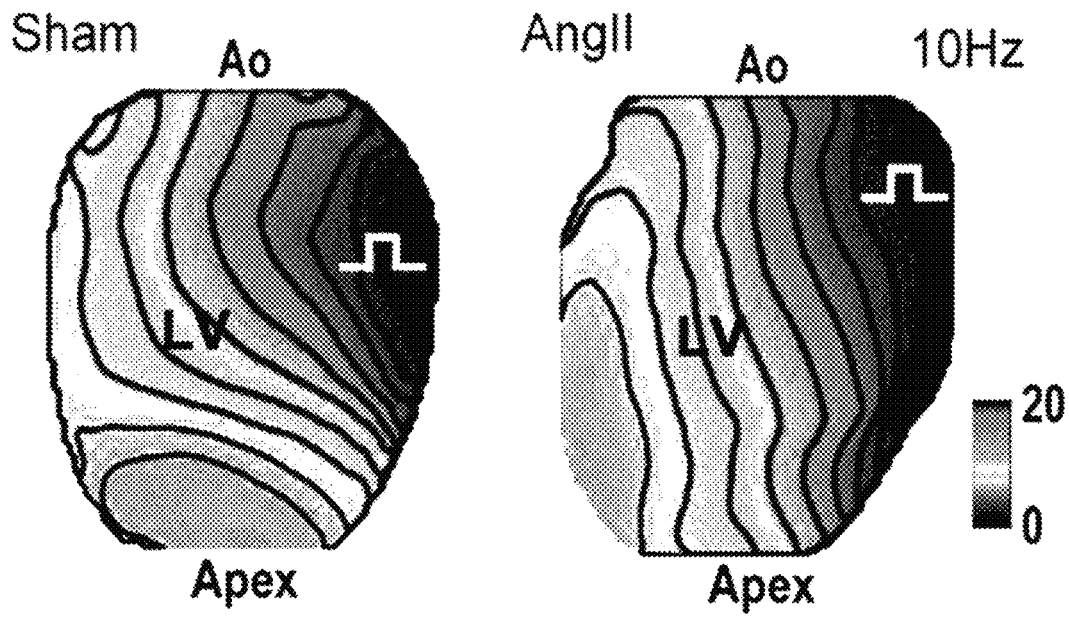
[Fig. 9c]
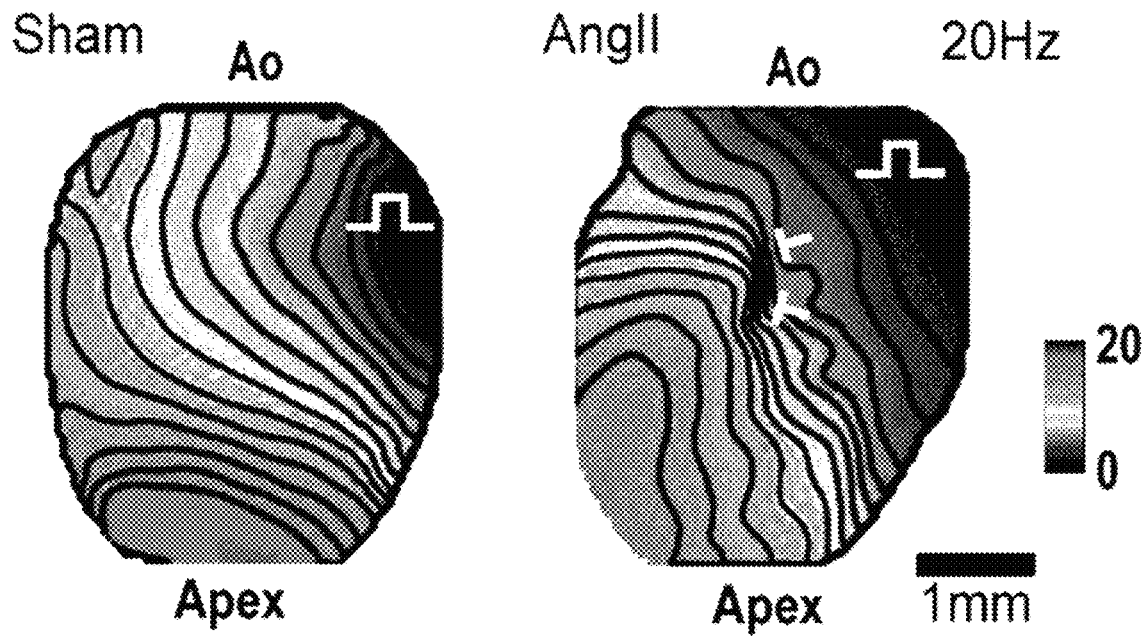

[Fig. 9d]
X-axis: time (unit: ms)
Y-axis: potential (unit: mV)
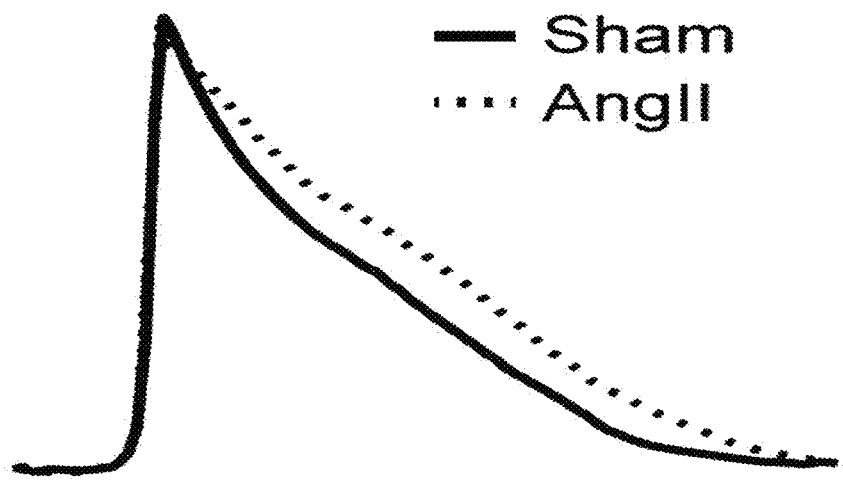

[Fig. 9e]
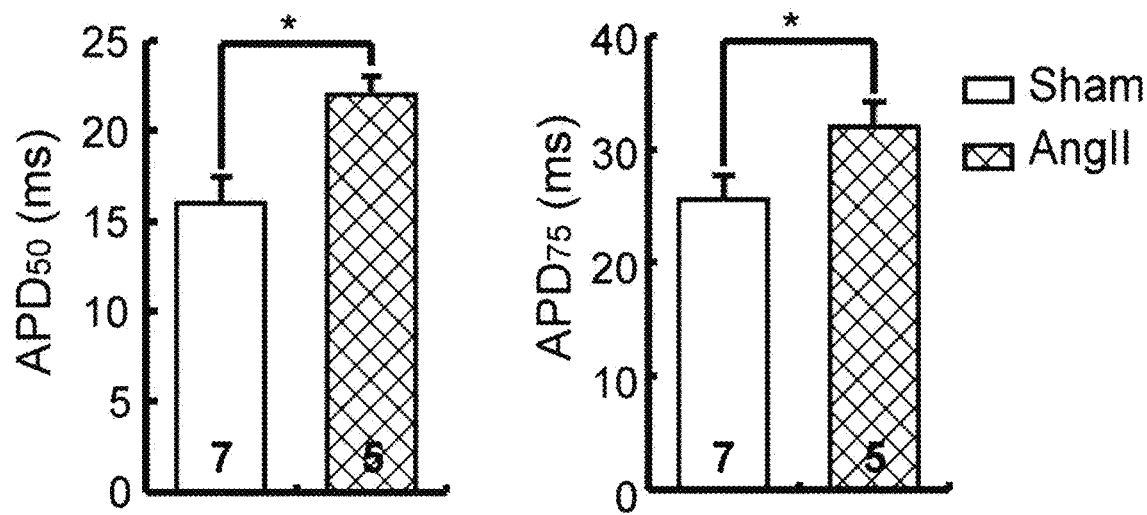

[Fig. 9f]
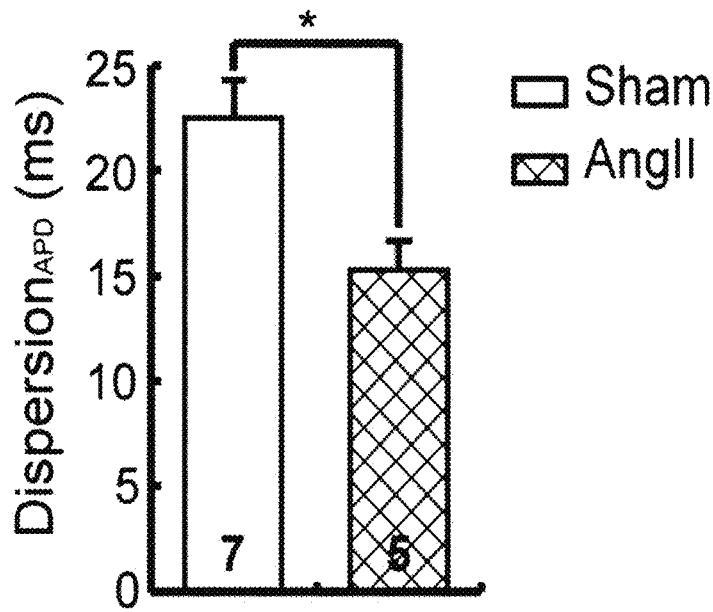
[Fig. 9g]
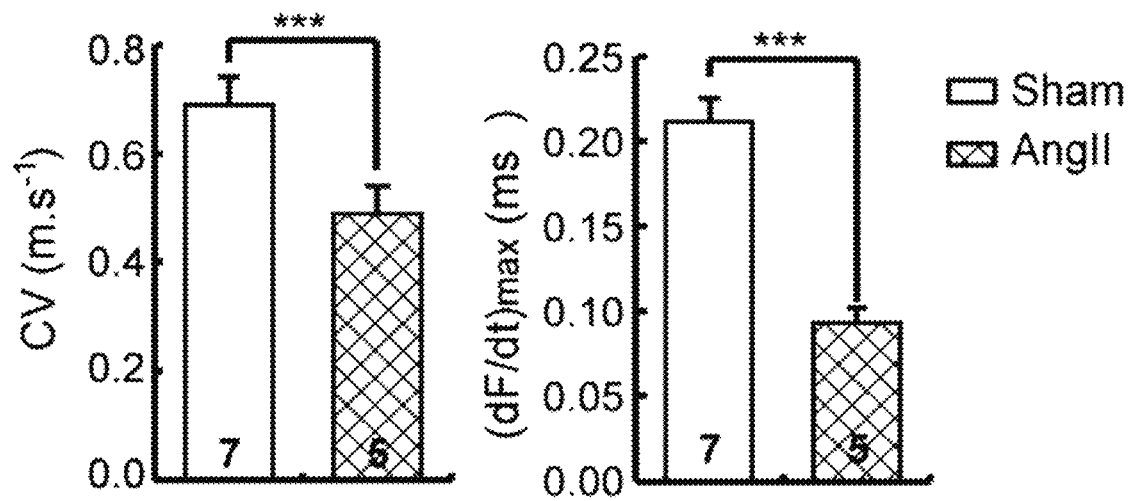

[Fig. 10a]
X-axis: time (unit: ms)
Y-axis: potential (unit: mV)
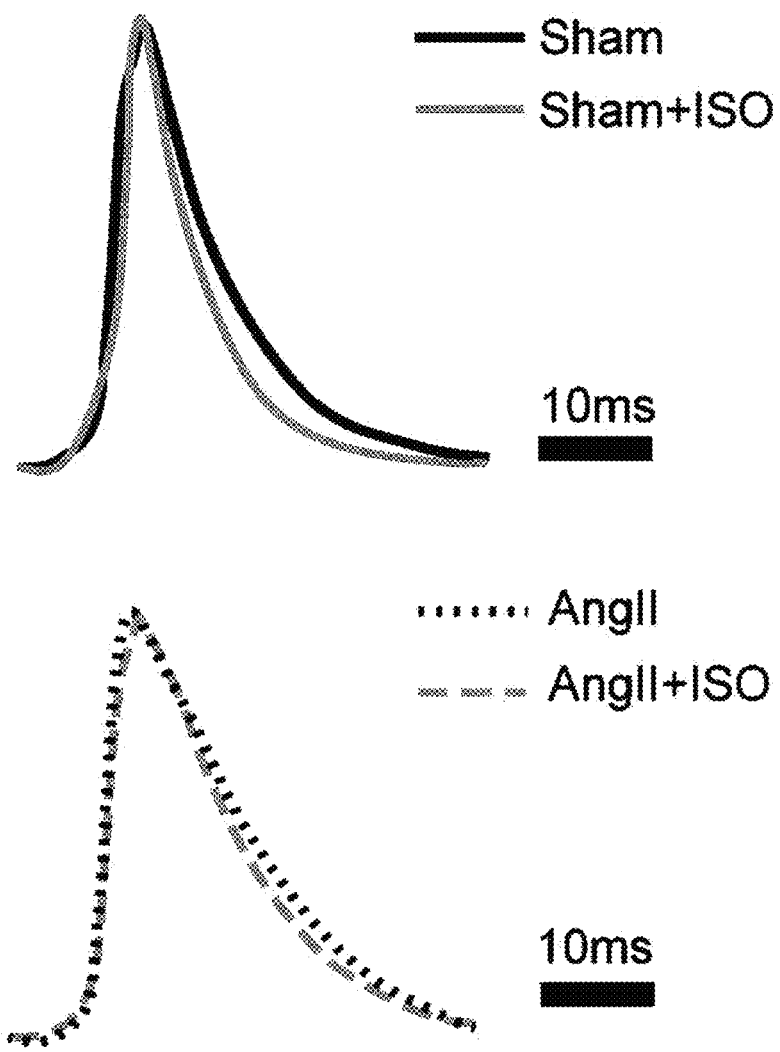

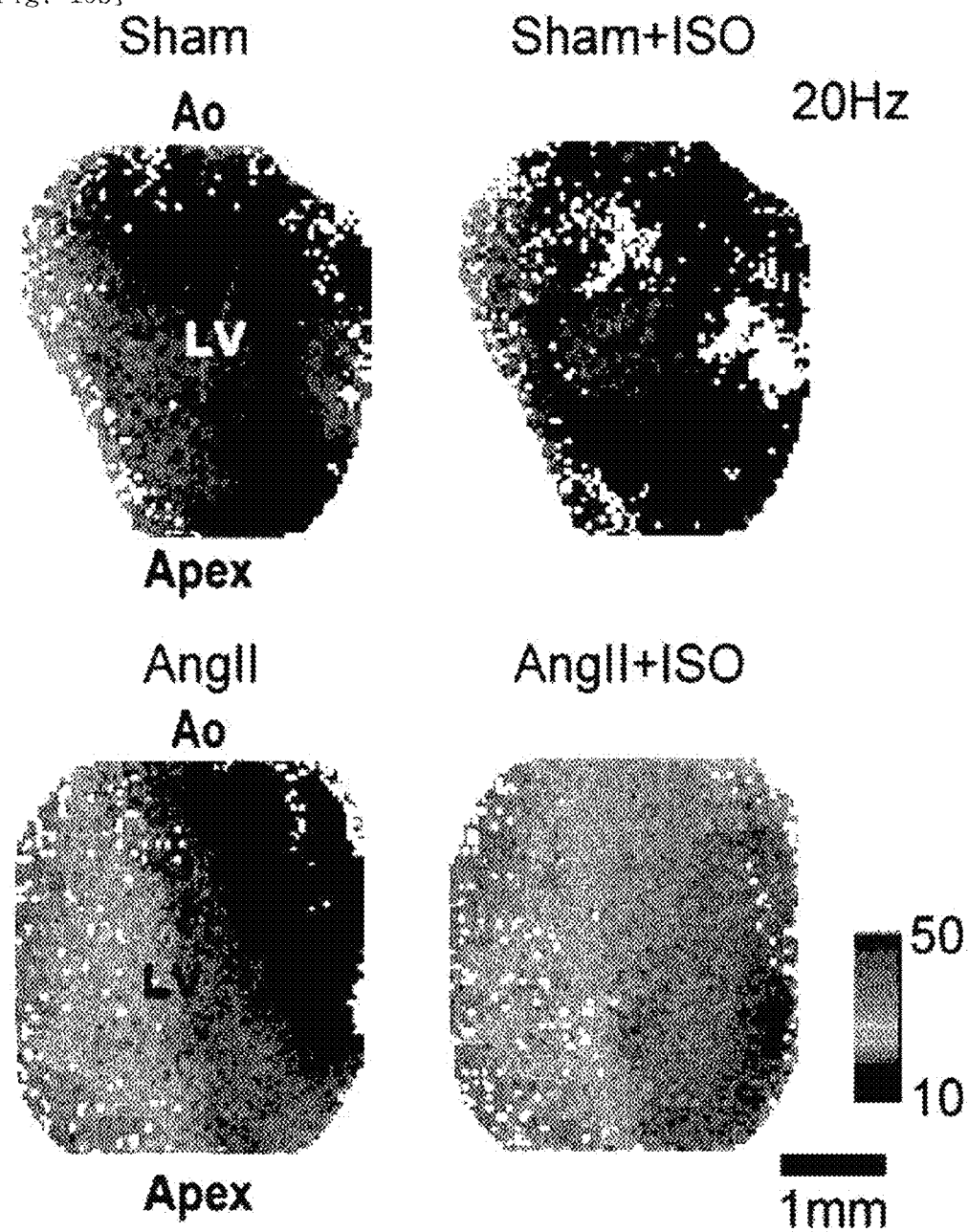
[Fig. 10b]

[Fig. 10c]
X-axis: time (unit: ms)
Y-axis: umber of counts
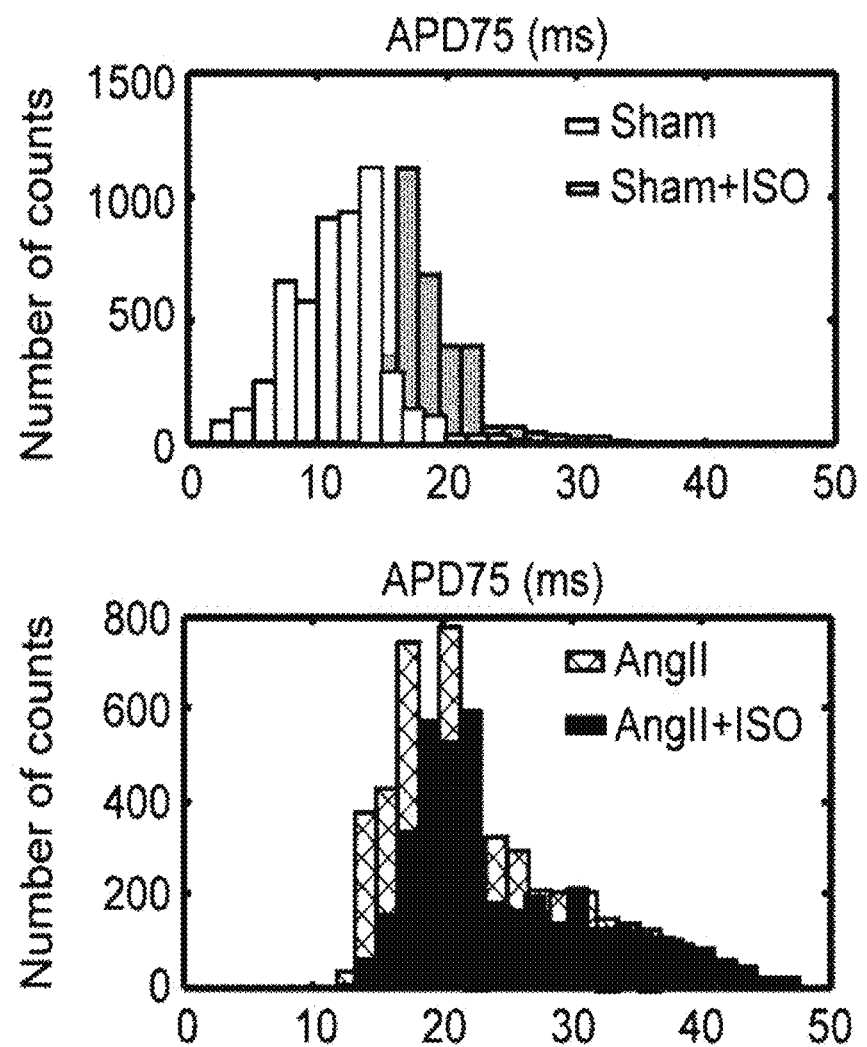

[Fig. 10d]
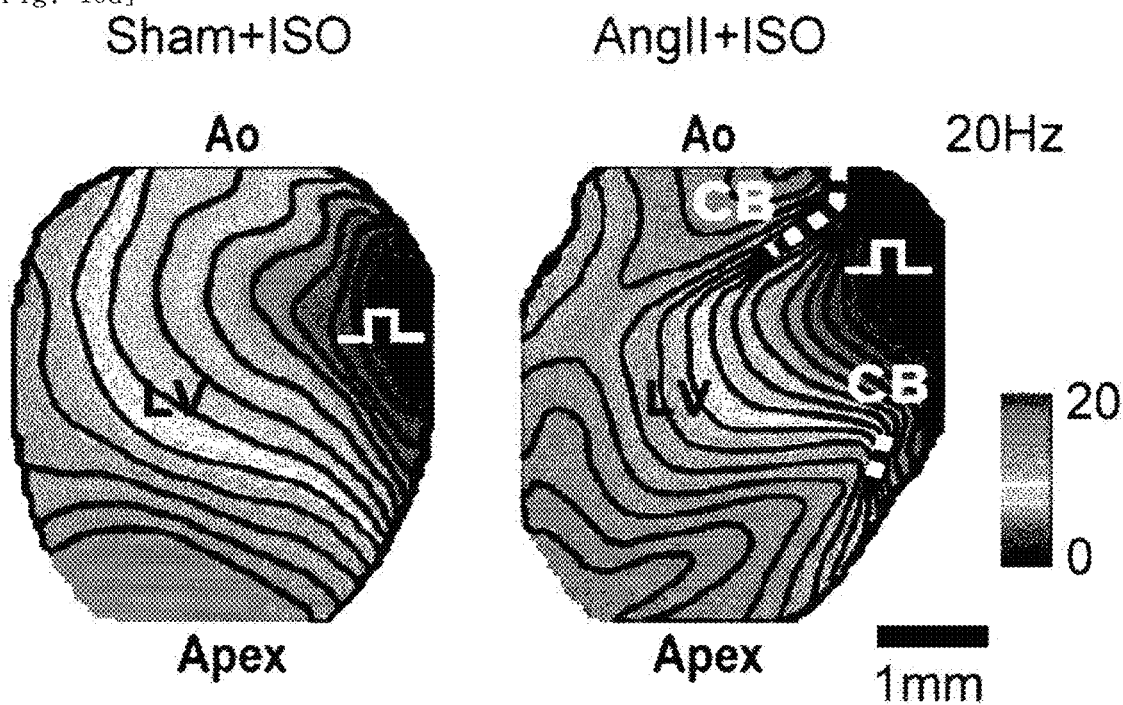
[Fig. 10e]
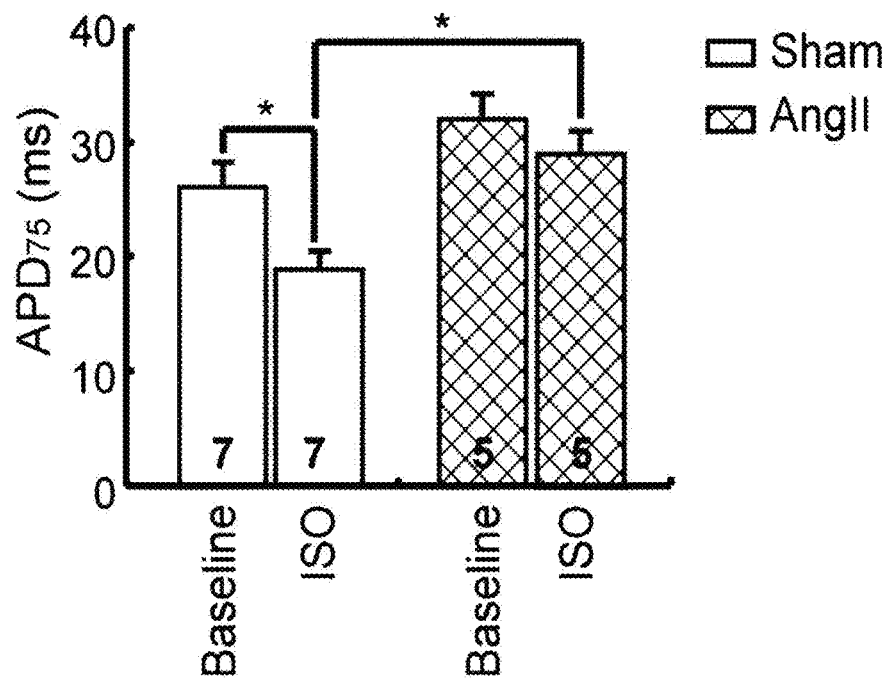

[Fig. 10f]
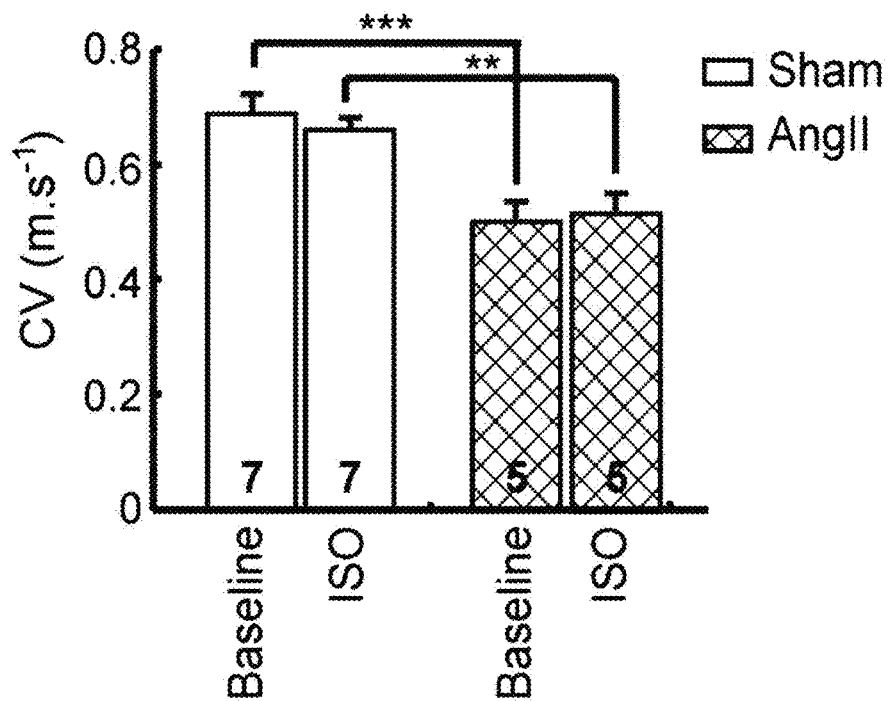
[Fig. 11a]
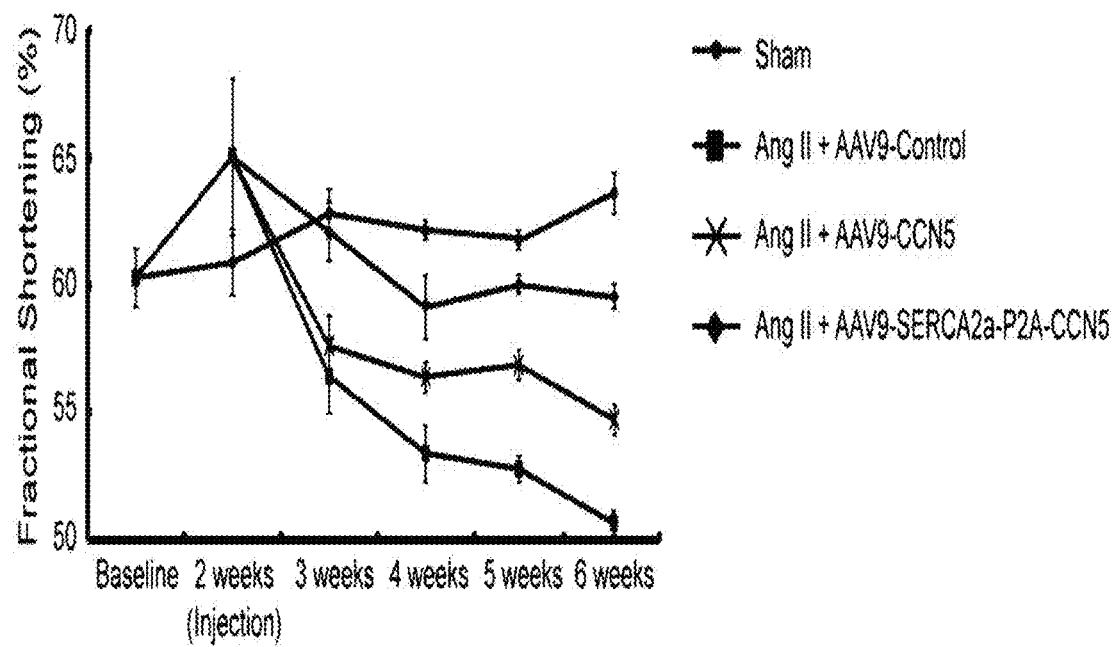

[Fig. 11b]
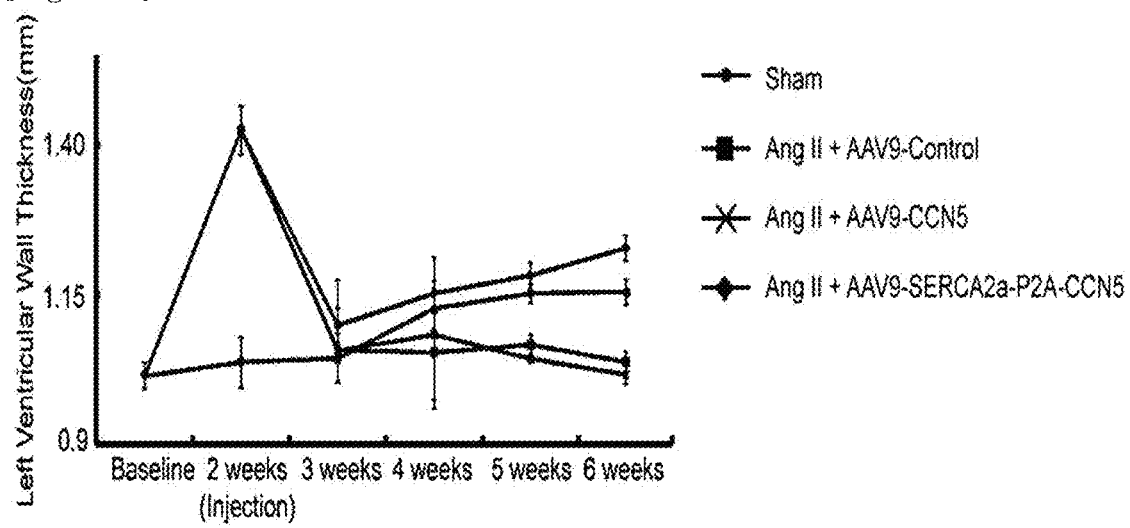
[Fig. 11c]
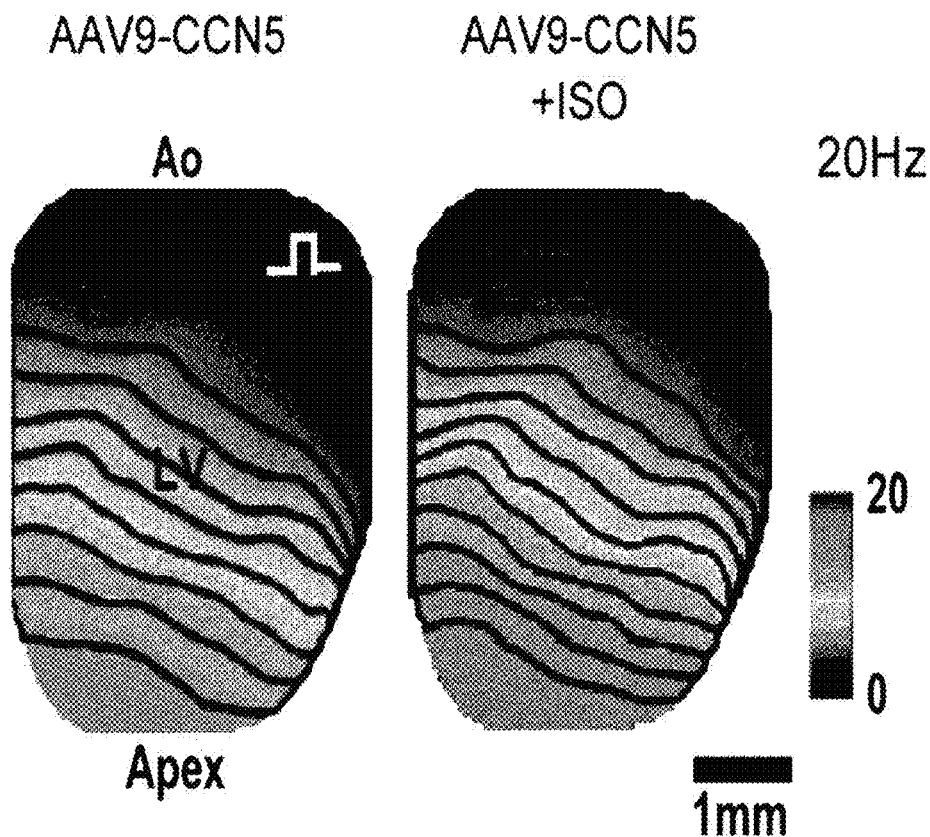

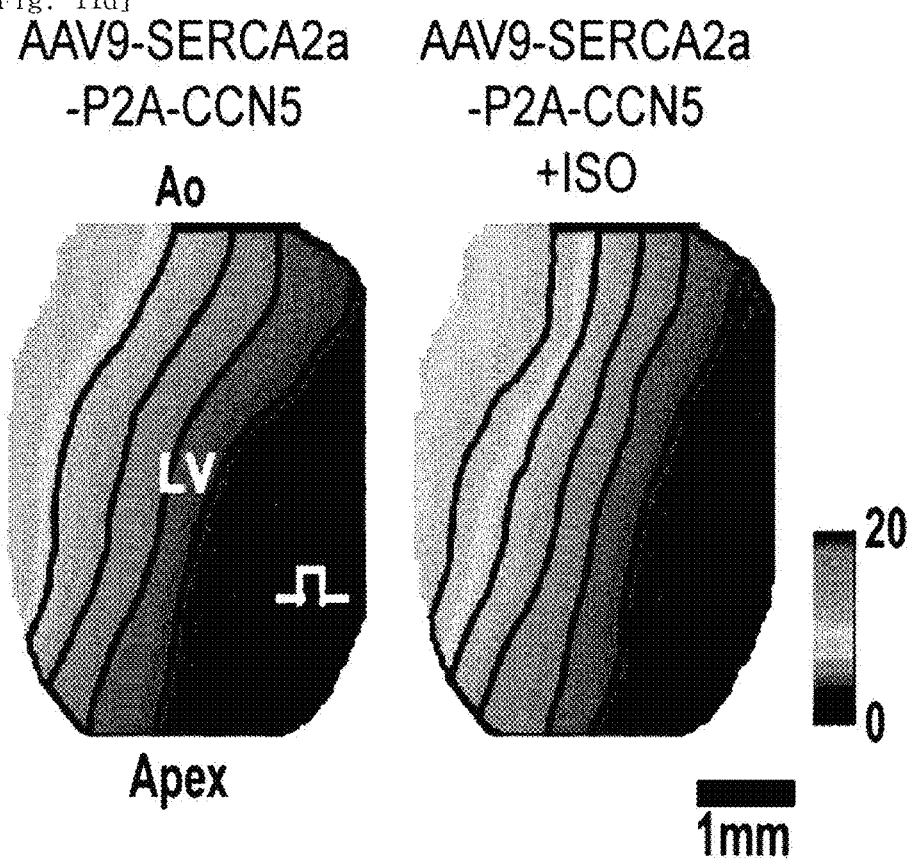

[Fig. 11e]
X-axis: time (unit: ms)
Y-axis: potential (unit: mV)
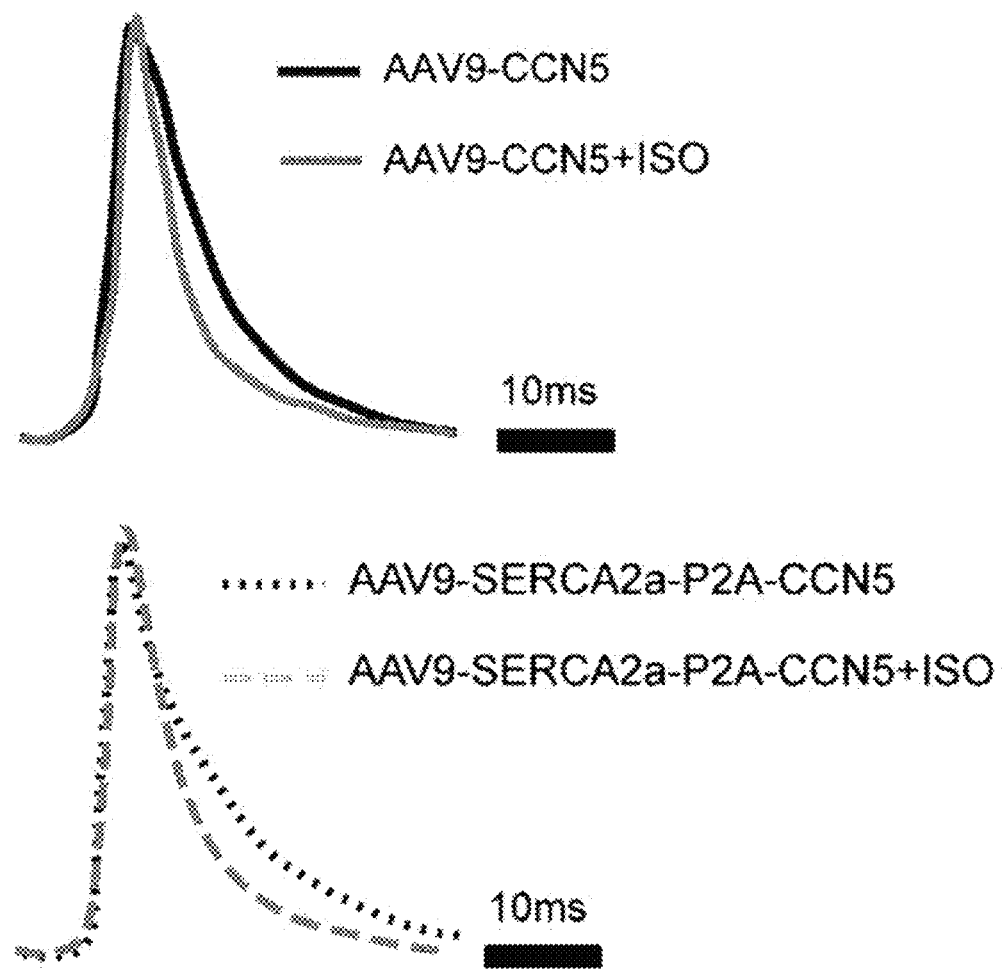

[Fig. 11f]
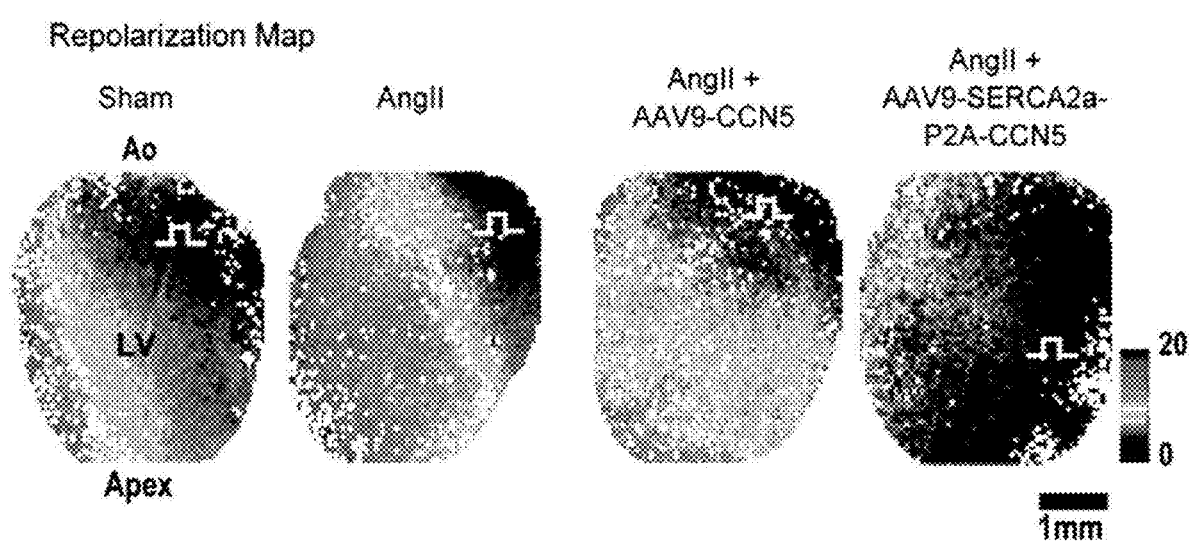

[Fig. 11g]
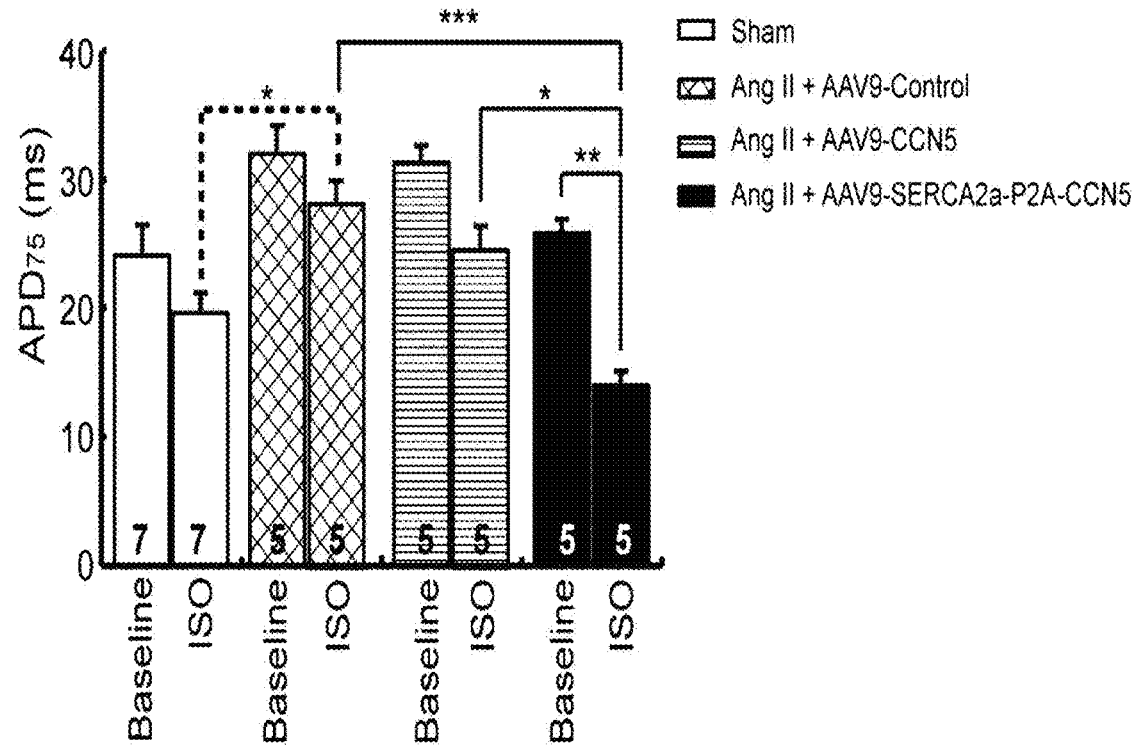
[Fig. 11h]
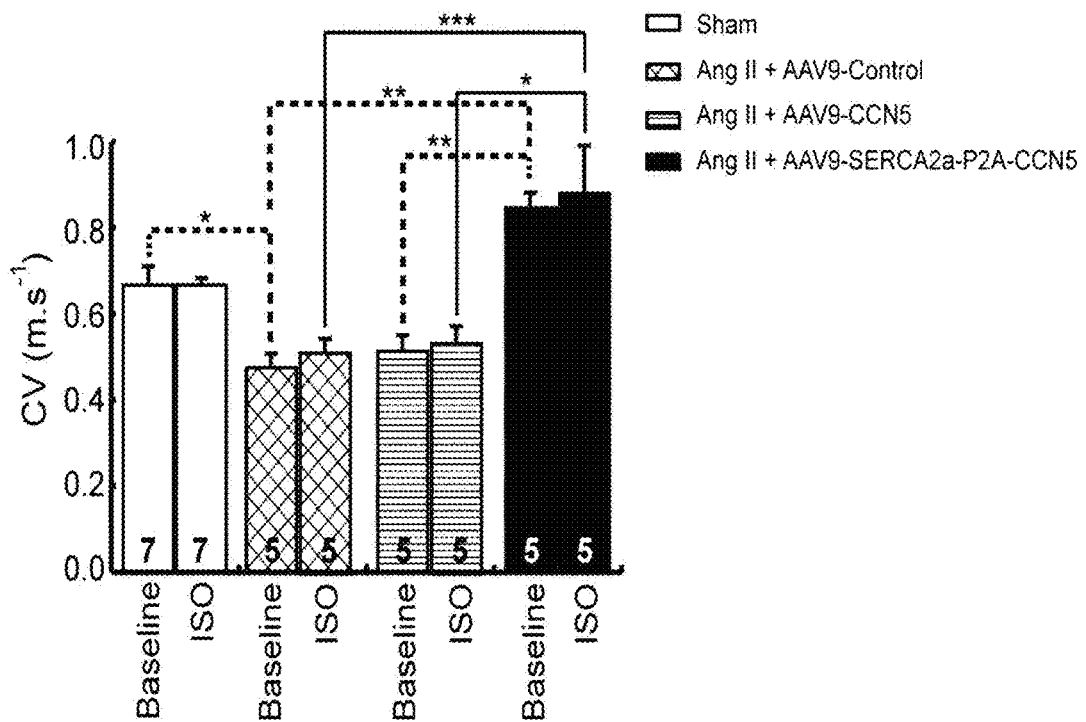

[Fig. 11i]
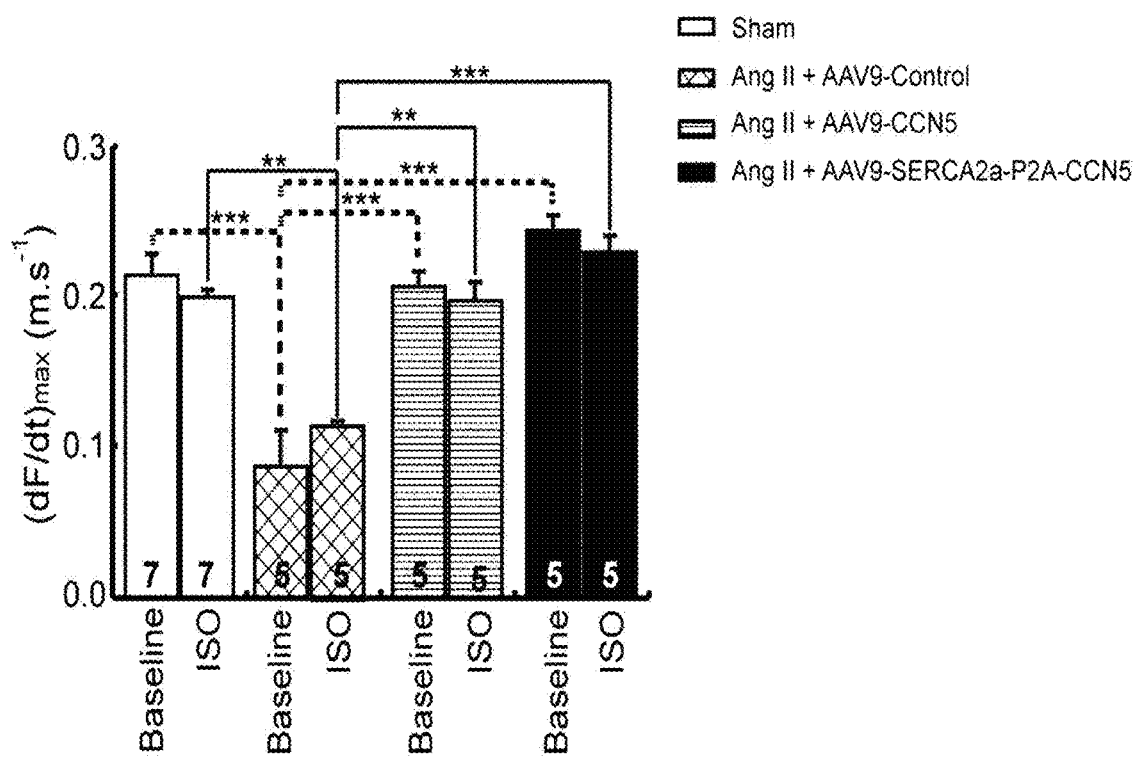

[Fig. 12a]
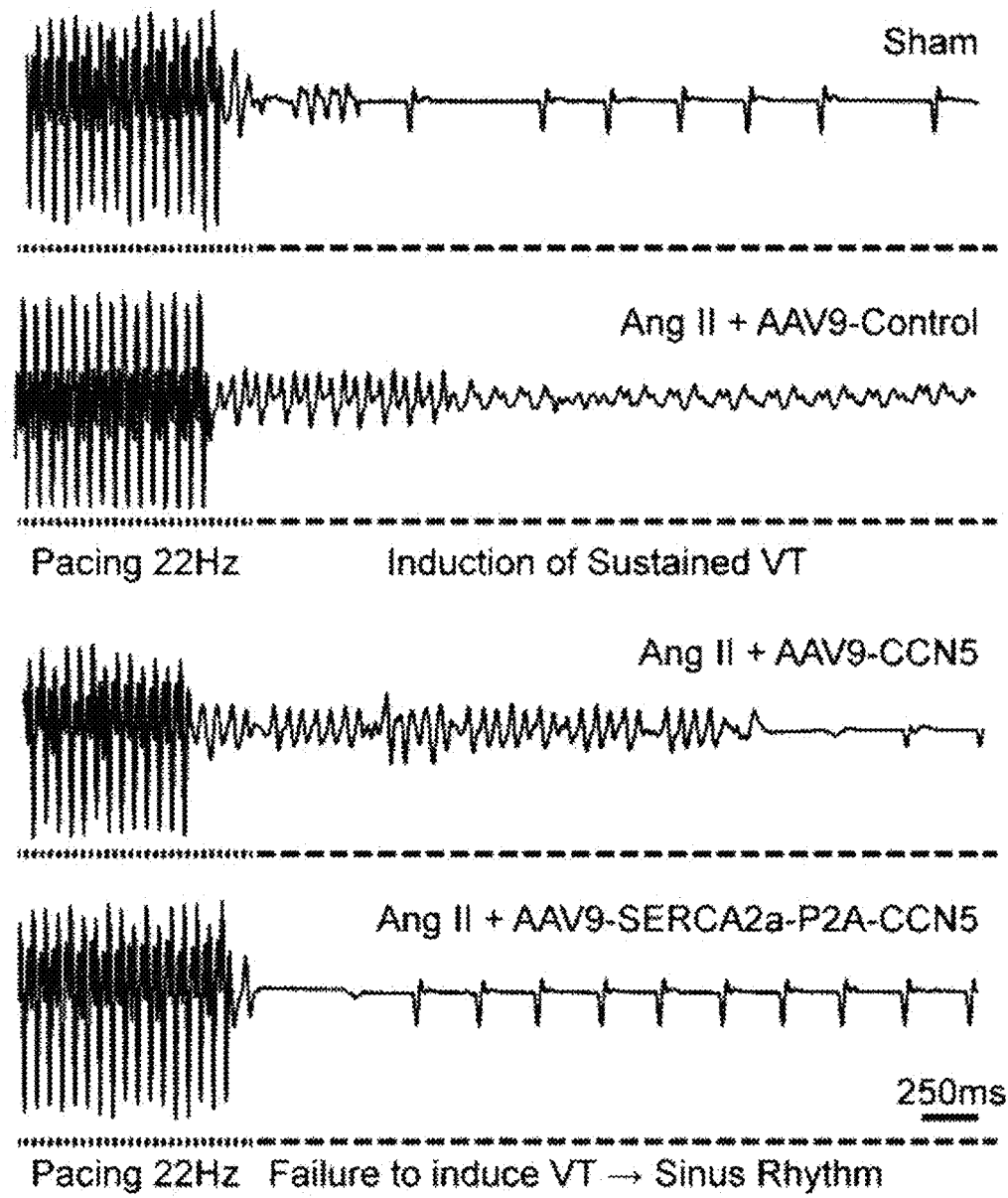

[Fig. 12b]
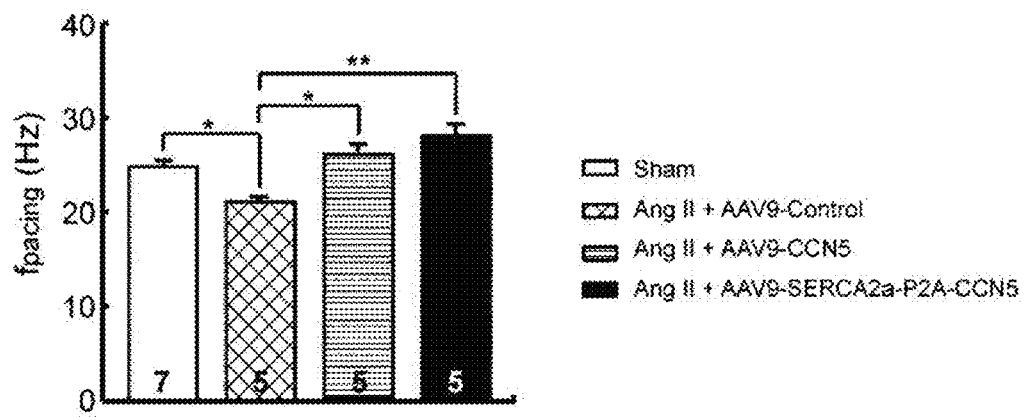
[Fig. 12c]
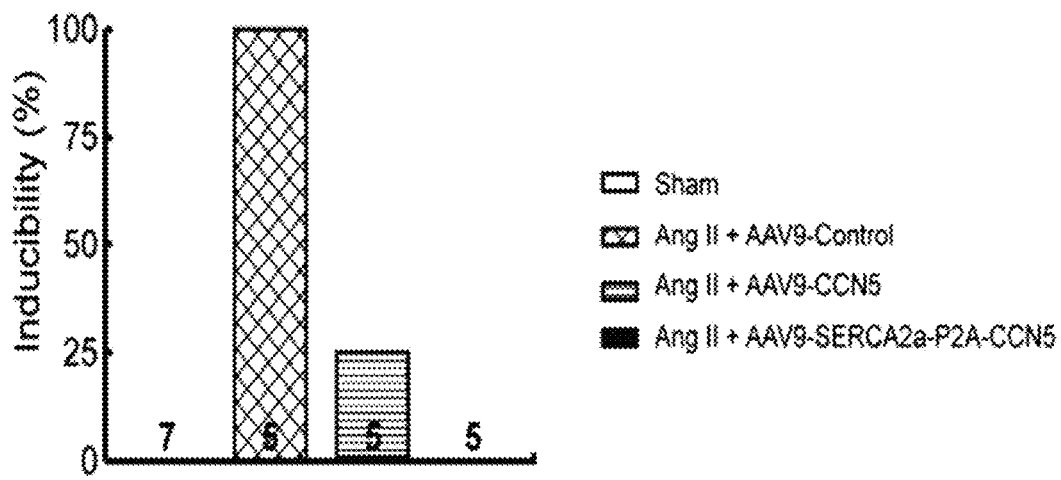
[Fig. 13a]
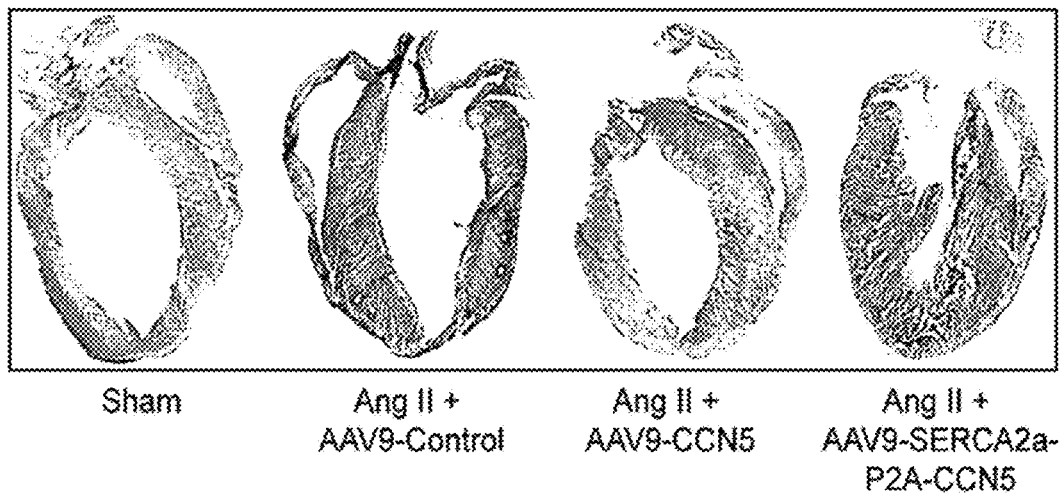

[Fig. 13b]
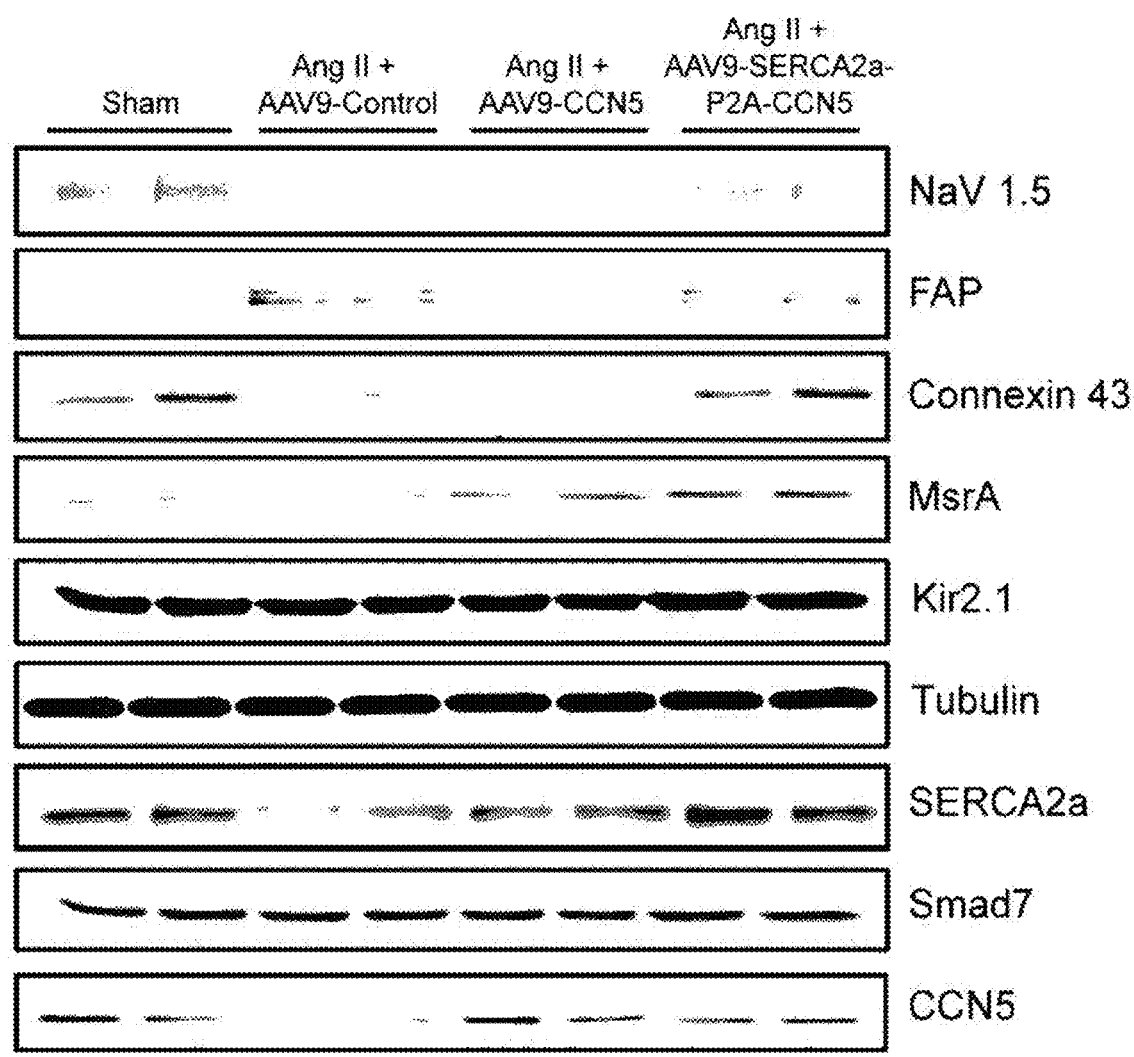

PHARMACEUTICAL COMPOSITION FOR PREVENTING OR TREATING CARDIAC ARRHYTHMIA

CROSS REFERENCE TO RELATED APPLICATIONS

This application is a National Stage of International Application No. PCT/KR2018/011529 filed Sep. 28, 2018, claiming priority based on Korean Patent Application No. 10-2017-0127550 filed Sep. 29, 2017.

TECHNICAL FIELD

The present invention relates to a pharmaceutical composition for preventing or treating cardiac arrhythmia. Specifically, the present invention relates to a pharmaceutical composition comprising, as an active ingredient, CCN5 protein or a nucleotide sequence encoding the same.

BACKGROUND ART

Cardiac arrhythmia is a heart disease caused by abnormalities in regular heart rhythms and effective heart contractions which occur due to problems with electrical signals in the heart. By definition, cardiac arrhythmia is classified into atrial arrhythmia and ventricular arrhythmia depending on its onset location. Specifically, atrial arrhythmia is classified into atrial fibrillation, atrial tachycardia, and sinus node dysfunction; and ventricular arrhythmia is classified into ventricular tachycardia and ventricular fibrillation (Swarminathan P D, et al. Circ Res 2012; 110:1661-1677).

Cardiac arrhythmia causes considerable morbidity and mortality, especially in developed countries, and cardiac arrest is one of the leading causes of death in developed countries (Mozaffarian D, et al. Circulation 2015; 131: e29-e322). In particular, ventricular arrhythmia is the leading cause of sudden cardiac death, and other risk factors for heart disease accelerate and amplify ventricular arrhythmia (Roberts-Thomson K C, et al. Nat Rev Cardiol 2011; 8: 311-321). In addition, among cardiac arrhythmia, atrial fibrillation is the most common arrhythmia, with increasing incidence, and greatly increases incidence of diseases such as cardiac arrhythmia and stroke (Andrada D, et al. Circ Res 2014; 114; 1453-1458).

Therapies for treatment of cardiac arrhythmia include antiarrhythmics, catheter ablation, implantable cardioverter defibrillator for treating ventricular arrhythmia. However, these therapies exhibit limited therapeutic effects. Ion channel blockade, which is the main mechanism of antiarrhythmic treatments, presents limitations in chronic treatment and prevention of arrhythmia. In clinical trials related to cardiac arrhythmia inhibition, during treatment of premature ventricular contractions, antiarrhythmics have been shown to increase cardiovascular mortality in patients with myocardial infarction. A common side effect of currently used antiarrhythmics involves a risk of causing promotion of arrhythmia (Camm J, Int Cardiol 2012; 155: 363-371).

Meanwhile, studies have reported that CaMKII ($Ca^{2+}$/calmodulin-dependent protein kinase II) plays a central role in electrical aspects of cardiac arrhythmia. Increased CaMKII activity leads to hyperactivation of ion channels, defects in intracellular $Ca^{2+}$ homeostasis, and tissue damage, thereby promoting arrhythmia. Thus, inhibition of CaMKII activity may be used as an effective way of treating arrhythmia.

For development of an effective treatment for cardiac arrhythmia, it is necessary to develop such a treatment through understanding of its pathological mechanism and discovery of its new upstream therapeutic targets.

Accordingly, the present invention intends to provide a solution for development of a treatment that simultaneously addresses CaMKII, which is a key target of electrical dysfunction, and fibrosis, which is a major cause of structural dysfunction, as a treatment for onset and maintenance of arrhythmia and for continuous deterioration of symptoms of arrhythmia.

DISCLOSURE OF INVENTION

Technical Problem

Regarding this, the present inventors have studied to develop an effective treatment for cardiac arrhythmia, and as a result, have identified that a pharmaceutical composition, which comprises a gene encoding CCN5 protein or a fragment thereof, inhibits pathological activity of CaMKII and inhibits activity of myofibroblasts, thereby completing the present invention. In addition, the present inventors have identified that a pharmaceutical composition, which comprises a gene encoding CCN5 protein and SERCA2a protein, exhibits a synergistic therapeutic effect on electrical dysfunction in experiments using an animal model of cardiac arrhythmia, thereby completing the present invention.

Solution to Problem

In an aspect of the present invention, there is provided a pharmaceutical composition for preventing or treating cardiac arrhythmia, comprising, as an active ingredient, a gene construct that contains a nucleotide sequence encoding CCN5 protein or a fragment thereof.

In another aspect of the present invention, there is provided a pharmaceutical composition for preventing or treating cardiac arrhythmia, comprising, as an active ingredient, an expression vector loaded with a nucleotide sequence encoding CCN5 protein or a fragment thereof.

In yet another aspect of the present invention, there is provided a pharmaceutical composition for preventing or treating cardiac arrhythmia, comprising, as an active ingredient, a recombinant virus that contains a nucleotide sequence encoding CCN5 protein or a fragment thereof.

In still yet another aspect of the present invention, there is provided a method for preventing or treating cardiac arrhythmia, comprising a step of administering, to a subject, a pharmaceutical composition of the present invention.

In still yet another aspect of the present invention, there is provided a pharmaceutical composition for preventing or treating cardiac arrhythmia, comprising CCN5 protein as an active ingredient.

In still yet another aspect of the present invention, there is provided a method for preventing or treating cardiac arrhythmia, comprising a step of administering CCN5 protein to a subject.

In still yet another aspect of the present invention, there is provided a method for preventing or treating cardiac arrhythmia, comprising a step of administering, to a subject, a gene construct that contains a nucleotide sequence encoding CCN5 protein.

In still yet another aspect of the present invention, there is provided a method for preventing or treating cardiac arrhythmia, comprising a step of administering, to a subject, an expression vector loaded with a nucleotide sequence encoding CCN5 protein.

In still yet another aspect of the present invention, there is provided a method for preventing or treating cardiac arrhythmia, comprising a step of administering, to a subject, a recombinant virus that contains a nucleotide sequence encoding CCN5 protein.

Advantageous Effects of Invention

The pharmaceutical composition for preventing or treating cardiac arrhythmia, of the present invention, inhibits pathological activity of CaMKII which induces cardiac electrical dysfunction, the main cause of atrial arrhythmia and ventricular arrhythmia, so that cardiac electrical functions are restored, and inhibits activity of myofibroblasts which causes structural dysfunction. Therefore, the pharmaceutical composition of the present invention can be effectively used in prevention or treatment of cardiac arrhythmia.

BRIEF DESCRIPTION OF DRAWINGS

FIG. 1 illustrates a schematic diagram for the structure of pTR-CMV-CCN5 vector.

FIG. 2 illustrates a schematic diagram for the structure of pTR-CMV-SERCA2a-P2A-CCN5 vector.

FIG. 3a illustrates a conceptual diagram of animal experiments using wild-type mice and CCN5 TG mice to identify a cardiac fibrosis inhibitory effect of CCN5 protein.

FIG. 3b illustrates photographs obtained by administering angiotensin II to wild-type mice or CCN5 TG mice for 14 days, extracting atrial tissues therefrom, and staining the atrial tissues with Masson's Trichrome staining.

FIG. 3c illustrates results obtained by administering angiotensin II to wild-type mice or CCN5 TG mice for 14 days, extracting atrial tissues therefrom, staining the atrial tissues with Masson's Trichrome staining, and quantifying degree of fibrosis of the stained atrial tissues (*: $p<0.05$; **: $p<0.01$).

FIG. 3d illustrates results obtained by administering angiotensin II to wild-type mice or CCN5 TG mice for 14 days, extracting atrial tissues therefrom, and measuring, through qRT-PCR, mRNA expression level of α-SMA in the atrial tissues (**: $p<0.01$).

FIG. 3e illustrates results obtained by administering angiotensin II to wild-type mice or CCN5 TG mice for 14 days, extracting atrial tissues therefrom, and measuring, through qRT-PCR, mRNA expression level of Collagen I in the atrial tissues (*: $p<0.05$; **: $p<0.01$).

FIG. 3f illustrates results obtained by administering angiotensin II to wild-type mice or CCN5 TG mice for 14 days, extracting atrial tissues therefrom, and measuring, through qRT-PCR, mRNA expression level of TGF-β1 in the atrial tissues (*: $p<0.05$; **: $p<0.01$).

FIG. 3g illustrates results obtained by administering angiotensin II to wild-type mice or CCN5 TG mice for 14 days, extracting atrial tissues therefrom, and measuring, through qRT-PCR, mRNA expression level of IL-1β in the atrial tissues (*: $p<0.05$).

FIG. 3h illustrates results obtained by administering angiotensin II to wild-type mice or CCN5 TG mice for 14 days, extracting atrial tissues therefrom, and measuring, through qRT-PCR, mRNA expression level of RANTES in the atrial tissues (*: $p<0.05$; **: $p<0.01$).

FIG. 3i illustrates results obtained by administering angiotensin II to wild-type mice or CCN5 TG mice for 14 days, extracting atrial tissues therefrom, and measuring, through qRT-PCR, mRNA expression level of F4/80 in the atrial tissues (**: $p<0.01$).

FIG. 3j illustrates results obtained by administering angiotensin II to wild-type mice or CCN5 TG mice for 14 days, extracting atrial tissues therefrom, and measuring, through qRT-PCR, mRNA expression level of MCP-1 in the atrial tissues (**: $p<0.01$).

FIG. 4a illustrates a conceptual diagram of animal experiments using wild-type mice and CCN5 TG mice to identify an inhibitory effect of CCN5 protein on atrial fibrillation.

FIG. 4b illustrates results obtained by administering angiotensin II to wild-type mice or CCN5 TG mice for 14 days, extracting hearts therefrom, applying an electrical stimulus thereto to induce atrial fibrillation, and measuring electrocardiogram.

FIG. 4c illustrates results obtained by administering angiotensin II to wild-type mice or CCN5 TG mice for 14 days, extracting hearts therefrom, and measuring frequency of atrial fibrillation induced when an electrical stimulus is applied to the hearts to induce atrial fibrillation.

FIG. 5a illustrates a conceptual diagram of experiments using HL-1 cells to identify an inhibitory effect of CCN5 protein on atrial fibrillation.

FIG. 5b illustrates results obtained by subjecting HL-1 cells to treatment with angiotensin II and simultaneously with CM-Con or CM-CCN5, performing culture for 48 hours, and then identifying, through western blotting, expression of the proteins, p-CaMKII (Thr286), CaMKII, pRyR2 (Ser2808), pRyR2 (Ser2814), RyR2, calsequestrin2, $Na^+/Ca^+$ exchanger 2 (NCX2), and GAPDH, in HL-1 cells.

FIG. 5c illustrates results obtained by subjecting HL-1 cells to treatment with angiotensin II and simultaneously with CM-Con or CM-CCN5, performing culture for 48 hours, and then calculating p-CaMKII (Thr286)/CaMKII values in HL-1 cells (**: $p<0.01$).

FIG. 5d illustrates results obtained by subjecting HL-1 cells to treatment with angiotensin II and simultaneously with CM-Con or CM-CCN5, performing culture for 48 hours, and then calculating pRyR2 (Ser2808)/RyR2 values in HL-1 cells (**: $p<0.01$).

FIG. 5e illustrates results obtained by subjecting HL-1 cells to treatment with angiotensin II and simultaneously with CM-Con or CM-CCN5, performing culture for 48 hours, and then calculating pRyR2 (Ser2814)/RyR2 values in HL-1 cells (*: $p<0.05$; **: $p<0.01$).

FIG. 5f illustrates results obtained by subjecting HL-1 cells to treatment with angiotensin II and simultaneously with CM-Con or CM-CCN5, performing culture for 48 hours, and then calculating calsequestrin2/GAPDH values in HL-1 cells (*: $p<0.05$; **: $p<0.01$).

FIG. 5g illustrates results obtained by subjecting HL-1 cells to treatment with angiotensin II and simultaneously with CM-Con or CM-CCN5, performing culture for 48 hours, and then calculating NCX2/GAPDH values in HL-1 cells (**: $p<0.01$).

FIG. 6a illustrates a conceptual diagram of experiments using rat atrial fibroblasts to identify an inhibitory effect of CCN5 protein on atrial fibrillation.

FIG. 6b illustrates photographs obtained by subjecting rat atrial fibroblasts to treatment with angiotensin II and simultaneously with CM-Con or CM-CCN5, performing culture for 48 hours, and then staining the cultured rat atrial fibroblasts with fluorescence immunochemistry.

FIG. 6c illustrates results obtained by subjecting rat atrial fibroblasts to treatment with angiotensin II and simultaneously with CM-Con or CM-CCN5, performing culture for 48 hours, and then identifying, through western blotting, expression of the proteins, α-SMA, Collagen I, TGF-β1, and α-tubulin, in the atrial fibroblasts.

FIG. 6d illustrates results obtained by subjecting rat atrial fibroblasts to treatment with angiotensin II and simultaneously with CM-Con or CM-CCN5, performing culture for 48 hours, and then calculating α-SMA/α-tubulin values in the atrial fibroblasts (*: $p<0.05$; **: $p<0.01$).

FIG. 6e illustrates results obtained by subjecting rat atrial fibroblasts to treatment with angiotensin II and simultaneously with CM-Con or CM-CCN5, performing culture for 48 hours, and then calculating Collagen I/α-tubulin values in the atrial fibroblasts (*: $p<0.05$; **: $p<0.01$).

FIG. 6f illustrates results obtained by subjecting rat atrial fibroblasts to treatment with angiotensin II and simultaneously with CM-Con or CM-CCN5, performing culture for 48 hours, and then calculating TGF-β$^1$/α-tubulin values in the atrial fibroblasts (*: $p<0.05$; **: $p<0.01$).

FIG. 6g illustrates results obtained by subjecting rat atrial fibroblasts to treatment with angiotensin II and simultaneously with CM-Con or CM-CCN5, performing culture for 48 hours, and then measuring, through qRT-PCR, mRNA expression level of α-SMA in atrial tissues (*: $p<0.05$).

FIG. 6h illustrates results obtained by subjecting rat atrial fibroblasts to treatment with angiotensin II and simultaneously with CM-Con or CM-CCN5, performing culture for 48 hours, and then measuring, through qRT-PCR, mRNA expression level of Collagen I in atrial tissues (**: $p<0.01$).

FIG. 6i illustrates results obtained by subjecting rat atrial fibroblasts to treatment with angiotensin II and simultaneously with CM-Con or CM-CCN5, performing culture for 48 hours, and then measuring, through qRT-PCR, mRNA expression level of TGF-β1 in atrial tissues (*: $p<0.05$; **: $p<0.01$).

FIG. 7a illustrates a conceptual diagram of animal experiments using atrial fibrosis-induced mice to identify a therapeutic effect of AAV-CCN5 protein on atrial fibrosis.

FIG. 7b illustrates results obtained by administering angiotensin II to wild-type mice for 14 days, injecting AAV-Control or AAV-CCN5 thereinto, extracting atrial tissues therefrom 4 weeks after the injection, and identifying protein expression of CCN5 through western blotting.

FIG. 7c illustrates results obtained by administering angiotensin II to wild-type mice for 14 days, injecting AAV-Control or AAV-CCN5 thereinto, extracting atrial tissues therefrom 4 weeks after the injection, and identifying protein and mRNA expression levels of CCN5.

FIG. 7d illustrates photographs obtained by administering angiotensin II to wild-type mice for 14 days, injecting AAV-Control or AAV-CCN5 thereinto, extracting atrial tissues therefrom 4 weeks after the injection, and staining the atrial tissues with Masson's Trichrome staining.

FIG. 7e illustrates results obtained by administering angiotensin II to wild-type mice for 14 days, injecting AAV-Control or AAV-CCN5 thereinto, extracting atrial tissues therefrom 4 weeks after the injection, staining the atrial tissues with Masson's Trichrome staining, and quantifying degree of fibrosis in the stained atrial tissues (*: $p<0.05$).

FIG. 7f illustrates results obtained by administering angiotensin II to wild-type mice for 14 days, injecting AAV-Control or AAV-CCN5 thereinto, extracting atrial tissues therefrom 4 weeks after the injection, and calculating, through qRT-PCR, α-SMA/18s rRNA values in the atrial tissues (*: $p<0.05$).

FIG. 7g illustrates results obtained by administering angiotensin II to wild-type mice for 14 days, injecting AAV-Control or AAV-CCN5 thereinto, extracting atrial tissues therefrom 4 weeks after the injection, and calculating, through qRT-PCR, Collagen I/18s rRNA values in the atrial tissues (*: $p<0.05$; **: $p<0.01$).

FIG. 7h illustrates results obtained by administering angiotensin II to wild-type mice for 14 days, injecting AAV-Control or AAV-CCN5 thereinto, extracting atrial tissues therefrom 4 weeks after the injection, and calculating, through qRT-PCR, TGF-β1/18s rRNA values in the atrial tissues (**: $p<0.01$).

FIG. 7i illustrates results obtained by administering angiotensin II to wild-type mice for 14 days, injecting AAV-Control or AAV-CCN5 thereinto, extracting atrial tissues therefrom 4 weeks after the injection, and calculating, through qRT-PCR, IL-113/18s rRNA values in the atrial tissues (*: $p<0.05$).

FIG. 7j illustrates results obtained by administering angiotensin II to wild-type mice for 14 days, injecting AAV-Control or AAV-CCN5 thereinto, extracting atrial tissues therefrom 4 weeks after the injection, and calculating, through qRT-PCR, RANTES/18s rRNA values in the atrial tissues (**: $p<0.01$).

FIG. 7k illustrates results obtained by administering angiotensin II to wild-type mice for 14 days, injecting AAV-Control or AAV-CCN5 thereinto, extracting atrial tissues therefrom 4 weeks after the injection, and calculating, through qRT-PCR, F4/80/18s rRNA values in the atrial tissues (*: $p<0.05$; **: $p<0.01$).

FIG. 7l illustrates results obtained by administering angiotensin II to wild-type mice for 14 days, injecting AAV-Control or AAV-CCN5 thereinto, extracting atrial tissues therefrom 4 weeks after the injection, and calculating, through qRT-PCR, MCP-1/18s rRNA values in the atrial tissues (**: $p<0.01$).

FIG. 8a illustrates a conceptual diagram of animal experiments using atrial fibrillation-induced mice to identify an atrial fibrillation inhibitory effect of AAV-CCN5 protein.

FIG. 8b illustrates electrocardiogram results obtained by administering angiotensin II to wild-type mice for 14 days, injecting AAV-Control or AAV-CCN5 thereinto, and measuring electrocardiogram 4 weeks after the injection.

FIG. 8c illustrates results obtained by administering angiotensin II to wild-type mice for 14 days, injecting AAV-Control or AAV-CCN5 thereinto, and observing incidence of arrhythmia with an electrical stimulus 4 weeks after the injection.

FIG. 8d illustrates results obtained by administering angiotensin II to wild-type mice for 14 days, injecting AAV-Control or AAV-CCN5 thereinto, and observing intensity of an electrical stimulus required for inducing arrhythmia 4 weeks after the injection.

FIG. 8e illustrates results obtained by administering angiotensin II to wild-type mice for 14 days, injecting AAV-Control or AAV-CCN5 thereinto, and measuring action potential of $Ca^{2+}$ 4 weeks after the injection.

FIG. 8f illustrates results obtained by administering angiotensin II to wild-type mice for 14 days, injecting AAV-Control or AAV-CCN5 thereinto, and measuring action potential duration 50 ($APD_{50}$) and action potential duration 75 ($APD_{75}$) 4 weeks after the injection.

FIG. 8g illustrates results obtained by administering angiotensin II to wild-type mice for 14 days, injecting AAV-Control or AAV-CCN5 thereinto, and measuring depolarization velocity 4 weeks after the injection (*: $p<0.05$).

FIG. 9a illustrates fractional shortening and changes in body weight over 6 weeks in wild-type mice and ventricular arrhythmia-induced mice.

FIG. 9b illustrates optical maps obtained by applying an electrical stimulus of 10 Hz to the right ventricle (RV) of wild-type mice and ventricular arrhythmia-induced mice and taking a photograph.

FIG. 9c illustrates optical maps obtained by applying an electrical stimulus of 20 Hz to the right ventricle (RV) of wild-type mice and ventricular arrhythmia-induced mice and taking a photograph.

FIG. 9d illustrates results obtained by measuring action potential of $Ca^{2+}$ in wild-type mice and ventricular arrhythmia-induced mice.

FIG. 9e illustrates results obtained by measuring action potential duration 50 ($APD_{50}$) and action potential duration 75 ($APD_{75}$) in wild-type mice and ventricular arrhythmia-induced mice (*: $p<0.05$).

FIG. 9f illustrates results obtained by measuring dispersion of action potential duration in wild-type mice and ventricular arrhythmia-induced mice (*: $p<0.05$).

FIG. 9g illustrates conduction velocity and depolarization velocity in wild-type mice and ventricular arrhythmia-induced mice (***  $p<0.001$).

FIG. 10a illustrates changes in action potential of $Ca^{2+}$, depending on ISO treatment, in wild-type mice and ventricular arrhythmia-induced mice.

FIG. 10b illustrates changes in $Ca^{2+}$ repolarization pattern, depending on ISO treatment, in the right ventricle of the wild-type mice and ventricular arrhythmia-induced mice.

FIG. 10c illustrates changes in action potential duration 75 ($APD_{75}$), depending on ISO treatment, in wild-type mice and ventricular arrhythmia-induced mice.

FIG. 10d illustrates $Ca^{2+}$ optical maps obtained after subjecting the wild type mice and ventricular arrhythmia-induced mice to treatment with ISO.

FIG. 10e illustrates results obtained after subjecting wild type mice and ventricular arrhythmia-induced mice to treatment with ISO and then measuring action potential duration 75 ($APD_{75}$) (*: $p<0.05$).

FIG. 10f illustrates changes in depolarization velocity, depending on ISO treatment, in wild-type mice and ventricular arrhythmia-induced mice (***: $p<0.001$).

FIG. 11a illustrates fractional shortening over 6 weeks in wild-type mice, ventricular arrhythmia-induced mice injected with AAV9-Control, ventricular arrhythmia-induced mice injected with AAV9-CCN5, and ventricular arrhythmia-induced mice injected with AAV9-SERCA2a-P2A-CCN5.

FIG. 11b illustrates changes in left ventricular wall thickness over 6 weeks in wild-type mice, ventricular arrhythmia-induced mice injected with AAV9-Control, ventricular arrhythmia-induced mice injected with AAV9-CCN5, and ventricular arrhythmia-induced mice injected with AAV9-SERCA2a-P2A-CCN5.

FIG. 11c illustrates $Ca^{2+}$ optical maps for ventricular arrhythmia-induced mice injected with AAV9-CCN5 and ventricular arrhythmia-induced mice injected with ISO and AAV9-CCN5.

FIG. 11d illustrates $Ca^{2+}$ optical maps for ventricular arrhythmia-induced mice injected with AAV9-SERCA2a-P2A-CCN5 and ventricular arrhythmia-induced mice injected with ISO and AAV9-SERCA2a-P2A-CCN5.

FIG. 11e illustrates changes in action potential of $Ca^{2+}$, depending on ISO treatment, in ventricular arrhythmia-induced mice injected with AAV9-CCN5 and ventricular arrhythmia-induced mice injected with AAV9-SERCA2a-P2A-CCN5.

FIG. 11f illustrates $Ca^{2+}$ repolarization pattern in the left ventricle of wild-type mice, ventricular arrhythmia-induced mice injected with AAV9-Control, ventricular arrhythmia-induced mice injected with AAV9-CCN5, and ventricular arrhythmia-induced mice injected with AAV9-SERCA2a-P2A-CCN5.

FIG. 11g illustrates changes in action potential duration 75 ($APD_{75}$), depending on ISO treatment, in wild-type mice, ventricular arrhythmia-induced mice injected with AAV9-Control, ventricular arrhythmia-induced mice injected with AAV9-CCN5, and ventricular arrhythmia-induced mice injected with AAV9-SERCA2a-P2A-CCN5 (*: $p<0.05$; : $p<0.01$; *: $p<0.001$).

FIG. 11h illustrates conduction velocity, depending on ISO treatment, in wild-type mice, ventricular arrhythmia-induced mice injected with AAV9-Control, ventricular arrhythmia-induced mice injected with AAV9-CCN5, and ventricular arrhythmia-induced mice injected with AAV9-SERCA2a-P2A-CCN5 (*: $p<0.05$; ***: $p<0.001$).

FIG. 11i illustrates depolarization velocity, depending on ISO treatment, in wild-type mice, ventricular arrhythmia-induced mice injected with AAV9-Control, ventricular arrhythmia-induced mice injected with AAV9-CCN5, and ventricular arrhythmia-induced mice injected with AAV9-SERCA2a-P2A-CCN5 (: $p<0.01$; *: $p<0.001$).

FIG. 12a illustrates changes in electrocardiogram observed in a case where an electrical stimulus is applied to wild-type mice, ventricular arrhythmia-induced mice injected with AAV9-Control, ventricular arrhythmia-induced mice injected with AAV9-CCN5, and ventricular arrhythmia-induced mice injected with AAV9-SERCA2a-P2A-CCN5.

FIG. 12b illustrates intensity of an electrical stimulus required for inducing arrhythmia in wild-type mice, ventricular arrhythmia-induced mice injected with AAV9-Control, ventricular arrhythmia-induced mice injected with AAV9-CCN5, and ventricular arrhythmia-induced mice injected with AAV9-SERCA2a-P2A-CCN5.

FIG. 12c illustrates incidence of arrhythmia with an electrical stimulus in wild-type mice, ventricular arrhythmia-induced mice injected with AAV9-Control, ventricular arrhythmia-induced mice injected with AAV9-CCN5, and ventricular arrhythmia-induced mice injected with AAV9-SERCA2a-P2A-CCN5.

FIG. 13a illustrates photographs obtained by extracting hearts from wild-type mice, ventricular arrhythmia-induced mice injected with AAV9-Control, ventricular arrhythmia-induced mice injected with AAV9-CCN5, and ventricular arrhythmia-induced mice injected with AAV9-SERCA2a-P2A-CCN5, and staining the hearts with Masson's Trichrome staining.

FIG. 13b illustrates results obtained by identifying, through Western blotting, expression of the proteins, Nav 1.5, FAP, connexin 43, MsrA, Kir2.1, Tubulin, SERCA2a, Smad7, and CCN5, in cardiac tissues of wild-type mice, ventricular arrhythmia-induced mice injected with AAV9-Control, ventricular arrhythmia-induced mice injected with AAV9-CCN5, and ventricular arrhythmia-induced mice injected with AAV9-SERCA2a-P2A-CCN5.

BEST MODE FOR CARRYING OUT THE INVENTION

Hereinafter, the present invention will be described in detail.

In an aspect of the present invention, there is provided a pharmaceutical composition for preventing or treating cardiac arrhythmia, comprising, as an active ingredient, a gene construct that contains a nucleotide sequence encoding a CCN5 protein or a fragment thereof.

As used herein, the term "CCN5 protein" refers to a matricellular protein belonging to the CCN family that plays various roles in regulation of cellular functions such as vascular disease induction, angiogenesis, tumorigenesis, fibrosis disease induction, cell differentiation, and survival. The CCN5 protein, unlike other CCN family proteins, has no C-terminal domain and is also called WISP-2, HICP, Cop1, CTGF-L, or the like. In addition, the CCN5 protein consists of a single polypeptide chain of 250-amino acid sequence. Due to a 22-amino acid secretory leader sequence at the N-terminus, the CCN5 protein is secreted out of a cell and functions as a signaling protein. Thus, when the nucleotide sequence is expressed in a cell, the CCN5 protein can be secreted out of the cell. Here, the nucleotide sequence may be in the form of mRNA.

Specifically, the CCN5 protein may have the amino acid sequence represented by SEQ ID NO: 1. In addition, the nucleotide sequence encoding the CCN5 protein may be the sequence represented by SEQ ID NO: 2 or SEQ ID NO: 41.

In addition, the fragment of the CCN5 protein may be one obtained by truncation of a portion of the N-terminus and/or C-terminus of the wild-type CCN5 as long as the fragment maintains activity of the CCN5 protein. Specifically, the fragment of the CCN5 protein may be one obtained by truncation of 1 to 30, 1 to 20, 1 to 10, or 1 to 5 amino acids from the N-terminus or C-terminus.

In addition, the gene construct may contain a promoter sequence operatively linked thereto.

As used herein, the term "operatively linked" refers to functional linkage between a nucleotide expression regulatory sequence (such as promoter, signal sequence, or array of transcription factor binding sites) and other nucleotide sequences. The regulatory sequence regulates transcription and/or translation of the other nucleotide sequences.

Specifically, a promoter linked to a nucleotide sequence encoding a CCN5 protein or a fragment thereof may operate, preferably in animal cells, and more preferably in mammalian cells, to regulate transcription of the CCN5 gene. The promoter includes promoters derived from the mammalian viruses and promoters derived from mammalian cell genomes. The promoter may operate specifically in cardiac cells.

The promoter may be any one selected from the group consisting of cytomegalovirus (CMV) promoter, adenovirus late promoter, vaccinia virus 7.5K promoter, SV40 promoter, HSV tk promoter, RSV promoter, EF1 alpha promoter, metallothionein promoter, β-actin promoter, human IL-2 gene promoter, human IFN gene promoter, human IL-4 gene promoter, human lymphotoxin gene promoter, and human GM-CSF gene promoter. However, the promoter is not limited thereto. Specifically, the promoter may be CMV promoter.

The gene construct may further contain a nucleotide sequence encoding a SERCA2a protein or a fragment thereof. Here, the nucleotide sequence may be in the form of mRNA.

Here, in the gene construct, the nucleotide sequence encoding the SERCA2a protein or a fragment thereof may be contained, in 5' to 3' direction, in the order of the nucleotide sequence encoding the SERCA2a protein or fragment thereof—the nucleotide sequence encoding the CCN5 protein or fragment thereof. Here, the nucleotide sequence encoding the CCN5 protein or a fragment thereof may contain a stop codon.

In addition, in the gene construct, the nucleotide sequence encoding the SERCA2a protein or a fragment thereof may be contained, in 5' to 3' direction, in the order of the nucleotide sequence encoding the CCN5 protein or fragment thereof—the nucleotide sequence encoding the SERCA2a protein or fragment thereof. Here, the nucleotide sequence encoding the SERCA2a protein or a fragment thereof may contain a stop codon.

In addition, the gene construct may further contain a self-cleavage sequence between the nucleotide sequence encoding the SERCA2a protein or a fragment thereof and the nucleotide sequence encoding the CCN5 protein or a fragment thereof.

As used herein, the term "SERCA2a protein" refers to a protein that functions to cause reuptake of calcium into the sarcoplasmic reticulum using ATP energy. It has been reported that a remarkably decreased expression level of the SERCA2a protein is observed in patients with heart failure with reduced ejection fraction (HFrEF). Reduced calcium reuptake into the sarcoplasmic reticulum, which results from decreased expression of the SERCA2a protein, abnormally increases the calcium concentration in the cytoplasm, weakens the contraction-relaxation function of cardiomyocytes, and acts as a direct cause of cardiomyocyte death by causing generation of harmful oxygen, destruction of energy metabolism function, and the like due to influx of calcium into the mitochondria.

Specifically, the SERCA2a protein may have the amino acid sequence represented by SEQ ID NO: 3. In addition, the nucleotide sequence encoding the SERCA2a protein may be the sequence represented by SEQ ID NO: 4 or SEQ ID NO: 42.

In addition, the fragment of the SERCA2a protein may be one obtained by truncation of a portion of the N-terminus and/or C-terminus of the wild-type SERCA2a as long as the fragment maintains activity of the SERCA2a protein. Specifically, the fragment of the SERCA2a protein may be one obtained by truncation of 1 to 100, 1 to 50, 1 to 20, or 1 to 10 amino acids from the N-terminus or C-terminus.

The self-cleavage sequence may be a nucleotide sequence encoding 2A peptide derived from porcine teschovirus-1, *Thosea asigna* virus, equine rhinitis A virus, or foot-and-mouth disease virus. Specifically, the self-cleavage sequence may be a nucleotide sequence encoding 2A peptide derived from porcine teschovirus-1. In addition, the self-cleavage sequence may be the nucleotide sequence represented by SEQ ID NO: 6.

The nucleotide sequence encoding the 2A peptide derived from porcine teschovirus-1 may be a nucleotide sequence encoding the amino acid sequence represented by SEQ ID NO: 5. In addition, the nucleotide sequence encoding the amino acid sequence represented by SEQ ID NO: 5 may be the nucleotide sequence represented by SEQ ID NO: 6.

The nucleotide sequence encoding the 2A peptide derived from *Thosea asigna* virus may be a nucleotide sequence encoding the amino acid sequence represented by SEQ ID NO: 7. In addition, the nucleotide sequence encoding the amino acid sequence represented by SEQ ID NO: 7 may be the nucleotide sequence represented by SEQ ID NO: 8.

The nucleotide sequence encoding the 2A peptide derived from equine rhinitis A virus may be a nucleotide sequence encoding the amino acid sequence represented by SEQ ID NO: 9. In addition, the nucleotide sequence encoding the amino acid sequence represented by SEQ ID NO: 9 may be the nucleotide sequence represented by SEQ ID NO: 10.

The nucleotide sequence encoding the 2A peptide derived from foot-and-mouth disease virus may be a nucleotide sequence encoding the amino acid sequence represented by SEQ ID NO: 11. In addition, the nucleotide sequence encoding the amino acid sequence represented by SEQ ID NO: 11 may be the nucleotide sequence represented by SEQ ID NO: 12.

When SERCA2a-P2A-CCN5, an embodiment of the gene construct, is expressed in a cell, the SERCA2a protein may be inserted into the sarcoplasmic reticulum membrane, and the CCN5 protein may be secreted out of the cell. In addition, when CCN5-P2a-SERCA2a, an embodiment of the gene construct of the present invention, is expressed in a cell, the SERCA2a protein may be inserted into the sarcoplasmic reticulum membrane, and the CCN5 protein may be secreted out of the cell.

As used herein, the term "cardiac arrhythmia" refers to a disease in which the heart does not continue regular contraction due to poor generation of an electrical stimulus in the heart or poor transmission of the stimulus, and the heartbeat becomes abnormally fast, slow, or irregular.

The cardiac arrhythmia is classified into atrial arrhythmia and ventricular arrhythmia depending on its onset location. The atrial arrhythmia may include atrial fibrillation, atrial tachycardia, or sinus node dysfunction. The ventricular arrhythmia may include ventricular tachycardia or ventricular fibrillation.

In addition, the gene construct of the present invention may be delivered into a cell using liposomes. Liposomes are formed automatically by phospholipids dispersed in the aqueous phase, and liposomes containing a nucleotide sequence encoding a CCN5 protein and/or a nucleotide sequence encoding a SERCA2a protein allows the nucleotide sequence encoding the CCN5 protein and/or the nucleotide sequence encoding the SERCA2a protein to be delivered into a cell through a mechanism such as endocytosis, adsorption to cell surface, or fusion with plasma cell membrane.

In another aspect of the present invention, there is provided a pharmaceutical composition for preventing or treating cardiac arrhythmia, comprising, as an active ingredient, an expression vector loaded with a nucleotide sequence encoding a CCN5 protein or a fragment thereof.

The CCN5 protein is as described above for the pharmaceutical composition for preventing or treating cardiac arrhythmia which comprises the gene construct as an active ingredient.

As used herein, the term "expression vector" refers to a recombinant vector capable of expressing a target protein in a target host cell, the recombinant vector being a gene construct that contains essential regulatory elements operatively linked to a gene insert so that the gene insert is expressed.

In addition, the expression vector may contain a signal sequence for secretion of a fusion polypeptide so that protein isolation from a cell culture is facilitated. Specific initiation signals may also be required for efficient translation of an inserted nucleic acid sequence. These signals contain the ATG start codon and contiguous sequences. In some cases, exogenous translational regulatory signals must be provided which may contain the ATG start codon. These exogenous translational regulatory signals and start codons may be of various natural and synthetic sources. Expression efficiency may be increased by introduction of an appropriate transcription- or translation-enhancing element.

In addition, the expression vector may be further loaded with a nucleotide sequence encoding a SERCA2a protein or a fragment thereof. Here, in the expression vector, the nucleotide sequence encoding the SERCA2a protein or a fragment thereof may be contained, in 5' to 3' direction, in the order of the nucleotide sequence encoding the SERCA2a protein or fragment thereof—the nucleotide sequence encoding the CCN5 protein or fragment thereof.

The expression vector may further contain a self-cleavage sequence between the nucleotide encoding the SERCA2a protein or a fragment thereof and the nucleotide encoding the CCN5 protein or a fragment thereof. The self-cleavage sequence is as described above for the pharmaceutical composition for preventing or treating cardiac arrhythmia which comprises the gene construct as an active ingredient.

The expression vector may be loaded with the nucleotide sequence encoding the CCN5 protein or a fragment thereof and/or the nucleotide sequence encoding the SERCA2a protein or a fragment thereof, of the present invention. Here, the vector used is not particularly limited as long as it can produce the CCN5 protein and/or the SERCA2a protein of the present invention. The expression vector may be any one selected from the group consisting of plasmid vectors and cosmid vectors.

The plasmid vector may include, but is not limited to, commercially available plasmids such as pUC18, pBAD, and pIDTSAMRT-AMP.

The cardiac arrhythmia is as described above for the pharmaceutical composition for preventing or treating cardiac arrhythmia which comprises the gene construct as an active ingredient.

In yet another aspect of the present invention, there is provided a pharmaceutical composition for preventing or treating cardiac arrhythmia, comprising, as an active ingredient, a recombinant virus that contains a nucleotide sequence encoding a CCN5 protein or a fragment thereof.

The CCN5 protein is as described above for the pharmaceutical composition for preventing or treating cardiac arrhythmia which comprises the gene construct as an active ingredient.

The virus may be any one selected from the group consisting of adenovirus, adeno-associated virus (AAV), retrovirus, lentivirus, herpes simplex virus, vaccinia virus, and the like. Specifically, the virus may be, but is not limited to, adeno-associated virus.

The adenovirus is widely used as a gene transfer vector because of its mid-sized genome, ease of manipulation, high titer, wide target-cell range, and excellent infectivity. Its genome is flanked by 100 to 200 bp of inverted terminal repeat (ITR) which is an essential cis element for DNA replication and packaging. E1 regions (E1A and E1B) of the genome encode proteins that are involved in viral DNA replication.

Among adenovirus vectors, replication-incompetent adenoviruses lacking the E1 regions are widely used. On the other hand, E3 region is deleted from conventional adenovirus vectors to provide a site for insertion of a foreign gene.

Thus, the CCN5 gene of the present invention may be inserted into the deleted E1 regions (E1A region and/or E1B region, preferably E1B region) or E3 region. Specifically, the CCN5 protein gene may be inserted into the E3 region.

Meanwhile, the target nucleotide sequence to be delivered into a cell may be inserted into the deleted E1 regions (E1A region and/or E1B region, preferably E1B region) or E3 region, preferably E3 region. In addition, the target nucleotide sequence may also be expressed by a bicistronic expression system linked by the internal ribosome entry site (IRES) such as promoter-target nucleotide sequence-poly A sequence-IRES-CCN5 protein gene.

In addition, since up to approximately 105% of the wild-type genome can be packaged in adenovirus, about 2 kb may be additionally packaged in adenovirus. Thus, a foreign sequence to be inserted into adenovirus may be additionally linked to the adenoviral genome.

Adenovirus has 42 different serotypes and subgroups A to F. Among these, adenovirus type 5 belonging to subgroup C is suitable for obtaining an adenovirus vector of the present invention. Biochemical and genetic information on adenovirus type 5 is well known.

Foreign genes to be delivered by adenovirus replicate in the same way as episomes, and therefore, have very low genotoxicity to host cells.

The retrovirus is widely used as a gene transfer vector because the retrovirus is capable of inserting its gene into the host genome and delivering a large amount of foreign genetic material, and has a broad spectrum of cells it can infect.

In order to construct a retroviral vector, the CCN5 gene and the target nucleotide sequence to be delivered are inserted into the retroviral genome instead of the retroviral sequence to produce a replication-incompetent virus. In order to produce virions, a packaging cell line, which contains gag, pol, and env genes, and lacks long terminal repeat (LTR) and Ψ sequence, is constructed. When a recombinant plasmid that contains the CCN5 gene, the target nucleotide sequence to be delivered, LTR and Ψ sequence is introduced into the cell line, the Ψ sequence enables production of an RNA transcript of the recombinant plasmid. This transcript is packaged into a virus, and the virus is secreted into the medium. The medium containing the recombinant retroviruses is collected, enriched, and used as a gene delivery system.

The adeno-associated virus (AAV) is suitable as the gene delivery system of the present invention because it is capable of infecting non-dividing cells and has capacity to infect various types of cells. Details of construction and use of AAV vectors are disclosed in U.S. Pat. Nos. 5,139,941 and 4,797,368.

Typically, an AAV virus is produced by co-transformation of a plasmid containing a target gene sequence (CCN5 gene and target nucleotide sequence to be delivered) that is flanked by two AAV terminal repeats and an expression plasmid containing the wild-type AVV coding sequence that lacks the terminal repeats.

Vectors derived from the vaccinia virus, the lentivirus, or the herpes simplex virus may also be used to deliver, into a cell, the CCN5 gene and the target nucleotide sequence to be delivered.

In addition, the virus may further contain a promoter sequence operatively linked to the nucleotide sequence. The operatively linked promoter sequence is as described above for the pharmaceutical composition for preventing or treating cardiac arrhythmia which comprises the gene construct as an active ingredient.

In addition, the recombinant virus may be further loaded with a nucleotide sequence encoding a SERCA2a protein or a fragment thereof. Here, in the recombinant virus, the nucleotide sequence encoding the SERCA2a protein or a fragment thereof may be contained, in 5' to 3' direction, in the order of the nucleotide sequence encoding the SERCA2a protein or fragment thereof—the nucleotide sequence encoding the CCN5 protein or fragment thereof.

In addition, the recombinant virus may contain a self-cleavage sequence between the nucleotide sequence encoding the SERCA2a protein or a fragment thereof and the nucleotide sequence encoding the CCN5 protein or a fragment thereof. The self-cleavage sequence is as described above for the pharmaceutical composition for preventing or treating cardiac arrhythmia which comprises the gene construct as an active ingredient.

The cardiac arrhythmia is as described above.

In the present invention, a method of administering a pharmaceutical composition, which comprises, as an active ingredient, a virus that contains a gene construct, may be performed according to virus infection methods known in the art. In addition, in the present invention, when the gene construct as an active ingredient is contained in a naked recombinant DNA molecule or a plasmid, a microinjection method, a liposome-mediated transfection method, a DEAE-dextran treatment method, and a gene bombardment method may be used to introduce a gene into cells.

A pharmaceutically acceptable carrier to be contained in the pharmaceutical composition of the present invention is one conventionally used for formulation, and examples thereof include, but are not limited to, lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, magnesium stearate, and mineral oil.

The pharmaceutical composition of the present invention may further comprise, in addition to the above ingredients, a lubricant, a wetting agent, a sweetener, a flavoring agent, an emulsifier, a suspending agent, a preservative, and the like. Suitable pharmaceutically acceptable carriers and formulations are described in detail in Remington's Pharmaceutical Sciences (19th ed., 1995).

A dosage form of the pharmaceutical composition may vary depending on method of use, and may be made into injections.

A dose of the pharmaceutical composition of the present invention is desirably determined in consideration of the patient's age, sex, condition, degree of absorption of active ingredients in the body, inactivation rate, and drugs used in combination; and the pharmaceutical composition may be administered in an amount of 0.0001 mg/kg (body weight) to 100 mg/kg (body weight) based on CCN5 protein.

A dose of the pharmaceutical composition of the present invention is desirably determined in consideration of the patient's age, sex, condition, degree of absorption of active ingredients in the body, inactivation rate, and drugs used in combination; and when the pharmaceutical composition is a virus, the pharmaceutical composition may be administered in an amount of $1.0 \times 10^3$ to $1.0 \times 10^{20}$ viral genomes per day on an adult basis. Specifically, the pharmaceutical composition of the present invention may be administered in an amount of $1.0 \times 10^3$ to $1.0 \times 10^{20}$, $1.0 \times 10^8$ to $1.0 \times 10^{16}$, $1.0 \times 10^{12}$ to $1.0 \times 10^{15}$, or $1.0 \times 10^{13}$ to $1.0 \times 10^{14}$ viral genomes per day on an adult basis.

In addition, when the pharmaceutical composition is a plasmid vector, the pharmaceutical composition may be administered at a concentration of 0.1 µg/1 µl to 1 mg/1 µl per day on an adult basis. In addition, when the pharmaceutical composition is a plasmid vector, the dose may include 0.1 ml, 1 ml, 2 ml, 3 ml, 4 ml, 5 ml, 6 ml, 7 ml, 8 ml, 9 ml, 10 ml or higher, and include all values and ranges therebetween.

In still yet another aspect of the present invention, there is provided a pharmaceutical composition for preventing or treating cardiac arrhythmia, comprising a CCN5 protein as an active ingredient. The pharmaceutical composition may further comprise a SERCA2a protein. The CCN5 protein and the SERCA2a protein are as described above.

The pharmaceutical composition of the present invention is parenterally administered, and the parental administration includes intravenous injection, subcutaneous injection, intramuscular injection, intraperitoneal injection, transdermal administration, method for direct injection into tissue, and the like.

As used herein, the term "acceptable carrier" refers to some or all of the following substances and includes those suitable for a particular dose: solvents, diluents, liquid vehicles, dispersants, suspension adjuvants, surfactants, isotonic agents, thickeners, emulsifiers, preservatives, solid binders, lubricants, or the like. Alfanso R. Gennaro, Remington's Pharmaceutical Sciences, 19$^{th}$ edition, 1995, Macna Publishing Co. Easton, Pa. presents various carriers for use in pharmaceutical compositions with known techniques and compositions. Examples of pharmaceutical composition of pharmaceutically acceptable carriers include, but are not limited to, the following: glucose, sucrose sugar, starch such as corn starch and potato starch, cellulose and derivatives thereof such as sodium carboxymethyl cellulose, ethyl cellulose, and cellulose acetate; tragacanth in powder form; malt; gelatin; talc; excipients such as cocoa butter, suppository wax, peanut butter, cottonseed oil, safflower oil, sesame oil, olive oil, and soybean oil; glycols such as propylene glycol; esters such as ethyl oleate and ethyl laurate; agar; buffers such as magnesium hydroxide and aluminum hydroxide; alginic acid; pyrogen-free distilled water; isotonic saline; Ringer's solution; ethyl alcohol and phosphate buffered water, sodium lauryl sulfate and magnesium stearate, colorants, colorants, releasing agents, coating agents, sweeteners, flavoring agents and fragrances, antioxidants, and the like may be contained at the compound manufacturer's discretion.

In still yet another aspect of the present invention, there is provided a method for preventing or treating cardiac arrhythmia, comprising a step of administering, to a subject, a pharmaceutical composition of the present invention.

The pharmaceutical composition may be a pharmaceutical composition for preventing or treating cardiac arrhythmia which comprises, as an active ingredient, a gene construct that contains a nucleotide sequence encoding a CCN5 protein or a fragment thereof. In addition, the pharmaceutical composition may be a pharmaceutical composition for preventing or treating cardiac arrhythmia which comprises, as an active ingredient, an expression vector loaded with a nucleotide sequence encoding a CCN5 protein or a fragment thereof. Furthermore, the pharmaceutical composition may be a pharmaceutical composition for preventing or treating cardiac arrhythmia which comprises, as an active ingredient, a recombinant virus that contains a nucleotide sequence encoding a CCN5 protein or a fragment thereof.

Here, the subject may be a mammal, preferably a human. Specifically, the subject may be a human or another mammal that is suffering from or may be at risk of cardiac arrhythmia.

In still yet another aspect of the present invention, there is provided a method for preventing or treating cardiac arrhythmia, comprising administering CCN5 protein to a subject. Additionally, the method may further comprise administering SERCA2a protein to the subject.

Here, the subject may be a mammal, preferably a human. Specifically, the subject may be a human or another mammal that is suffering from or may be at risk of cardiac arrhythmia.

In still yet another aspect of the present invention, there is provided a method for preventing or treating cardiac arrhythmia, comprising administering, to a subject, a gene construct that contains a nucleotide sequence encoding CCN5 protein or a fragment thereof and a gene construct that contains a nucleotide sequence encoding SERCA2a protein or a fragment thereof.

Here, the subject may be a mammal, preferably a human. Specifically, the subject may be a human or another mammal that is suffering from or may be at risk of cardiac arrhythmia.

In still yet another aspect of the present invention, there is provided a method for preventing or treating cardiac arrhythmia, comprising administering, to a subject, an expression vector loaded with a nucleotide sequence encoding a SERCA2a protein or a fragment thereof and an expression vector loaded with a nucleotide sequence encoding a CCN5 protein or a fragment thereof.

Here, the subject may be a mammal, preferably a human. Specifically, the subject may be a human or another mammal that is suffering from or may be at risk of cardiac arrhythmia.

In still yet another aspect of the present invention, there is provided a method for preventing or treating cardiac arrhythmia, comprising administering, to a subject, a recombinant virus that contains a nucleotide sequence encoding a SERCA2a protein or a fragment thereof and a recombinant virus that contains a nucleotide sequence encoding a CCN5 protein or a fragment thereof.

Here, the subject may be a mammal, preferably a human. Specifically, the subject may be a human or another mammal that is suffering from or may be at risk of cardiac arrhythmia.

In still yet another aspect of the present invention, there is provided a use of the pharmaceutical composition of the present invention for preventing or treating cardiac arrhythmia.

In still yet another aspect of the present invention, there is provided a use of the pharmaceutical composition of the present invention for manufacture of a medicament for preventing or treating cardiac arrhythmia.

The pharmaceutical composition may be a pharmaceutical composition for preventing or treating cardiac arrhythmia which comprises, as an active ingredient, a gene construct that contains a nucleotide sequence encoding a CCN5 protein or a fragment thereof. In addition, the pharmaceutical composition may be a pharmaceutical composition for preventing or treating cardiac arrhythmia which comprises, as an active ingredient, an expression vector loaded with a nucleotide sequence encoding a CCN5 protein or a fragment thereof. Furthermore, the pharmaceutical composition may be a pharmaceutical composition for preventing or treating cardiac arrhythmia which comprises, as an active ingredient, a recombinant virus that contains a nucleotide sequence encoding a CCN5 protein or a fragment thereof.

MODE FOR THE INVENTION

Hereinafter, the present invention will be described in detail by way of examples. However, the following experimental examples and examples are only for illustrating the present invention, and the present invention is not limited to the following preparation examples and examples.

Preparation Example 1. Construction of
AAV9-CCN5 and AAV9-SERCA2a-P2A-CCN5 pTR-CMV-CCN5 gene construct was constructed to express a CCN5 protein. In addition, pTR-CMV-SERC2a-P2A-CCN5 gene construct was constructed to simultaneously express a CCN5 protein and a SERCA2a protein (FIGS. 1 and 2).

In the gene construct, the SERCA2a moiety consists of a cDNA sequence of human SERCA2a protein. The next linked P2A moiety is a self-cleavage site derived from porcine teschovirus-1 and consists of a nucleotide sequence encoding 22 amino acids. Lastly, the CCN5 moiety consists of a cDNA sequence of human CCN5 protein.

pTR-CMV-SERCA2a-P2A-CCN5 recombinant plasmid was constructed by removing the luciferase moiety from pTR-CMV-luciferase vector and inserting the SERCA2a-P2A-CCN5 gene construct in place thereof. The protein produced by the recombinant plasmid is divided into the SERCA2a moiety and the CCN5 moiety by self-cleavage between the $21^{st}$ amino acid, glycine, and the $22^{nd}$ amino acid, proline, at the P2A site. The SERCA2a moiety may remain in the endoplasmic reticulum membrane and perform its intrinsic function. In addition, the CCN5 moiety may migrate into the endoplasmic reticulum and then be secreted out of the cell in the form in which the signal peptide is cleaved, thereby performing its intrinsic function.

Human CCN5 gene was cloned into pds-AAV2-EGFP vector to construct adeno-associated virus (AAV, serotype 9). In order to improve virus packaging and viral delivery efficiency, eGFP sequence was removed during AAV vector construction. Recombinant AAV was constructed using 293T cells. AAV particles in a cell culture were collected and precipitated with ammonium sulfate. The resultant was purified by ultracentrifugation using iodixanol gradient. The AAV particles were enriched through several dilution and enrichment processes in such a manner that iodixanol is exchanged with lactated Ringer's solution using centrifugation. The AAV concentration was quantified using quantitative RT-PCR and SDS-PAGE.

Experimental Method 1. Production of Experimental Model and Gene Introduction

Experimental Method 1.1. Production of Atrial Fibrillation Mouse Model Through Infusion of Angiotensin II into CCN5-Overexpressing Mouse Model For experiments, male C57BL6 WT (wild type, black hair color) mice and transgenic (TG) mice, in which CCN5 is cardiac-specifically overexpressed, were used.

The CCN5-TG mice were produced by subcloning mouse CCN5 gene in pNC vector (Clontech, USA) containing α-MHC promoter that induces cardiac-specific expression of a gene, and introducing the resultant into C57BL/6 fertilized eggs using microinjection technique. In addition, in order to acquire and maintain a significant line of mice, sequencing was commissioned to a company named Macrogen Inc. (South Korea). Southern blotting was used to identify presence of CCN5 transgene on the mouse genome.

All mice used were 8- to 10-week-old mice weighing 20 g to 25 g. The mice were anesthetized by intraperitoneal injection of ketamine (95 mg/kg) and xylazine (5 mg/kg), and atrial fibrillation was induced by subcutaneous infusion of angiotensin II. Here, angiotensin II was infused subcutaneously for 14 days at a concentration of 3.0 mg/kg per day using a small osmotic pump (Alzet 1002, Alzet).

Experiment Method 1.2. Production of Atrial Fibrillation Mouse Model Through Infusion of Angiotensin II and Virus Injection 8- to 10-week-old B6C3F1 (gray hair color) mice were anesthetized by intraperitoneal injection of ketamine (95 mg/kg) and xylazine (5 mg/kg), and atrial fibrillation was induced by subcutaneous infusion of angiotensin II. Here, angiotensin II was infused subcutaneously for 2 weeks at a concentration of 3 mg/kg per day using a small osmotic pump. 2 Weeks after induction of atrial fibrillation with angiotensin II infusion, each mouse was injected, via the tail vein, with $1\times10^{11}$ viral genomes (vgs) of AAV9-Control or AAV9-CCN5.

Experiment Method 1.3. Production of Ventricular Arrhythmia Mouse Model Through Infusion of Angiotensin II and Viral Gene Introduction 8- to 10-week-old B6C3F1 mice were anesthetized by intraperitoneal injection of ketamine (95 mg/kg) and xylazine (5 mg/kg), and ventricular arrhythmia was induced by subcutaneous infusion of angiotensin II. Angiotensin II was infused subcutaneously for 2 weeks at a concentration of 3 mg/kg per day using a small osmotic pump. 2 Weeks after induction of ventricular arrhythmia with angiotensin II infusion, each mouse was injected, via the tail vein, with $1\times10^{11}$ vgs of AAV9-Control, AAV9-CCN5, or AAV9-SERCA2a-P2A-CCN5.

Experimental Method 2. Tissue Staining

Cardiac tissues were taken from animal models and then fixed with 10% (w/v) formalin at room temperature for 5 days. Then, washing with PBS was performed. Each sample was embedded in paraffin and the tissue block was cut into 7 μm thick sections.

Masson trichrome staining was performed to measure degree of fibrosis. Tissue at the site where fibrosis has progressed is stained blue and normal tissue is stained red. Degree of fibrosis was expressed by calculating the portion in which fibrosis had occurred out of the entire tissue. This was observed under an optical microscope and analyzed using Aperio Imagescope (Leica Biosystems) program.

Experimental Method 3. Identification of mRNA Expression Level Through Real-Time PCR Cardiac tissues were taken from animal models and then mRNAs were extracted therefrom to perform qRT-PCR. Real-time PCR was performed using QuantiTect SYBR Green real time PCR Kit (Qiagen Ltd). Through this, their transcription level was analyzed. RNA was isolated from the cardiac tissue using Trizol (Gibco BRL), and cDNA was synthesized therefrom. The quantitative real-time PCR condition was as follows: 37 cycles of 94° C. for 10 seconds, 57° C. for 15 seconds, 72° C. for 5 seconds. Information on primers used in the experiment is shown in Table 1.

TABLE 1

| Primer | Sequence information | SEQ ID NO |
|---|---|---|
| Mouseα-SMA-F | 5'-CCCACCCAGAGTGGAGAA-3' | SEQ ID NO: 13 |
| Mouseα-SMA-R | 5'-ACATAGCTGGAGCAGCGTCT-3 | SEQ ID NO: 14 |
| Mouse Collagen I-F | 5'-CATGTTCAGCTTTGTGGACCT-3" | SEQ ID NO: 15 |
| Mouse Collagen I-R | 5'-GACGCTGACTTCAGGGATGT-3' | SEQ ID NO: 16 |
| Mouse TGF-β1-F | 5'-TGGAGCAACATGTGGAACTC-3' | SEQ ID NO: 17 |

TABLE 1-continued

| Primer | Sequence information | SEQ ID NO |
|---|---|---|
| Mouse TGF-β1-R | 5'-CAGCAGCCGGTTACCAAG-3' | SEQ ID NO: 18 |
| Mouse IL-1β-F | 5'-TCCAGGATGAGGACATGATGAGCA-3' | SEQ ID NO: 19 |
| Mouse IL-1β-R | 5'-GAACGTCACACACACCAGCAGGTTA-3' | SEQ ID NO: 20 |
| Mouse RANTES-F | 5'-TGCAGAGGACTCTGAGACAGC-3' | SEQ ID NO: 21 |
| Mouse RANTES-R | 5'-GAGTGGTGTCCGAGCCATA-3' | SEQ ID NO: 22 |
| Mouse F4/80-F | 5'-CCTGGACGAATCCTGTGAAG-3' | SEQ ID NO: 23 |
| Mouse F4/80-R | 5'-GGTGGGACCACAGAGAGTTG-3' | SEQ ID NO: 24 |
| Mouse MCP-1-F | 5'-CATCCACGTGTTGGCTCA-3' | SEQ ID NO: 25 |
| Mouse MCP-1-R | 5'-GATCATCTTGCTGGTGAATGAGT-3' | SEQ ID NO: 26 |
| Mouse CCN5-F | 5'-ATACAGGTGCCAGGAAGGTG-3' | SEQ ID NO: 27 |
| Mouse CCN5-R | 5'-GTTGGATACTCGGGTGGCTA-3' | SEQ ID NO: 28 |
| Mouse GAPDH-F | 5'-CTCATGACCACAGTCCATGC-3' | SEQ ID NO: 29 |
| Mouse GAPDH-R | 5'-TTCAGCTCTGGGATGACCTT-3' | SEQ ID NO: 30 |
| Mouse 18s rRNA-F | 5'-GTAACCCGTTGAACCCCATT-3' | SEQ ID NO: 31 |
| Mouse 18s rRNA-R | 5'-CCATCCAATCGGTAGTAGCG-3' | SEQ ID NO: 32 |
| Rat α-SMA-F | 5'-TCTGTCTCTAGCACACAACTGTGAATG-3' | SEQ ID NO: 33 |
| Rat α-SMA-R | 5'-TTGACAGGCCAGGGCTAGAAGGG-3' | SEQ ID NO: 34 |
| Rat Collagen I-F | 5'-AATGCACTTTTGGTTTTTGGTCACGT-3' | SEQ ID NO: 35 |
| Rat Collagen I-R | 5'-CAGCCCACTTTGCCCCAACCC-3' | SEQ ID NO: 36 |
| Rat TGF-β1-F | 5'-TGTTCGCGCTCTCGGCAGTG-3' | SEQ ID NO: 37 |
| Rat TGF-β1-R | 5'-CGGATGGCCTCGATGCGCTT-3' | SEQ ID NO: 38 |
| Rat GAPDH-F | 5'-ACCCAGCCCAGCAAGGATACTG-3' | SEQ ID NO: 39 |
| Rat GAPDH-R | 5'-ATTCGAGAGAAGGGAGGGCTCCC-3' | SEQ ID NO: 40 |

Experimental Method 4. Electrophysiological Experimental Method

Experimental Method 4.1. Electrocardiogram Measurement in Atrial Fibrillation Model Using CCN5 TG Mice For atrial electrophysiology studies, experiments were performed ex vivo by connecting the removed mouse heart to the Langendorff system. The removed heart was perfused with Krebs-Henseleit buffer (118 mM NaCl, 4.7 mM KCl, 1.2 mM $MgSO_4$, 1.25 mM $CaCl_2$), 1.2 mM $KH_2PO_4$, 25 mM $NaHCO_3$, 11 mM glucose), and 95% $O_2$/5% $CO_2$ gas, temperature of 37° C., and pressure of 60 mmHg were maintained. Before applying an electrical stimulus, the removed heart was stabilized for 10 minutes by being connected to the Langendorff system. Then, the Teflon-coated silver bipolar electrode was placed in the right atrium, the left atrium, and the left ventricle. In order to induce atrial fibrillation, 2-second burst pacing was performed three times using an automatic stimulator. In the first 2-second burst pacing, a stimulus was applied at a cycle length of 40 ms with a pulse duration of 5 ms. After the application of a stimulus, stabilization was performed for 3 minutes. The second 2-second burst was applied at a cycle length of 20 ms with a pulse duration of 5 ms, and stabilization was performed again for 3 minutes. The last 2-second burst was applied at a cycle length of 20 ms with a pulse duration of 10 ms. The atrium, which showed an irregular R-R interval for at least 1 second and showed an irregular, rapid rhythm, was determined to have atrial fibrillation.

Experimental Method 4.2. Measurement of Electrocardiogram in Atrial Fibrillation Mice Injected with AAV9-CCN5

Experiments were performed ex vivo by connecting the removed mouse heart to the Langendorff system as performed in Experimental Method 4.1. Specifically, heparin was first administered to the mice to prevent blood coagulation, and the mice were anesthetized using 100% isoflurane (Forane, USP, Baxter Healthcare Corporation). Thereafter, the mouse heart was extracted and connected to the Langendorf system. The heart was mounted via the aorta to a cannula, perfused with Tyrode solution (NaCl 130 mM, $NaHCO_3$ 24 mM, KCl 4 mM, $MgCl_2$ 1 mM, $CaCl_2$) 1.8 mM, $KH_2PO_4$ 1.2 mM, $C_6H_{12}O_6$ 5.6 mM, 1% albumin) at a flow of 1.5 to 2.0 $min^{-1}$, and 95% $O_2$/5% $CO_2$ gas, temperature of 38±1° C., pH 7.3 to pH 7.5, and pressure of 60 mmHg to 70 mmHg (Pressure Monitor BP-1, World Precision Instruments) were maintained. An electro-mechanical decoupler (5 mM Blebbistatin, Sigma Aldrich, USA) was used to minimize mechanical contraction of the heart.

A custom-made Ag—AgCl pacing electrode was placed in the right atrium, and the other electrode was fixed to both epicardial surfaces and to the cardiac septum. The anterior surface of the heart was used to continuously map electrical activity in the left atrium in a semi-vertical manner (Mightex BioLED Light, Source Control Module, BLS Series).

Volumetric electrocardiography was performed to determine arrhythmia. Amplification and low-pass filtration were performed at 150 Hz using an electronic amplifier to continuously record the volumetric electrocardiogram of the heart. In addition, digital sampling was performed at a rate of 1 kHz (BioPac Systems MP150). In order to identify occurrence of persistent arrhythmia with electrical and optical signals, the pacing began at a fundamental frequency of 7 Hz (PCL=140 ms) in the right atrium with gradually increasing the frequency while applying a 2 ms stimulus duration with a frequency of 2 Hz to 3 Hz.

Experimental Method 4.3. Experimental Method for Optical Mapping in Atrial Fibrillation and Ventricular Arrhythmia Mouse Models The heart was stained by injecting, in the vicinity of the aorta, 0.3 ml of 15 μM voltage sensitive dye (Di-4-ANEPPS, Invitrogen, Thermofisher Scientific) when, 20 to 30 minutes after initiating back perfusion of the heart, the heartbeat reached a steady state of 4 Hz to 5 Hz. Monochromatic light (Mightex, BioLED) was used to excite fluorophores at a wavelength of 530 nm. The emitted wavelengths were filtered through a long pass band filter (>590 nm) and projected with a spatial resolution of 87.5 μm, a frame rate of 1 kHz, and an 80×80 pixel CCD chip (SciMeasure, SciMeasure Analytical Systems, USA) at a total magnification of 3×.

The collected raw data was processed by custom-made software written in MATLAB (The Mathworks, Inc.) optimized for the mouse heart by selecting a frame. In order to improve the signal-to-noise ratio and decrease variability with heartbeat, an average was calculated for 8 to 10 consecutive beats in the paced rhythm. Images were spatially averaged using a 5×5 uniform kernel at each pixel, and the baseline was subtracted therefrom. Then, the resultant was normalized to maximum amplitude and inverted. The point where the membrane potential threshold value exceeded 0.5 for at least 10 consecutive frames was determined as activation time.

Experimental Method 5. Western Blotting

The cells used and the heart obtained in the present experiments were prepared using homogenized RIPA buffer (0.1% (w/v) SDS, 50 mM Tris-HCl (pH 7.4), 150 mM NaCl, 1% (w/v) NP-40, 0.5% (w/v) sodium deoxycholate) supplemented with broad-spectrum protease inhibitor cocktail (Calbiochem). Proteins were separated by size using SDS-PAGE gels and transferred to PVDF membrane (Millipore). After being blocked with 5% (w/v) skim milk for 1 hour and washed with TBST, the prepared membrane was allowed to react with p-CaMKII, CaMKII, $Na^+/Ca^+$ exchanger 2 (NCX2), RyR2 (Santa Cruz), pRyR2 (Ser2808), pRyR2 (Ser2814) (Badrilla), GAPDH (laboratory-made), α-tubulin, TGF-β1, α-SMA (Sigma), Collagen I (Rockland), NaV 1.5, Connexin 43, Kir2.1 (Alomone labs), fibroblast activation protein (FAP), mitochondrial peptide methionine sulfoxide reductase (MsrA), Tubulin (Abcam), SERCA2a ($21^{st}$ Century Biochemicals), Smad7 (Invitrogen), and CCN5 (Genescipt) antibodies. The membrane was then reacted with horseradish peroxidase-conjugated secondary antibody (Jackson ImmunoResearch, West Grove, Pa., USA) and developed using a chemiluminescent substrate (Dogen). Blots were scanned and quantified using LAS software.

Experimental Method 6. Isolation and Culture of Atrial Fibroblasts

The heart of Sprague Dawley (SD) white rats was used to isolate fibroblasts from the atrium of the white rats. The left atrium was degraded into single cells by digesting the tissue using a collagenase solution. The cells collected from the atrium were first centrifuged at 50×g for 3 minutes. The thus obtained supernatant was collected and centrifuged again at 500×g for 10 minutes. The thus obtained cell layer was cultured using a DMEM culture containing 10% fetal bovine serum (FBS) and 1% antibiotics. After 2 to 3 days, the culture was subjected to treatment with 100 nM angiotensin II and simultaneously with control conditioned media (CM-Con) or CCN5-containing conditioned media (CM-CCN5). After 48 hours, the experiment was terminated. For clear experimental results, only the left atrial fibroblasts obtained from the first passage were used as left atrial fibroblasts.

Experimental Method 7. Preparation of CM-CCN5

In order to prepare the CM-CCN5, pcDNA3.1-CCN5HA plasmid was used. HEK293 cells were dispensed at $5 \times 10^5$ cells in a 60-mm culture dish and stabilized for one day. Then, transfection of pcDNA3.1-CCN5HA was performed using lipofectamine (Invitrogen). After 4 hours, medium exchange was performed to remove lipofectamine. Then, culture was performed for 24 hours, and the obtained culture medium was named CM-CCN5.

Experimental Method 8. Fluorescence Immunochemistry 15,000 cells were dispensed on a 16-mm cover slip and incubated overnight for stabilization. Then, the cells were subjected to treatment with 100 nM angiotensin II and with CM-Con or CM-CCN5, and incubation was performed. The resulting cells were fixed with 4% (w/v) paraformaldehyde solution, allowed for the cell membrane to have permeability using 0.5% Triton X-100 solution, and then blocked with 5% (w/v) BSA solution. Then, reaction was allowed to proceed with anti-α-SMA (Sigma) antibody, and an Alexa Fluor 488-conjugated antibody (Invitrogen) was used as a secondary antibody. Nuclei were stained using Hoechst dye. For the cells which had been subjected to immunochemistry, Fluoview FV 1000 confocal microscope was used.

Experimental Method 9. Measurement of Myocardial Function Through Echocardiography Mice were anesthetized by intraperitoneal injection of ketamine (95 mg/kg) and xylazine (5 mg/kg), and echocardiography was conducted. Recording was performed through 2-dimensional imaging and M-mode tracking function, and fractional shortening and ventricular size ratio were determined (GE Vivid Vision).

Experimental Example 1. Identification of Therapeutic Effect of CCN5 Protein in Atrial Fibrillation Mouse Model

Experimental Example 1.1. Identification of Atrial Fibrosis Inhibitory Effect of CCN5 Protein Angiotensin II was infused subcutaneously into the WT mice and the CCN5 TG mice produced by the method described in Experimental Method 1.1, for 14 days at a concentration of 3.0 mg/kg per day using a small osmotic pump (Alzet 1002, Alzet). After 2 weeks, the mouse heart was extracted. Tissue staining was performed by the method described in Experimental Method 2, to identify degree of fibrosis (FIG. 3a).

As a result, in the control mouse group injected with angiotensin II, it was observed that collagen was accumulated in about 8% of the atrial tissues; on the other hand, in the CCN5 TG mouse group injected with angiotensin II, the collagen accumulation was observed in about 4% of the atrial tissues, indicating a significant decrease (FIGS. 3*b* and 3*c*).

In addition, in order to identify changes occurring in mRNA expression, mRNA was extracted from the mouse left atrium and qRT-PCR was performed by the method described in Experimental Method 3.

As a result, for the cardiac fibrosis marker genes, α-SMA, Collagen I, and TGF-β1, and the inflammatory response marker genes, IL-1β, RANTES (Regulated on Activation, Normal T cell Expressed and Secreted), F4/80, monocyte chemoattractant protein 1 (MCP-1), their mRNA expression was increased in the control mouse group injected with angiotensin II; on the other hand, expression of these marker genes was significantly decreased in the CCN5 TG mouse group injected with angiotensin II (FIGS. 3*d* to 3*j*). From these results, it was identified that CCN5 was effective in inhibiting atrial fibrosis caused by angiotensin II.

Experimental Example 1.2. Identification of Atrial Fibrillation Inhibitory Effect of CCN5

For atrial electrophysiology studies, experiments were performed ex vivo by connecting the removed mouse heart to the Langendorff system in the same manner as in Experiment 4.1. As a result, in the WT mice injected with angiotensin II, atrial fibrillation was induced in 4 out of 6 animals. However, in the CCN5 TG mice injected with angiotensin II, all 4 animals showed normal electrocardiogram results even after an electrical stimulus (FIGS. 4*b* and 4*c*). From these results, it was identified that CCN5 inhibited atrial fibrillation caused by angiotensin II.

Experimental Example 1.3. Identification of Regulation of Intracellular $Ca^{2+}$ Concentration by CCN5

The presumption that CCN5 regulates $Ca^{2+}$ in cardiomyocytes was investigated using HL-1 cells (Sigma) that is a mouse atrial cardiomyocyte cell line. In addition, western blotting was used to identify its regulatory effect on $Ca^{2+}$ concentration in the cultured HL-1 cells.

In cellular-level experiments, in order to identify the effect of CCN5, CM-CCN5 prepared by the method described in Experimental Example 8 was used. The HL-1 cells were subjected to treatment with angiotensin II and simultaneously with CM-Con (control) or CM-CCN5 (experimental group). After 48 hours, changes in protein levels were monitored with western blotting (FIG. 5*a*).

As a result, it was found that CaMKII phosphorylation (Thr287) increased when the HL-1 cells were subjected to treatment with 400 nM angiotensin II, whereas CaMKII phosphorylation decreased in the cells which had been subjected to simultaneous treatment with CM-CCN5. In the HL-1 cells which had been subjected to treatment with angiotensin II, hyperphosphorylation of the sarcoplasmic reticulum ryanodine receptor2 (RyR2) at Ser2808 and Ser2814 was induced; however, such hyperphosphorylation was inhibited by CCN5. Increased expression of $Na^+/Ca^+$ exchanger 2 (NCX2) caused by angiotensin II was also decreased by CCN5. An expression level of calsequestrin 2, a calcium-binding protein in the sarcoplasmic reticulum, was decreased by angiotensin II, whereas its expression was increased in the cells which had been subjected to simultaneous treatment with CM-CCN5 (FIGS. 5*b* to 5*g*). From these results, it was identified that CCN5 directly regulated cardiomyocytes and thus was involved in atrial fibrillation.

Experimental Example 1.4. Identification of Atrial Fibrosis Inhibitory Effect of CCN5 In Vitro The heart of Sprague Dawley (SD) white rats was used to isolate fibroblasts from the atrium. Atrial fibroblasts were isolated by the method described in Experimental Method 6. After 2 to 3 days, the isolated atrial fibroblasts were subjected to treatment with 100 nM angiotensin II simultaneously with control conditioned media (CM-Con) or CCN5-containing conditioned media (CM-CCN5) prepared in Experimental Example 8. After 48 hours, the experiment was terminated (FIG. 6*a*). The fibroblasts, which had been subjected to treatment with angiotensin II and with CM-Con or CM-CCN5, were subjected to fluorescence immunocytochemistry in the same manner as in Experimental Method 8.

As a result, the fibroblasts, which had been subjected to treatment with 100 nM angiotensin II, differentiated into myofibroblasts and expressed the myofibroblast-specific marker protein α-SMA, whereas the fibroblasts, which had been subjected to simultaneous treatment with CM-CCN5, did not express α-SMA at all (FIG. 6*b*).

In addition, the cultured atrial fibroblasts were subjected to western blotting according to the method described in Experimental Method 5, to identify the atrial fibrosis inhibitory effect. As a result, the fibroblasts, which had been subjected to treatment with angiotensin II, exhibited increased expression of the proteins, α-SMA, Collagen I, and TGF-β1, whereas the fibroblasts, which had been subjected to simultaneous treatment with CM-CCN5, exhibited remarkably decreased expression of these proteins (FIGS. 6*c* to 6*f*).

In addition, in order to identify an mRNA expression level of the cultured atrial fibroblasts, the atrial fibrosis inhibitory effect was monitored via qRT-PCR. As a result, it was identified that in the fibroblasts, which had been subjected to treatment with angiotensin II and simultaneously with CM-CCN5, mRNA expression levels of α-SMA, Collagen I, and TGF-β1 were decreased to a control level (FIGS. 6*g* to 6*i*). From these results, it was identified that CCN5 not only regulated fibrosis and thus inhibited atrial fibrillation, but also directly regulated cardiomyocytes and thus was involved in atrial fibrillation.

Experimental Example 1.5. Identification of Atrial Fibrosis Inhibitory Effect of AAV-CCN5 in Atrial Fibrillation Mouse Model In the same manner as Experimental Method 1.2, angiotensin II was infused into 8- to 10-week-old mice at a concentration of 3 mg/kg/day. At a time point of 2 weeks, AAV9-Control (control) or AAV9-CCN5 (comparative group) were injected, in an amount of 5×10" viral genomes (vgs), into the tail vein. After 4 weeks, the atrial tissue was subjected to Masson's Trichrome staining and molecular analyses (FIG. 7*a*).

First, in order to identify whether AAV9 virus was well expressed in a cardiac-specific manner, western blotting was used to identify expression of CCN5 in the atrial tissue. As a result, it was identified that CCN5 protein was overexpressed in the mouse group injected with AAV9-CCN5. In addition, from the results obtained by identifying the mRNA expression level of CCN5 in the atrial tissue, it was found that the mRNA of CCN5 was similarly increased by injection of AAV9-CCN5 (FIGS. 7b and 7c).

From the results obtained by identifying degree of atrial collagen accumulation through Trichrome staining, it was identified that in the mice injected with angiotensin II followed by AAV9-control, collagen was accumulated in about 6% of the atrial tissue, whereas, in the mouse group injected with AAV9-CCN5, the degree of collagen accumulation was decreased to about 3% (FIGS. 7d and 7e).

In addition, qRT-PCR was performed using the atrial tissue in the same manner as in Experimental Method 3, to identify mRNA expression levels of the fibrosis-related marker genes, α-SMA, Collagen I, and TGF-β1, and the inflammation-related marker genes, IL-113, RANTES, F4/80, and MCP-1. As a result, it was found that AAV9-CCN5 significantly decreased these marker genes whose expression level had been increased by angiotensin II (FIGS. 7f to 7l). From these results, it was identified that even in the mouse model in which CCN5 had been overexpressed in a cardiac-specific manner using AAV9-CCN5, angiotensin II-induced atrial fibrosis was effectively inhibited.

Experimental Example 1.6. Identification of Atrial Fibrillation Inhibitory Effect Exhibited by AAV9-CCN5

A mouse model was produced in the same manner as in Experimental Method 4.2, and cardiophysiology experiments were performed at the end of Week 6 (FIG. 8a). First, electrocardiogram was checked, and as a result, it was identified that in the mouse group injected with AAV9-Control, the atrial function was weakened by angiotensin II and thus atrial fibrillation was persistently induced after an electrical stimulus. On the other hand, it was observed that in the mouse group injected with AAV9-CCN5, the heartbeat returned to normal rhythm after an electrical stimulus. Even in experiments in which action potential of $Ca^{2+}$ (optical signal) was measured, the group injected with AAV9-Control persistently showed conduction irregularities after a stimulus, whereas the group injected with AAV9-CCN5 showed normal atrial activation after a stimulus (FIGS. 8b and 8c).

As a result of electrocardiogram analysis, in the mouse group injected with AAV9-Control, atrial fibrillation was induced in 4 out of 5 mice after an electrical stimulus, whereas in the mouse group injected with AAV9-CCN5, 2 out of 5 mice showed atrial abnormalities and the rest showed normal atrial activation (FIG. 8d).

While conducting electrocardiogram experiments, when an electrical stimulus was applied to induce atrial fibrillation, control (Sham) mouse group required a stimulus of about 28 Hz to induce atrial fibrillation; however, in the control mouse group injected with angiotensin II and AAV9-Control, atrial fibrillation was sufficiently induced even at a stimulus as low as about 20 Hz. On the other hand, it was found that in the mouse group injected with angiotensin II and AAV9-CCN5, atrial fibrillation was induced only when the stimulus was raised to about 25 Hz which was a similar level to the Sham group (FIG. 8e).

As mentioned in Experimental Method 4.2, electrical activity in the left atrium was mapped to graphically represent action potential of $Ca^{2+}$. The graph was analyzed at each time point of action potential duration 50 ($APD_{50}$) and action potential duration 75 ($APD_{75}$) thereon. As a result, it was identified that in the group injected with AAV9-CCN5, the action potential durations appeared at a rate similar to the Sham group, as compared with the group injected with AAV9-Control (FIG. 8f).

For each group, a slope of the graph in FIG. 8e was analyzed. This indicates the velocity required for action potential depolarization, and it was found that in the mouse group injected with AAV9-CCN5, the velocity required for depolarization which had been slowed by angiotensin II was restored to a level similar to Sham (FIG. 8g). From these results, it was identified that even in the mouse group into which CCN5 was overexpressed through injection of AAV9-CCN5, atrial fibrillation induced by angiotensin II was reliably inhibited.

Experimental Example 2. Identification of Therapeutic Effect of AAV-CCN5 and AAV9-SERCA2a-P2A-CCN5 in Ventricular Arrhythmia Mouse Model Experimental Example 2.1. Production of Ventricular Arrhythmia Mouse Model A ventricular arrhythmia mouse model was produced by the method described in Experimental Method 1.3. Male B6C3F1 WT (wild type, gray hair color) mice used were 8- to 10-week-old mice weighing 20 to 25 g. Angiotensin II was infused subcutaneously for 2 weeks at a concentration of 3 mg/kg. After 2 weeks, changes in heart function were identified by echocardiography. The identified mice were randomly selected and injected with CCN5 vector alone (AAV9-CCN5) or CCN5 and SERCA2a vector combination (AAV9-SERCA2a-P2A-CCN5) in an amount of $5 \times 10^{11}$ viral genomes (vgs). Then, these mice were maintained for 4 more weeks for final functional evaluation.

First, in order to identify that a ventricular arrhythmia mouse model had been well produced by angiotensin II, the cardiac function in the control mouse group (Sham) and the comparative mouse group (AngII) was checked by echocardiography. As a result, the mouse group, into which angiotensin II had been subcutaneously injected, showed decreased fractional shortening as compared with the control (Sham). However, the two groups did not show a great difference in terms of mouse weight (FIG. 9a).

In order to determine ventricular tachycardia, optical mapping was performed by applying, to the right ventricle (RV), an electrical stimulus of 10 Hz (FIG. 9b) or an electrical stimulus of 20 Hz (FIG. 9c), in the same manner as in Experimental Method 4.3. The greater the electrical stimulus, the more pronounced difference was observed between the experimental group and the control. In the mouse group injected with angiotensin II, when an electrical stimulus of 20 Hz was applied, the calcium ion channel or the like was not locally restored to its original state, and thus discontinuity in stimulus transmission was observed. The action potential of calcium was graphically represented and is illustrated in FIG. 9d. The graph was analyzed at each time point of action potential duration 50 ($APD_{50}$) and action potential duration 75 ($APD_{75}$) thereon. As a result, it was found that faster action potential duration was achieved by injection of angiotensin II (FIG. 9e). In addition, a significant decrease in dispersion rate of action potential duration was observed in the angiotensin II group (FIG. 9O. As a result of analyzing the conduction velocity and the velocity required for action potential depolarization, it was found that such velocities were greatly decreased by angiotensin II (FIG. 9g). From these results, it was identified that a ventricular arrhythmia mouse model was reliably produced by angiotensin II.

Experimental Example 2.2. Effect on β-Adrenergic Receptor Antagonists in

Ventricular Arrhythmia Mouse Model Isoproterenol (ISO) is a drug that clinically acts on β-adrenergic receptors and thus increases myocardial contractility, thereby increasing cardiac output. In the angiotensin II-induced ventricular arrhythmia mouse model, the action potential of $Ca^{2+}$ in the ventricle was identified when isoproterenol was used to stimulate β receptors (FIG. 10a). An electrical stimulus of 20 Hz was applied to the right ventricle, and the resulting repolarization pattern of $Ca^{2+}$ was shown in diagram.

As a result, it was identified that in the mouse model injected with angiotensin II, repolarization pattern of calcium was slower even with ISO treatment (FIG. 10b). As a result of analyzing the action potential duration 75 ($APD_{75}$), it was found that in the mouse model injected with angiotensin II, ISO treatment made no difference in action potential duration rate (FIG. 10c).

In order to determine ventricular tachycardia, optical mapping was performed by applying, to the right ventricle (RV), an electrical stimulus of 20 Hz, in the same manner as in Experimental Method 4.3. As a result, the angiotensin II mouse group treated with ISO showed discontinuity in conduction block with a stimulus, as compared with the control mouse group treated with ISO (FIG. 10d). As a result of analyzing the action potential duration 75 ($APD_{75}$), as compared with the Sham group, the angiotensin II-treated mouse group showed significantly increased action potential duration but showed insignificant changes with the ISO treatment (FIG. 10e). As a result of analyzing the conduction velocity, it was identified that the mouse group injected with angiotensin II showed much slower velocity as compared with Sham and the ISO treatment did not result in the restoration of the conduction velocity (FIG. 10f). From these results, it was found that injection of angiotensin II made β-adrenergic receptors insensitive to a stimulus.

Experimental Example 2.3. Identification of Therapeutic Effect of AAV9-CCN5 and AAV9-SERCA2a-P2A-CCN5 in Ventricular Arrhythmia Mouse Model A ventricular arrhythmia model was reliably produced by the experimental method as described in Experimental Example 2.3. Angiotensin II was injected into the mice for 2 weeks, and at the end of Week 2, AAV9-CCN5 or AAV9-SERCA2a-P2A-CCN5 vector was injected into the mouse tail vein. After 6 weeks in total, the experiment was terminated and ventricular arrhythmia-related experiments were performed.

Echocardiography was performed to identify the cardiac function affected by AAV9-CCN5 and AAV9-SERCA2a-P2A-CCN5 in an angiotensin II-induced ventricular arrhythmia mouse model. Injection of AAV9-CCN5 or AAV9-SERCA2a-P2A-CCN5 caused the fractional shortening, which had been decreased by angiotensin II, to exhibit fractional shortening which is a Sham level. In addition, as a result of analyzing the left ventricular wall thickness (LVSd), it was identified that the left ventricular wall thickness, which has been decreased by angiotensin II, was restored nearly to the normal level by AAV9-SERCA2a-P2A-CCN5 (FIGS. 11a and 11b).

The action potential of $Ca^{2+}$ was shown using optical mapping. It was found that when an electrical stimulus was applied to the ventricle with a stimulus of 20 Hz, conduction spread regularly in the mouse group injected with AAV9-CCN5 or AAV9-SERCA2a-P2A-CCN5, regardless of ISO treatment (FIGS. 11c and 11d). The action potential of calcium was graphically represented and is illustrated in FIG. 11e.

For respective Sham, AngII, AngII+AAV9-CCN5, AngII+AAV9-SERCA2a-P2A-CCN5 groups, treatment with ISO was performed and analysis was performed by drawing repolarization maps. As a result, it was identified that injection of AAV9-CCN5 or AAV9-SERCA2a-P2A-CCN5 caused the repolarization, which had been slowed by injection of angiotensin II, to exhibit repolarization having a similar pattern to Sham (FIG. 11f).

As a result of analyzing the action potential duration 75 ($APD_{75}$) of $Ca^{2+}$, it was found that the action potential duration, which had been increased by angiotensin II, was decreased by injection of AAV9-CCN5 (FIG. 11g) and was reliably decreased to the Sham level by AAV9-SERCA2a-P2A-CCN5. In addition, it was identified that the conduction velocity and depolarization velocity, which had been slowed by angiotensin II, were normalized by injection of AAV9-CCN5 or AAV9-SERCA2a-P2A-CCN5 (FIGS. 11h and 11i). From these results, it was identified that AAV9-CCN5 and AAV9-SERCA2a-P2A-CCN5 were effective in repairing ventricular arrhythmia induced by angiotensin II.

In addition, ventricular arrhythmia induced by programmed electrical stimulus (PES) was identified in the angiotensin II-injected model (FIG. 12a). As a result of analyzing stimulus frequency to induce ventricular arrhythmia, ventricular arrhythmia was induced even by low stimulus frequency in the AngII mouse group, whereas ventricular arrhythmia was induced by stimulus frequency, which was equal to or greater than a level of the Sham group, in the mouse group injected with AAV9-CCN5 or AAV9-SERCA2a-P2A-CCN5. As a result of analyzing incidence of ventricular arrhythmia, ventricular arrhythmia occurred at an episode rate of 5/5 in the AngII mouse group, at an episode rate of 1/5 in the AngII+AAV9-CCN5 mouse group, and at an episode rate of 0/5 in the AngII+AAV9-SERCA2a-P2A-CCN5 mouse group (FIGS. 12b and 12c).

Since cardiac arrhythmia is closely related to cardiac fibrosis, cardiac fibrosis was measured by Masson's Trichrome staining. As a result, it was found that cardiac fibrosis induced by angiotensin II was remarkably decreased in the heart into which AAV9-CCN5 or AAV9-SERCA2a-P2A-CCN5 had been injected (FIG. 13a).

In addition, this phenomenon is also closely associated with channel-related proteins that regulate electrical signals of the heart. Therefore, expression of $Na_v1.5$ and Connexin43 proteins in the heart tissue was checked by Western blotting. As a result, it was identified that decreased expression of channel-related proteins $Na_v1.5$ and Connexin43, which had been caused by angiotensin II, was restored by AAV9-SERCA2a-P2A-CCN5 (FIG. 13b). From these results, it was identified that gene therapy using CCN5 vector alone or co-expression of SERCA2A and CCN5 could also inhibit occurrence of ventricular tachycardia induced by angiotensin II.

The invention claimed is:

1. A method for treating cardiac arrhythmia, comprising: administering to a subject in need thereof,
   (i) a pharmaceutical composition comprising a recombinant nucleotide molecule that contains a nucleotide sequence encoding a cellular communication network factor 5 (CCN5) protein,
   (ii) a pharmaceutical composition comprising an expression vector loaded with a recombinant nucleotide molecule that contains a nucleotide sequence encoding a CCN5 protein,
   (iii) a pharmaceutical composition comprising a recombinant virus that contains a nucleotide sequence encoding a CCN5 protein, or
   (iv) a pharmaceutical composition comprising a CCN5 protein,
   wherein the CCN5 protein of (i), (ii), (iii), and (iv) comprises the amino acid sequence of SEQ ID NO: 1.

2. The method of claim 1, further comprising administering a sarcoplasmic/endoplasmic reticulum Ca2+ ATPase 2a (SERCA2a) protein to the subject.

3. The method of claim 1, wherein the nucleotide sequence encoding the CCN5 protein, of (i), (ii), and (iii), comprises the nucleotide sequence of SEQ ID NO: 2.

4. The method of claim 1, wherein the recombinant nucleotide molecule of (i) or (ii) contains a promoter sequence operatively linked to the nucleotide sequence encoding the CCN5 protein.

5. The method of claim 4, wherein the promoter is any one selected from the group consisting of CMV promoter, adenovirus late promoter, vaccinia virus 7.5K promoter, SV40 promoter, HSV tk promoter, RSV promoter, EF1 alpha promoter, metallothionein promoter, beta-actin promoter, human IL-2 gene promoter, human IFN gene promoter, human IL-4 gene promoter, human lymphotoxin gene promoter, and human GM-CSF gene promoter.

6. The method of claim 1, wherein the recombinant nucleotide molecule of (i) further contains a nucleotide sequence encoding a SERCA2a protein.

7. The method of claim 6, wherein in the recombinant nucleotide molecule, the nucleotide sequence encoding the SERCA2a protein is at the 5' end of the nucleotide sequence encoding the CCN5 protein.

8. The method of claim 7, wherein the recombinant nucleotide molecule contains a self-cleavage sequence located between the nucleotide sequence encoding the SERCA2a protein and the nucleotide sequence encoding the CCN5 protein.

9. The method of claim 8, wherein the self-cleavage sequence is a nucleotide sequence encoding 2A peptide derived from porcine teschovirus-1, *Thosea asigna* virus, equine rhinitis A virus, or foot-and-mouth disease virus.

10. The method of claim 8, wherein the self-cleavage sequence is a nucleotide sequence encoding 2A peptide derived from porcine teschovirus-1.

11. The method of claim 8, wherein the self-cleavage sequence is the nucleotide sequence of SEQ ID NO: 6.

12. The method of claim 1, wherein the expression vector of (ii) is further loaded with a nucleotide sequence encoding a SERCA2a protein.

13. The method of claim 12, wherein in the expression vector, the nucleotide sequence encoding the SERCA2a protein is at the 5' end of the nucleotide sequence encoding the CCN5 protein.

14. The method of claim 1, wherein the expression vector (ii) further contains a self-cleavage sequence located between the nucleotide sequence encoding the SERCA2a protein and the nucleotide sequence encoding the CCN5 protein.

15. The method of claim 1, wherein the expression vector of (ii) is any one selected from the group consisting of a plasmid vector and a cosmid vector.

16. The method of claim 1, wherein the recombinant virus of (iii) is any one selected from the group consisting of adenovirus, adeno-associated viruses (AAV), retrovirus, lentivirus, herpes simplex virus, and vaccinia virus.

17. The method of claim 1, wherein the recombinant virus of (iii) further contains a nucleotide sequence encoding a SERCA2a protein.

* * * * *

SEQUENCE LISTING

<160> NUMBER OF SEQ ID NOS: 42

<210> SEQ ID NO 1
<211> LENGTH: 250
<212> TYPE: PRT
<213> ORGANISM: Homo sapiens

<400> SEQUENCE: 1

Met Arg Gly Thr Pro Lys Thr His Leu Leu Ala Phe Ser Leu Leu Cys
1               5                   10                  15

Leu Leu Ser Lys Val Arg Thr Gln Leu Cys Pro Thr Pro Cys Thr Cys
            20                  25                  30

Pro Trp Pro Pro Pro Arg Cys Pro Leu Gly Val Pro Leu Val Leu Asp
        35                  40                  45

Gly Cys Gly Cys Cys Arg Val Cys Ala Arg Arg Leu Gly Glu Pro Cys
    50                  55                  60

Asp Gln Leu His Val Cys Asp Ala Ser Gln Gly Leu Val Cys Gln Pro
65                  70                  75                  80

Gly Ala Gly Pro Gly Gly Arg Gly Ala Leu Cys Leu Leu Ala Glu Asp
                85                  90                  95

Asp Ser Ser Cys Glu Val Asn Gly Arg Leu Tyr Arg Glu Gly Glu Thr
            100                 105                 110

Phe Gln Pro His Cys Ser Ile Arg Cys Arg Cys Glu Asp Gly Gly Phe
        115                 120                 125

Thr Cys Val Pro Leu Cys Ser Glu Asp Val Arg Leu Pro Ser Trp Asp
    130                 135                 140

Cys Pro His Pro Arg Arg Val Glu Val Leu Gly Lys Cys Cys Pro Glu
145                 150                 155                 160

Trp Val Cys Gly Gln Gly Gly Gly Leu Gly Thr Gln Pro Leu Pro Ala
                165                 170                 175

Gln Gly Pro Gln Phe Ser Gly Leu Val Ser Ser Leu Pro Pro Gly Val
            180                 185                 190

Pro Cys Pro Glu Trp Ser Thr Ala Trp Gly Pro Cys Ser Thr Thr Cys
        195                 200                 205

Gly Leu Gly Met Ala Thr Arg Val Ser Asn Gln Asn Arg Phe Cys Arg
    210                 215                 220

Leu Glu Thr Gln Arg Arg Leu Cys Leu Ser Arg Pro Cys Pro Pro Ser
225                 230                 235                 240

Arg Gly Arg Ser Pro Gln Asn Ser Ala Phe
                245                 250

<210> SEQ ID NO 2
<211> LENGTH: 750
<212> TYPE: DNA
<213> ORGANISM: Homo sapiens

<400> SEQUENCE: 2
atgagaggca caccgaagac ccacctcctg gccttctccc tcctctgcct cctctcaaag      60
gtgcgtaccc agctgtgccc gacaccatgt acctgcccct ggccaccctc ccgatgcccg     120 ctggagtac ccctggtgct ggatggctgt ggctgctgcc gggtatgtgc acggcggctg     180
ggggagccct gcgaccaact ccacgtctgc gacgccagcc agggcctggt ctgccagccc     240
ggggcaggac ccgtggcccg gggggccctg tgcctcttgg cagaggacga cagcagctgt     300
gaggtgaacg gccgctgta tcgggaaggg gagaccttcc agccccactg cagcatccgc     360
tgccgctgcg aggacggcgg cttcacctgc gtgccgctgt gcagcgagga tgtgcggctg     420

```
cccagctggg actgccccca ccccaggagg gtcgaggtcc tgggcaagtg ctgccctgag    480
tgggtgtgcg gccaaggagg gggactgggg acccagcccc ttccagccca aggaccccag    540
ttttctggcc ttgtctcttc cctgccccct ggtgtcccct gcccagaatg gagcacggcc    600
tggggaccct gctcgaccac ctgtgggctg ggcatggcca cccgggtgtc caaccagaac    660
cgcttctgcc gactggagac ccagcgccgc ctgtgcctgt ccaggccctg cccaccctcc    720
aggggtcgca gtccacaaaa cagtgccttc                                      750
```

```
<210> SEQ ID NO 3
<211> LENGTH: 997
<212> TYPE: PRT
<213> ORGANISM: Homo sapiens

<400> SEQUENCE: 3
```

```
Met Glu Asn Ala His Thr Lys Thr Val Glu Glu Val Leu Gly His Phe
1               5                   10                  15

Gly Val Asn Glu Ser Thr Gly Leu Ser Leu Glu Gln Val Lys Lys Leu
            20                  25                  30

Lys Glu Arg Trp Gly Ser Asn Glu Leu Pro Ala Glu Glu Gly Lys Thr
        35                  40                  45

Leu Leu Glu Leu Val Ile Glu Gln Phe Glu Asp Leu Leu Val Arg Ile
    50                  55                  60

Leu Leu Leu Ala Ala Cys Ile Ser Phe Val Leu Ala Trp Phe Glu Glu
65                  70                  75                  80

Gly Glu Glu Thr Ile Thr Ala Phe Val Glu Pro Phe Val Ile Leu Leu
                85                  90                  95

Ile Leu Val Ala Asn Ala Ile Val Gly Val Trp Gln Glu Arg Asn Ala
            100                 105                 110

Glu Asn Ala Ile Glu Ala Leu Lys Glu Tyr Glu Pro Glu Met Gly Lys
        115                 120                 125

Val Tyr Arg Gln Asp Arg Lys Ser Val Gln Arg Ile Lys Ala Lys Asp
    130                 135                 140

Ile Val Pro Gly Asp Ile Val Glu Ile Ala Val Gly Asp Lys Val Pro
145                 150                 155                 160

Ala Asp Ile Arg Leu Thr Ser Ile Lys Ser Thr Thr Leu Arg Val Asp
                165                 170                 175

Gln Ser Ile Leu Thr Gly Glu Ser Val Ser Val Ile Lys His Thr Asp
            180                 185                 190

Pro Val Pro Asp Pro Arg Ala Val Asn Gln Asp Lys Lys Asn Met Leu
        195                 200                 205

Phe Ser Gly Thr Asn Ile Ala Ala Gly Lys Ala Met Gly Val Val Val
    210                 215                 220

Ala Thr Gly Val Asn Thr Glu Ile Gly Lys Ile Arg Asp Glu Met Val
225                 230                 235                 240

Ala Thr Glu Gln Glu Arg Thr Pro Leu Gln Gln Lys Leu Asp Glu Phe
                245                 250                 255

Gly Glu Gln Leu Ser Lys Val Ile Ser Leu Ile Cys Ile Ala Val Trp
            260                 265                 270

Ile Ile Asn Ile Gly His Phe Asn Asp Pro Val His Gly Gly Ser Trp
        275                 280                 285

Ile Arg Gly Ala Ile Tyr Tyr Phe Lys Ile Ala Val Ala Leu Ala Val
    290                 295                 300

Ala Ala Ile Pro Glu Gly Leu Pro Ala Val Ile Thr Thr Cys Leu Ala
```

```
            305                 310                 315                 320
Leu Gly Thr Arg Arg Met Ala Lys Lys Asn Ala Ile Val Arg Ser Leu
                325                 330                 335

Pro Ser Val Glu Thr Leu Gly Cys Thr Ser Val Ile Cys Ser Asp Lys
                340                 345                 350

Thr Gly Thr Leu Thr Thr Asn Gln Met Ser Val Cys Arg Met Phe Ile
                355                 360                 365

Leu Asp Arg Val Glu Gly Asp Thr Cys Ser Leu Asn Glu Phe Thr Ile
        370                 375                 380

Thr Gly Ser Thr Tyr Ala Pro Ile Gly Glu Val His Lys Asp Asp Lys
385                 390                 395                 400

Pro Val Asn Cys His Gln Tyr Asp Gly Leu Val Glu Leu Ala Thr Ile
                405                 410                 415

Cys Ala Leu Cys Asn Asp Ser Ala Leu Asp Tyr Asn Glu Ala Lys Gly
                420                 425                 430

Val Tyr Glu Lys Val Gly Glu Ala Thr Glu Thr Ala Leu Thr Cys Leu
                435                 440                 445

Val Glu Lys Met Asn Val Phe Asp Thr Glu Leu Lys Gly Leu Ser Lys
        450                 455                 460

Ile Glu Arg Ala Asn Ala Cys Asn Ser Val Ile Lys Gln Leu Met Lys
465                 470                 475                 480

Lys Glu Phe Thr Leu Glu Phe Ser Arg Asp Arg Lys Ser Met Ser Val
                485                 490                 495

Tyr Cys Thr Pro Asn Lys Pro Ser Arg Thr Ser Met Ser Lys Met Phe
                500                 505                 510

Val Lys Gly Ala Pro Glu Gly Val Ile Asp Arg Cys Thr His Ile Arg
                515                 520                 525

Val Gly Ser Thr Lys Val Pro Met Thr Ser Gly Val Lys Gln Lys Ile
        530                 535                 540

Met Ser Val Ile Arg Glu Trp Gly Ser Gly Ser Asp Thr Leu Arg Cys
545                 550                 555                 560

Leu Ala Leu Ala Thr His Asp Asn Pro Leu Arg Arg Glu Glu Met His
                565                 570                 575

Leu Glu Asp Ser Ala Asn Phe Ile Lys Tyr Glu Thr Asn Leu Thr Phe
                580                 585                 590

Val Gly Cys Val Gly Met Leu Asp Pro Pro Arg Ile Glu Val Ala Ser
                595                 600                 605

Ser Val Lys Leu Cys Arg Gln Ala Gly Ile Arg Val Ile Met Ile Thr
        610                 615                 620

Gly Asp Asn Lys Gly Thr Ala Val Ala Ile Cys Arg Arg Ile Gly Ile
625                 630                 635                 640

Phe Gly Gln Asp Glu Asp Val Thr Ser Lys Ala Phe Thr Gly Arg Glu
                645                 650                 655

Phe Asp Glu Leu Asn Pro Ser Ala Gln Arg Asp Ala Cys Leu Asn Ala
                660                 665                 670

Arg Cys Phe Ala Arg Val Glu Pro Ser His Lys Ser Lys Ile Val Glu
                675                 680                 685

Phe Leu Gln Ser Phe Asp Glu Ile Thr Ala Met Thr Gly Asp Gly Val
        690                 695                 700

Asn Asp Ala Pro Ala Leu Lys Lys Ala Glu Ile Gly Ile Ala Met Gly
705                 710                 715                 720

Ser Gly Thr Ala Val Ala Lys Thr Ala Ser Glu Met Val Leu Ala Asp
                725                 730                 735
```

Asp Asn Phe Ser Thr Ile Val Ala Ala Val Glu Glu Gly Arg Ala Ile
            740                 745                 750

Tyr Asn Met Lys Gln Phe Ile Arg Tyr Leu Ile Ser Ser Asn Val
    755                 760                 765

Gly Glu Val Val Cys Ile Phe Leu Thr Ala Ala Leu Gly Phe Pro Glu
770                 775                 780

Ala Leu Ile Pro Val Gln Leu Leu Trp Val Asn Leu Val Thr Asp Gly
785                 790                 795                 800

Leu Pro Ala Thr Ala Leu Gly Phe Asn Pro Pro Asp Leu Asp Ile Met
                805                 810                 815

Asn Lys Pro Pro Arg Asn Pro Lys Glu Pro Leu Ile Ser Gly Trp Leu
                820                 825                 830

Phe Phe Arg Tyr Leu Ala Ile Gly Cys Tyr Val Gly Ala Ala Thr Val
            835                 840                 845

Gly Ala Ala Ala Trp Trp Phe Ile Ala Ala Asp Gly Gly Pro Arg Val
850                 855                 860

Ser Phe Tyr Gln Leu Ser His Phe Leu Gln Cys Lys Glu Asp Asn Pro
865                 870                 875                 880

Asp Phe Glu Gly Val Asp Cys Ala Ile Phe Glu Ser Pro Tyr Pro Met
                885                 890                 895

Thr Met Ala Leu Ser Val Leu Val Thr Ile Glu Met Cys Asn Ala Leu
                900                 905                 910

Asn Ser Leu Ser Glu Asn Gln Ser Leu Leu Arg Met Pro Pro Trp Glu
            915                 920                 925

Asn Ile Trp Leu Val Gly Ser Ile Cys Leu Ser Met Ser Leu His Phe
930                 935                 940

Leu Ile Leu Tyr Val Glu Pro Leu Pro Leu Ile Phe Gln Ile Thr Pro
945                 950                 955                 960

Leu Asn Val Thr Gln Trp Leu Met Val Leu Lys Ile Ser Leu Pro Val
                965                 970                 975

Ile Leu Met Asp Glu Thr Leu Lys Phe Val Ala Arg Asn Tyr Leu Glu
                980                 985                 990

Pro Ala Ile Leu Glu
        995

<210> SEQ ID NO 4
<211> LENGTH: 2991
<212> TYPE: DNA
<213> ORGANISM: Homo sapiens

<400> SEQUENCE: 4
atggagaacg cgcacaccaa gacggtggag gaggtgctgg gccacttcgg cgtcaacgag      60
agtacggggc tgagcctgga acaggtcaag aagcttaagg agagatgggg ctccaacgag     120
ttaccggctg aagaaggaaa aaccttgctg gaacttgtga ttgagcagtt tgaagacttg     180
ctagttagga ttttattact ggcagcatgt atatcttttg ttttggcttg gtttgaagaa     240
ggtgaagaaa caattacagc ctttgtagaa ccttttgtaa ttttactcat attagtagcc     300
aatgcaattg tgggtgtatg gcaggaaaga aatgctgaaa atgccatcga agcccttaag     360
gaatatgagc ctgaaatggg caaagtgtat cgacaggaca gaaagagtgt gcagcggatt     420
aaagctaaag acatagttcc tggtgatatt gtagaaattg ctgttggtga caaagttcct     480
gctgatataa ggttaacttc catcaaatct accacactaa gagttgacca gtcaattctc     540
acaggtgaat ctgtctctgt catcaagcac actgatcccg tccctgaccc acgagctgtc     600

```
aaccaagata aaaagaacat gctgttttct ggtacaaaca ttgctgctgg gaaagctatg    660
ggagtggtgg tagcaactgg agttaacacc gaaattggca agatccggga tgaaatggtg    720
gcaacagaac aggagagaac accccttcag caaaaactag atgaatttgg ggaacagctt    780
tccaaagtca tctcccttat ttgcattgca gtctggatca taaatattgg gcacttcaat    840
gacccggttc atggagggtc ctggatcaga ggtgctattt actactttaa aattgcagtg    900
gccctggctg tagcagccat tcctgaaggt ctgcctgcag tcatcaccac ctgcctggct    960
cttggaactc gcagaatggc aaagaaaaat gccattgttc gaagcctccc gtctgtggaa   1020
acccttggtt gtacttctgt tatctgctca gacaagactg gtacacttac aacaaaccag   1080
atgtcagtct gcaggatgtt cattctggac agagtggaag gtgatacttg ttcccttaat   1140
gagtttacca taactggatc aacttatgca cctattggag aagtgcataa agatgataaa   1200
ccagtgaatt gtcaccagta tgatggtctg gtagaattag caacaatttg tgctctttgt   1260
aatgactctg ctttggatta caatgaggca aagggtgtgt atgaaaaagt tggagaagct   1320
acagagactg ctctcacttg cctagtagag aagatgaatg tatttgatac cgaattgaag   1380 ggtcttttcta aaatagaacg tgcaaatgcc tgcaactcag tcattaaaca gctgatgaaa   1440
aaggaattca ctctagagtt ttcacgtgac agaaagtcaa tgtcggttta ctgtacacca   1500
aataaaccaa gcaggacatc aatgagcaag atgtttgtga agggtgctcc tgaaggtgtc   1560
attgacaggt gcacccacat tcgagttgga agtactaagg ttcctatgac ctctggagtc   1620
aaacagaaga tcatgtctgt cattcgagag tggggtagtg gcagcgacac actgcgatgc   1680
ctggccctgg ccactcatga caacccactg agaagagaag aaatgcacct tgaggactct   1740
gccaacttta ttaaatatga gaccaatctg accttcgttg gctgcgtggg catgctggat   1800
cctccgagaa tcgaggtggc ctcctccgtg aagctgtgcc ggcaagcagg catccgggtc   1860
atcatgatca ctggggacaa caagggcact gctgtggcca tctgtcgccg catcggcatc   1920
ttcgggcagg atgaggacgt gacgtcaaaa gctttcacag gccgggagtt tgatgaactc   1980
aacccctccg cccagcgaga cgcctgcctg aacgcccgct gttttgctcg agttgaaccc   2040
tcccacaagt ctaaaatcgt agaatttctt cagtcttttg atgagattac agctatgact   2100
ggcgatggcg tgaacgatgc tcctgctctg aagaaagccg agattggcat tgctatgggc   2160
tctggcactg cggtggctaa aaccgcctct gagatggtcc tggcggatga caacttctcc   2220
accattgtgg ctgccgttga ggaggggcgg gcaatctaca acaacatgaa acagttcatc   2280
cgctacctca tctcgtccaa cgtcggggaa gttgtctgta ttttcctgac agcagccctt   2340
ggatttcccg aggctttgat tcctgttcag ctgctctggg tcaatctggt gacagatggc   2400
ctgcctgcca ctgcactggg gttcaaccct cctgatctgg acatcatgaa taaacctccc   2460
cggaacccaa aggaaccatt gatcagcggg tggctctttt tccgttactt ggctattggc   2520
tgttacgtcg gcgctgctac cgtgggtgct gctgcatggt ggttcattgc tgctgacggt   2580
ggtccaagag tgtccttcta ccagctgagt catttcctac agtgtaaaga ggacaacccg   2640
gactttgaag gcgtggattg tgcaatcttt gaatccccat acccgatgac aatggcgctc   2700
tctgttctag taactataga aatgtgtaac gccctcaaca gcttgtccga aaaccagtcc   2760
ttgctgagga tgcccccctg ggagaacatc tggctcgtgg gctccatctg cctgtccatg   2820
tcactccact tcctgatcct ctatgtcgaa cccttgccac tcatcttcca gatcacaccg   2880
ctgaacgtga cccagtggct gatggtgctg aaaatctcct tgcccgtgat tctcatggat   2940
```

```
gagacgctca gtttgtggc ccgcaactac ctggaacctg caatactgga g            2991
```

```
<210> SEQ ID NO 5
<211> LENGTH: 22
<212> TYPE: PRT
<213> ORGANISM: Artificial Sequence
<220> FEATURE:
<223> OTHER INFORMATION: self-cleavage sequence derived from porcine
      teschovirus-1

<400> SEQUENCE: 5
```

Gly Ser Gly Ala Thr Asn Phe Ser Leu Leu Lys Gln Ala Gly Asp Val
1               5                   10                  15

Glu Glu Asn Pro Gly Pro
            20

```
<210> SEQ ID NO 6
<211> LENGTH: 66
<212> TYPE: DNA
<213> ORGANISM: Artificial Sequence
<220> FEATURE:
<223> OTHER INFORMATION: self-cleavage sequence derived from porcine
      teschovirus-1

<400> SEQUENCE: 6
```

```
ggaagcggag ctactaactt cagcctgctg aagcaggctg agacgtggga ggagaaccct    60
ggacct                                                               66
```

```
<210> SEQ ID NO 7
<211> LENGTH: 21
<212> TYPE: PRT
<213> ORGANISM: Artificial Sequence
<220> FEATURE:
<223> OTHER INFORMATION: self-cleavage sequence derived from
      Thoseaasigna virus

<400> SEQUENCE: 7
```

Gly Ser Gly Glu Gly Arg Gly Ser Leu Leu Thr Cys Gly Asp Val Glu
1               5                   10                  15

Glu Asn Pro Gly Pro
            20

```
<210> SEQ ID NO 8
<211> LENGTH: 63
<212> TYPE: DNA
<213> ORGANISM: Artificial Sequence
<220> FEATURE:
<223> OTHER INFORMATION: self-cleavage sequence derived from
      Thoseaasigna virus

<400> SEQUENCE: 8
```

```
ggaagcggag agggcagagg aagtctgcta acatgcggtg acgtcgagga gaatcctgga    60
cct                                                                  63
```

```
<210> SEQ ID NO 9
<211> LENGTH: 23
<212> TYPE: PRT
<213> ORGANISM: Artificial Sequence
<220> FEATURE:
<223> OTHER INFORMATION: self-cleavage sequence derived from equine
      rhinitis A virus (ERAV)

<400> SEQUENCE: 9
```

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 10
<211> LENGTH: 69
<212> TYPE: DNA
<213> ORGANISM: Artificial Sequence
<220> FEATURE:
<223> OTHER INFORMATION: self-cleavage sequence derived from equine
      rhinitis A virus (ERAV)

<400> SEQUENCE: 10
ggaagcggac agtgtactaa ttatgctctc ttgaaattgg ctggagatgt tgagagcaac     60
cctggacct                                                            69

<210> SEQ ID NO 11
<211> LENGTH: 25
<212> TYPE: PRT
<213> ORGANISM: Artificial Sequence
<220> FEATURE:
<223> OTHER INFORMATION: self-cleavage sequence derived from FMDV 2A

<400> SEQUENCE: 11

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 12
<211> LENGTH: 75
<212> TYPE: DNA
<213> ORGANISM: Artificial Sequence
<220> FEATURE:
<223> OTHER INFORMATION: self-cleavage sequence derived from FMDV 2A

<400> SEQUENCE: 12
ggaagcggag tgaaacagac tttgaatttt gaccttctca gttggcggg agacgtggag       60 tccaaccctg gacct                                                      75

<210> SEQ ID NO 13
<211> LENGTH: 18
<212> TYPE: DNA
<213> ORGANISM: Artificial Sequence
<220> FEATURE:
<223> OTHER INFORMATION: Forward primer for Mouse alpha-SMA

<400> SEQUENCE: 13
cccacccaga gtggagaa                                                   18

<210> SEQ ID NO 14
<211> LENGTH: 20
<212> TYPE: DNA
<213> ORGANISM: Artificial Sequence
<220> FEATURE:
<223> OTHER INFORMATION: Reverse primer for Mouse alpha-SMA

<400> SEQUENCE: 14
acatagctgg agcagcgtct                                                 20

<210> SEQ ID NO 15
<211> LENGTH: 21
<212> TYPE: DNA
<213> ORGANISM: Artificial Sequence
<220> FEATURE:

```
<223> OTHER INFORMATION: Forward primer for Mouse Collagen I

<400> SEQUENCE: 15
catgttcagc tttgtggacc t                                              21

<210> SEQ ID NO 16
<211> LENGTH: 20
<212> TYPE: DNA
<213> ORGANISM: Artificial Sequence
<220> FEATURE:
<223> OTHER INFORMATION: Reverse primer for Mouse Collagen I

<400> SEQUENCE: 16
gacgctgact tcagggatgt                                                20

<210> SEQ ID NO 17
<211> LENGTH: 20
<212> TYPE: DNA
<213> ORGANISM: Artificial Sequence
<220> FEATURE:
<223> OTHER INFORMATION: Forward primer for Mouse TGF-beta 1

<400> SEQUENCE: 17
tggagcaaca tgtggaactc                                                20

<210> SEQ ID NO 18
<211> LENGTH: 18
<212> TYPE: DNA
<213> ORGANISM: Artificial Sequence
<220> FEATURE:
<223> OTHER INFORMATION: Reverse primer for Mouse TGF-beta 1

<400> SEQUENCE: 18
cagcagccgg ttaccaag                                                  18

<210> SEQ ID NO 19
<211> LENGTH: 24
<212> TYPE: DNA
<213> ORGANISM: Artificial Sequence
<220> FEATURE:
<223> OTHER INFORMATION: Forward primer for Mouse IL-1 beta

<400> SEQUENCE: 19
tccaggatga ggacatgatg agca                                           24

<210> SEQ ID NO 20
<211> LENGTH: 25
<212> TYPE: DNA
<213> ORGANISM: Artificial Sequence
<220> FEATURE:
<223> OTHER INFORMATION: Reverse primer for Mouse IL-1 beta

<400> SEQUENCE: 20
gaacgtcaca cacaccagca ggtta                                          25

<210> SEQ ID NO 21
<211> LENGTH: 21
<212> TYPE: DNA
<213> ORGANISM: Artificial Sequence
<220> FEATURE:
<223> OTHER INFORMATION: Forward primer for Mouse RANTES

<400> SEQUENCE: 21
tgcagaggac tctgagacag c                                              21
```

```
<210> SEQ ID NO 22
<211> LENGTH: 19
<212> TYPE: DNA
<213> ORGANISM: Artificial Sequence
<220> FEATURE:
<223> OTHER INFORMATION: Reverse primer for Mouse RANTES

<400> SEQUENCE: 22
gagtggtgtc cgagccata                                                19

<210> SEQ ID NO 23
<211> LENGTH: 20
<212> TYPE: DNA
<213> ORGANISM: Artificial Sequence
<220> FEATURE:
<223> OTHER INFORMATION: Forward primer for Mouse F4/80

<400> SEQUENCE: 23
cctggacgaa tcctgtgaag                                               20

<210> SEQ ID NO 24
<211> LENGTH: 20
<212> TYPE: DNA
<213> ORGANISM: Artificial Sequence
<220> FEATURE:
<223> OTHER INFORMATION: Reverse primer for Mouse F4/80

<400> SEQUENCE: 24
ggtgggacca cagagagttg                                               20

<210> SEQ ID NO 25
<211> LENGTH: 18
<212> TYPE: DNA
<213> ORGANISM: Artificial Sequence
<220> FEATURE:
<223> OTHER INFORMATION: Forward primer for Mouse MCP-1

<400> SEQUENCE: 25
catccacgtg ttggctca                                                 18

<210> SEQ ID NO 26
<211> LENGTH: 23
<212> TYPE: DNA
<213> ORGANISM: Artificial Sequence
<220> FEATURE:
<223> OTHER INFORMATION: Reverse primer for Mouse MCP-1

<400> SEQUENCE: 26
gatcatcttg ctggtgaatg agt                                           23

<210> SEQ ID NO 27
<211> LENGTH: 20
<212> TYPE: DNA
<213> ORGANISM: Artificial Sequence
<220> FEATURE:
<223> OTHER INFORMATION: Forward primer for Mouse CCN5

<400> SEQUENCE: 27
atacaggtgc caggaaggtg                                               20

<210> SEQ ID NO 28
<211> LENGTH: 20
<212> TYPE: DNA
<213> ORGANISM: Artificial Sequence
<220> FEATURE:
<223> OTHER INFORMATION: Reverse primer for Mouse CCN5
```

```
<400> SEQUENCE: 28
gttggatact cgggtggcta                                               20

<210> SEQ ID NO 29
<211> LENGTH: 20
<212> TYPE: DNA
<213> ORGANISM: Artificial Sequence
<220> FEATURE:
<223> OTHER INFORMATION: Forward primer for Mouse GAPDH

<400> SEQUENCE: 29
ctcatgacca cagtccatgc                                               20

<210> SEQ ID NO 30
<211> LENGTH: 20
<212> TYPE: DNA
<213> ORGANISM: Artificial Sequence
<220> FEATURE:
<223> OTHER INFORMATION: Reverse primer for Mouse GAPDH

<400> SEQUENCE: 30
ttcagctctg ggatgacctt                                               20

<210> SEQ ID NO 31
<211> LENGTH: 20
<212> TYPE: DNA
<213> ORGANISM: Artificial Sequence
<220> FEATURE:
<223> OTHER INFORMATION: Forward primer for Mouse 18s rRNA

<400> SEQUENCE: 31
gtaacccgtt gaaccccatt                                               20

<210> SEQ ID NO 32
<211> LENGTH: 20
<212> TYPE: DNA
<213> ORGANISM: Artificial Sequence
<220> FEATURE:
<223> OTHER INFORMATION: Reverse primer for Mouse 18s rRNA

<400> SEQUENCE: 32
ccatccaatc ggtagtagcg                                               20

<210> SEQ ID NO 33
<211> LENGTH: 27
<212> TYPE: DNA
<213> ORGANISM: Artificial Sequence
<220> FEATURE:
<223> OTHER INFORMATION: Forward primer for Rat alpha-SMA

<400> SEQUENCE: 33
tctgtctcta gcacacaact gtgaatg                                       27

<210> SEQ ID NO 34
<211> LENGTH: 23
<212> TYPE: DNA
<213> ORGANISM: Artificial Sequence
<220> FEATURE:
<223> OTHER INFORMATION: Reverse primer for Rat alpha-SMA

<400> SEQUENCE: 34
ttgacaggcc agggctagaa ggg                                           23

<210> SEQ ID NO 35
<211> LENGTH: 26
```

```
<212> TYPE: DNA
<213> ORGANISM: Artificial Sequence
<220> FEATURE:
<223> OTHER INFORMATION: Forward primer for Rat Collagen I

<400> SEQUENCE: 35 aatgcactttt tggtttttgg tcacgt                                         26

<210> SEQ ID NO 36
<211> LENGTH: 21
<212> TYPE: DNA
<213> ORGANISM: Artificial Sequence
<220> FEATURE:
<223> OTHER INFORMATION: Reverse primer for Rat Collagen I

<400> SEQUENCE: 36
cagcccactt tgccccaacc c                                               21

<210> SEQ ID NO 37
<211> LENGTH: 20
<212> TYPE: DNA
<213> ORGANISM: Artificial Sequence
<220> FEATURE:
<223> OTHER INFORMATION: Forward primer for Rat TGF-beta 1

<400> SEQUENCE: 37
tgttcgcgct ctcggcagtg                                                 20

<210> SEQ ID NO 38
<211> LENGTH: 20
<212> TYPE: DNA
<213> ORGANISM: Artificial Sequence
<220> FEATURE:
<223> OTHER INFORMATION: Reverse primer for Rat TGF-beta 1

<400> SEQUENCE: 38
cggatggcct cgatgcgctt                                                 20

<210> SEQ ID NO 39
<211> LENGTH: 22
<212> TYPE: DNA
<213> ORGANISM: Artificial Sequence
<220> FEATURE:
<223> OTHER INFORMATION: Forward primer for Rat GAPDH

<400> SEQUENCE: 39
acccagccca gcaaggatac tg                                              22

<210> SEQ ID NO 40
<211> LENGTH: 23
<212> TYPE: DNA
<213> ORGANISM: Artificial Sequence
<220> FEATURE:
<223> OTHER INFORMATION: Reverse primer for Rat GAPDH

<400> SEQUENCE: 40
attcgagaga agggagggct ccc                                             23

<210> SEQ ID NO 41
<211> LENGTH: 753
<212> TYPE: DNA
<213> ORGANISM: Homo sapiens

<400> SEQUENCE: 41
atgagaggca caccgaagac ccacctcctg gccttctccc tcctctgcct cctctcaaag     60
```

| | |
|---|---|
| gtgcgtaccc agctgtgccc gacaccatgt acctgcccct ggccacctcc ccgatgcccg | 120 |
| ctgggagtac ccctggtgct ggatggctgt ggctgctgcc gggtatgtgc acggcggctg | 180 |
| ggggagccct gcgaccaact ccacgtctgc gacgccagcc agggcctggt ctgccagccc | 240 |
| ggggcaggac ccggtggccg gggggccctg tgcctcttgg cagaggacga cagcagctgt | 300 |
| gaggtgaacg gccgcctgta tcgggaaggg gagaccttcc agccccactg cagcatccgc | 360 |
| tgccgctgcg aggacggcgg cttcacctgc gtgccgctgt gcagcgagga tgtgcggctg | 420 |
| cccagctggg actgccccca ccccaggagg gtcgaggtcc tgggcaagtg ctgccctgag | 480 |
| tgggtgtgcg gccaaggagg gggactgggg acccagcccc ttccagccca aggaccccag | 540 |
| ttttctggcc ttgtctcttc cctgcccect ggtgtcccct gcccagaatg gagcacggcc | 600 |
| tggggaccct gctcgaccac ctgtgggctg ggcatggcca cccgggtgtc caaccagaac | 660 |
| cgcttctgcc gactggagac ccagcgccgc ctgtgcctgt ccaggccctg cccacccctcc | 720 |
| aggggtcgca gtccacaaaa cagtgccttc tag | 753 |

<210> SEQ ID NO 42
<211> LENGTH: 2994
<212> TYPE: DNA
<213> ORGANISM: Homo sapiens

<400> SEQUENCE: 42

| | |
|---|---|
| atggagaacg cgcacaccaa gacggtggag gaggtgctgg gccacttcgg cgtcaacgag | 60 |
| agtacggggc tgagcctgga acaggtcaag aagcttaagg agagatgggg ctccaacgag | 120 |
| ttaccggctg aagaaggaaa aaccttgctg gaacttgtga ttgagcagtt tgaagacttg | 180 |
| ctagttagga ttttattact ggcagcatgt atatcttttg ttttggcttg gtttgaagaa | 240 |
| ggtgaagaaa caattacagc ctttgtagaa ccttttgtaa ttttactcat attagtagcc | 300 |
| aatgcaattg tgggtgtatg gcaggaaaga aatgctgaaa atgccatcga agcccttaag | 360 |
| gaatatgagc tgaaatggg caaagtgtat cgacaggaca gaaagagtgt gcagcggatt | 420 |
| aaagctaaag acatagttcc tggtgatatt gtagaaattg ctgttggtga caaagttcct | 480 |
| gctgatataa ggttaacttc catcaaatct accacactaa gagttgacca gtcaattctc | 540 |
| acaggtgaat ctgtctctgt catcaagcac actgatcccg tccctgaccc acgagctgtc | 600 |
| aaccaagata aaaagaacat gctgttttct ggtacaaaca ttgctgctgg aaagctatg | 660 |
| ggagtggtgg tagcaactgg agttaacacc gaaattggca agatccggga tgaaatggtg | 720 |
| gcaacagaac aggagagaac accccttcag caaaaactag atgaatttgg ggaacagctt | 780 |
| tccaaagtca tctccttat tgcattgca gtctggatca taaatattgg gcacttcaat | 840 |
| gacccggttc atggagggtc ctggatcaga ggtgctattt actactttaa aattgcagtg | 900 |
| gccctggctg tagcagccat tcctgaaggt ctgcctgcag tcatcaccac ctgcctggct | 960 |
| cttggaactc gcagaatggc aaagaaaaat gccattgttc gaagcctccc gtctgtggaa | 1020 |
| acccttggtt gtacttctgt tatctgctca gacaagactg gtacacttac aacaaaccag | 1080 |
| atgtcagtct gcaggatgtt cattctggac agagtggaag gtgatacttg ttcccttaat | 1140 |
| gagtttacca taactggatc aacttatgca cctattggag aagtgcataa agatgataaa | 1200 |
| ccagtgaatt gtcaccagta tgatggtctg gtagaattag caacaatttg tgctctttgt | 1260 |
| aatgactctg ctttggatta caatgaggca aggggtgtgt atgaaaaagt tggagaagct | 1320 |
| acagagactg ctctcacttg cctagtagag aagatgaatg tatttgatac cgaattgaag | 1380 |
| ggtctttcta aaatagaacg tgcaaatgcc tgcaactcag tcattaaaca gctgatgaaa | 1440 |

```
-continued aaggaattca ctctagagtt ttcacgtgac agaaagtcaa tgtcggttta ctgtacacca    1500
aataaaccaa gcaggacatc aatgagcaag atgtttgtga agggtgctcc tgaaggtgtc    1560
attgacaggt gcacccacat tcgagttgga agtactaagg ttcctatgac ctctggagtc    1620
aaacagaaga tcatgtctgt cattcgagag tggggtagtg gcagcgacac actgcgatgc    1680
ctggccctgg ccactcatga caacccactg agaagagaag aaatgcacct tgaggactct    1740
gccaacttta ttaaatatga gaccaatctg accttcgttg gctgcgtggg catgctggat    1800
cctccgagaa tcgaggtggc ctcctccgtg aagctgtgcc ggcaagcagg catccgggtc    1860
atcatgatca ctggggacaa caagggcact gctgtggcca tctgtcgccg catcggcatc    1920
ttcgggcagg atgaggacgt gacgtcaaaa gctttcacag gccgggagtt tgatgaactc    1980 aaccccccg cccagcgaga cgcctgcctg aacgcccgct gttttgctcg agttgaaccc    2040
tcccacaagt ctaaaatcgt agaatttctt cagtcttttg atgagattac agctatgact    2100
ggcgatggcg tgaacgatgc tcctgctctg aagaaagccg agattggcat tgctatgggc    2160
tctggcactg cggtggctaa aaccgcctct gagatggtcc tggcggatga caacttctcc    2220
accattgtgg ctgccgttga ggaggggcgg gcaatctaca acaacatgaa acagttcatc    2280
cgctacctca tctcgtccaa cgtcggggaa gttgtctgta ttttcctgac agcagccctt    2340
ggatttcccg aggctttgat tcctgttcag ctgctctggg tcaatctggt gacagatggc    2400
ctgcctgcca ctgcactggg gttcaaccct cctgatctgg acatcatgaa taaacctccc    2460
cggaacccaa aggaaccatt gatcagcggg tggctctttt tccgttactt ggctattggc    2520
tgttacgtcg gcgctgctac cgtgggtgct gctgcatggt ggttcattgc tgctgacggt    2580
ggtccaagag tgtccttcta ccagctgagt catttcctac agtgtaaaga ggacaacccg    2640
gactttgaag gcgtggattg tgcaatcttt gaatccccat acccgatgac aatggcgctc    2700
tctgttctag taactataga aatgtgtaac gccctcaaca gcttgtccga aaaccagtcc    2760
ttgctgagga tgcccccctg ggagaacatc tggctcgtgg gctccatctg cctgtccatg    2820
tcactccact tcctgatcct ctatgtcgaa cccttgccac tcatcttcca gatcacaccg    2880
ctgaacgtga cccagtggct gatggtgctg aaaatctcct tgcccgtgat tctcatggat    2940
gagacgctca agtttgtggc ccgcaactac ctggaacctg caatactgga gtag          2994
```